US012123061B2

(12) United States Patent
Barry et al.

(10) Patent No.: US 12,123,061 B2
(45) Date of Patent: Oct. 22, 2024

(54) METHOD FOR THE DETECTION OF LEGIONELLA

(71) Applicant: National University of Ireland, Galway, Galway (IE)

(72) Inventors: Thomas Barry, Galway (IE); Kate Reddington, Westport (IE); Elizabeth Minogue, Whitegate (IE)

(73) Assignee: National University of Ireland, Galway, Galway (IE)

( * ) Notice: Subject to any disclaimer, the term of this patent is extended or adjusted under 35 U.S.C. 154(b) by 452 days.

(21) Appl. No.: 16/339,968

(22) PCT Filed: Oct. 4, 2017

(86) PCT No.: PCT/EP2017/075265
§ 371 (c)(1),
(2) Date: Apr. 5, 2019

(87) PCT Pub. No.: WO2018/065497
PCT Pub. Date: Apr. 12, 2018

(65) Prior Publication Data

US 2019/0284616 A1 Sep. 19, 2019

(30) Foreign Application Priority Data

Oct. 5, 2016 (EP) .................................... 16192489

(51) Int. Cl.
*C12Q 1/68* (2018.01)
*C12Q 1/689* (2018.01)

(52) U.S. Cl.
CPC ........ *C12Q 1/689* (2013.01); *C12Q 2600/112* (2013.01); *C12Q 2600/16* (2013.01); *Y02A 50/30* (2018.01)

(58) Field of Classification Search
None
See application file for complete search history.

(56) References Cited

U.S. PATENT DOCUMENTS 11,085,090 B2 * 8/2021 Reddington ........... C12Q 1/689

FOREIGN PATENT DOCUMENTS

WO WO2011/133433 A2 10/2011
WO WO-2013187958 A1 * 12/2013 ............. C12Q 1/689
WO WO-2016188962 A1 * 12/2016 ............. C12Q 1/689

OTHER PUBLICATIONS

Cazalet et al. (Genome Research, 2008, 18:431-441) (Year: 2008).*
Petzold et al. (BMC Microbiology 2013, 13:198, including supplemental Table S1, 14 pages) (Year: 2013).*
GenBank HF678227 . Legionella pneumophila serogroup 1 lipopolysaccharide biosynthesis gene cluster, strain Goerlitz 6543. Sep. 3, 2013. 16 pages. (Year: 2013).*
Collins et al. (Journal of Applied Microbiology 2015; 119, 1158-1169) (Year: 2015).*
Benitez and Winchell, Clinical Application of a Multiplex Real-Time PCT Assay for Simultaneous Detection of a Legionella . . . , J Clin Microbiol, 2013, pp. 348-351, v. 51(1).
Collins et al., Real-time PCR to supplement gold-standard culture-based detection of Legionella . . . , J Applied Microbiol, 2015, pp. 1158-1169, v. 119.
Kim et al., Multiplex real-time PCR assay for *Legionella* species, Molecular and Cellular Probes, 2015, pp. 414-419, v. 29.
Janczarek and Palusinska-Szysz, PCR method for the rapid detection and discrimination of *Legionella* spp . . . , J Applied Genetics, 2016, pp. 251-261, v. 57.
Thurmer, et al., PCR-based 'serotyping' of Legionella pneumophilia, J Medical Microbiol., 2009, pp. 588-595, v. 58.
Costa Roldan, International Search Report for PCT/EP2017/075265, Nov. 29, 2017.

* cited by examiner

*Primary Examiner* — Juliet C Switzer
(74) *Attorney, Agent, or Firm* — Hovey Williams LLP; Crissa A. Cook

(57) ABSTRACT

This invention relates to the detection of *Legionella*, more specifically *Legionella pneumophila*, more specifically *Legionella pneumophila* serogroup 1, in a sample. Methods of detection, and assays and kits useful for detection, are also disclosed. The invention provides a method for identifying the presence, absence, or quantity of *Legionella pneumophila* serogroup 1 in a sample, the method comprising the steps of detecting the presence, absence, or quantity of at least part of the nucleic acid sequence of the lpg0768 gene or an expression product thereof, and correlating the presence, absence, or quantity of the at least part of the nucleic acid sequence of the lpg0768 gene or an expression product thereof, to the presence, absence, or quantity of *Legionella pneumophila* serogroup 1 in the sample.

4 Claims, 6 Drawing Sheets

Specification includes a Sequence Listing.

SEQUENCE LISTING

```
<160> NUMBER OF SEQ ID NOS: 52

<210> SEQ ID NO 1
<211> LENGTH: 1092
<212> TYPE: DNA
<213> ORGANISM: Legionella pneumophila

<400> SEQUENCE: 1

ctaacaatca ttttttgct taatatccga ccatttaatg ggttcaccta tagatacctt     60

gttttgtaat tcccagccat ttaccagatc ccagtattgg gtcgggactc ccttacaagg    120

aaaggcaaag gttgtattat caaggctaat tagagagcca ggttgaagtt tttgctttgc    180

aaccaaacaa gttctttgag agctgccaag tactcctttt ataggagctt ctagatctcg    240

catcggttga cctaaagctt gccaacaatt gtaaattgtt tcaagagtct tggctaattg    300

ctcaatcccc atagtatgtg atatgtcctg atcaatatct tctggataga gatgaactcc    360

tttttccagg attgaagctc ccaatgcaat agacatatac aacatttcaa ttccattata    420

atggtcagat aaaccaactg gtaatgaaaa acattggttt aaagttcgta acattcttag    480

gttatgtgct tctggcaaag caggatgtcc atcaggacta tgttcaataa taatttttc    540

acatccggca ctttttgctg tttcaactgc tttgcatata tcagttaaag aagatcttcc    600
```

-continued agtgtcaata atgagcggta atcctgtttt tgccagatga cgaattaaag gaacatggac 660
aatgttcgat gaagaggttt tgagtgcgca ggcaccctgc tttatcgcaa aatcaatagt 720
gtccaattca taaatcgaaa ctatgaaggg taaattggca ttctttaata gtgaaaatag 780
catactataa tgttctaaag gcagtacttt tctctcaatt aatgagcggt agttttcctt 840
gcggacctca ccggatttac tggtataggt ttcttcataa tcaacaggta ggcaaatgtt 900
tgggttattt aaaatttctg tttttagtat aagaggttgg tatggtactt tatccctgat 960
ggttataatt ttgtgtagca attgttcagc tatgccaaga tcctgattaa aaaaagtacc 1020
tatttctgct aaaaaaatag gaggatgatt ttcttcaaca gagaatggac caattgtaaa 1080
aggctgactc at 1092

<210> SEQ ID NO 2
<211> LENGTH: 19
<212> TYPE: DNA
<213> ORGANISM: Unknown
<220> FEATURE:
<223> OTHER INFORMATION: Synthetic oligonucleotide

<400> SEQUENCE: 2
agctcccaat gcaatagac 19

<210> SEQ ID NO 3
<211> LENGTH: 19
<212> TYPE: DNA
<213> ORGANISM: Unknown
<220> FEATURE:
<223> OTHER INFORMATION: Synthetic oligonucleotide

<400> SEQUENCE: 3
gcaaagcagt tgaaacagc 19

<210> SEQ ID NO 4
<211> LENGTH: 25
<212> TYPE: DNA
<213> ORGANISM: Unknown
<220> FEATURE:
<223> OTHER INFORMATION: Synthetic oligonucleotide

<400> SEQUENCE: 4
ccaactggta atgaaaaaca ttggt 25

<210> SEQ ID NO 5
<211> LENGTH: 405
<212> TYPE: DNA
<213> ORGANISM: Legionella pneumophila

<400> SEQUENCE: 5
ggggcgacct ggcttcgacg tgggttgcaa aaccggaagt gcatgccgag aaggagatct 60
ctcgtaaata agactcaatt aaatataaat gcaaacgatg aaaactttgc tggtggggaa 120
gctatcgctg cctaataagc actttagtta aaccatcact gtgtactggc caataaaccc 180
agtatcccgt tcgaccgagc ccgcttatcg gtatcgaatc aacggtcata agagataagc 240
tagcgtccta atctatcccg ggttatggcg cgaaactcag ggaatcgctg tgtatcatcc 300
tgcccgtcgg aggagccaca gttaaattca aaagacaagg ctatgcatgt agagctaaag 360
gcagaggact tgcggacgcg ggttcgattc ccgccgcctc cacca 405

<210> SEQ ID NO 6

-continued

<211> LENGTH: 471
<212> TYPE: DNA
<213> ORGANISM: Legionella pneumophila

<400> SEQUENCE: 6
atgactacca aaaaacaacc agattccacc atagccttga atagaaaagc tggttttgat 60
tactttattg aagatcaata cgaagcaggc ctggttttgg aaggctggga agtaaaaagt 120
ctgcgtgctg gaaaaatcaa tttgtcggat tcacacgtga taatcaaata cggtgaggca 180
ttcctattgg gcgcccaaat acagcctctt cccaccgcat ccactcattt tattcctgat 240
ccgatcagga cgcgcaagct attgatgaat aaaaaagaat taaaccatct cataggaagt 300
gttgaaaggc aaggctatac catagtccct ctttctttgt attggaaaaa aaataaaatt 360
aaaataaaaa ttgctctggc taaaggaaaa aaagagcatg acaaaagaga cacgatcaaa 420
gacagagaat ggcaaaggga tcgttcaaga ataatgaaaa agaacacttg a 471

<210> SEQ ID NO 7
<211> LENGTH: 21
<212> TYPE: DNA
<213> ORGANISM: Unknown
<220> FEATURE:
<223> OTHER INFORMATION: Synthetic oligonucleotide

<400> SEQUENCE: 7
cacgtgataa tmaaatacgg t 21

<210> SEQ ID NO 8
<211> LENGTH: 19
<212> TYPE: DNA
<213> ORGANISM: Unknown
<220> FEATURE:
<223> OTHER INFORMATION: Synthetic oligonucleotide

<400> SEQUENCE: 8
ttcatcaata gcttgcgyg 19

<210> SEQ ID NO 9
<211> LENGTH: 26
<212> TYPE: DNA
<213> ORGANISM: Unknown
<220> FEATURE:
<223> OTHER INFORMATION: Synthetic oligonucleotide

<400> SEQUENCE: 9
cygcatccac tcattttatt cctgat 26

<210> SEQ ID NO 10
<211> LENGTH: 14
<212> TYPE: DNA
<213> ORGANISM: Unknown
<220> FEATURE:
<223> OTHER INFORMATION: Synthetic oligonucleotide

<400> SEQUENCE: 10
ggcgacctgg cttc 14

<210> SEQ ID NO 11
<211> LENGTH: 21
<212> TYPE: DNA
<213> ORGANISM: Unknown
<220> FEATURE:
<223> OTHER INFORMATION: Synthetic oligonucleotide

<400> SEQUENCE: 11
tatgaccgtt gattcgatac c 21

<210> SEQ ID NO 12
<211> LENGTH: 17
<212> TYPE: DNA
<213> ORGANISM: Unknown
<220> FEATURE:
<223> OTHER INFORMATION: Synthetic oligonucleotide

<400> SEQUENCE: 12
acgtgggttg craaacc 17

<210> SEQ ID NO 13
<211> LENGTH: 19
<212> TYPE: DNA
<213> ORGANISM: Unknown
<220> FEATURE:
<223> OTHER INFORMATION: Synthetic oligonucleotide

<400> SEQUENCE: 13
ttcatcaaca gcttgcgtg 19

<210> SEQ ID NO 14
<211> LENGTH: 18
<212> TYPE: DNA
<213> ORGANISM: Unknown
<220> FEATURE:
<223> OTHER INFORMATION: Synthetic oligonucleotide

<400> SEQUENCE: 14
gatcaatacg aagcaggc 18

<210> SEQ ID NO 15
<211> LENGTH: 20
<212> TYPE: DNA
<213> ORGANISM: Unknown
<220> FEATURE:
<223> OTHER INFORMATION: Synthetic oligonucleotide

<400> SEQUENCE: 15
gccattctct gtctttgatc 20

<210> SEQ ID NO 16
<211> LENGTH: 22
<212> TYPE: DNA
<213> ORGANISM: Unknown
<220> FEATURE:
<223> OTHER INFORMATION: Synthetic oligonucleotide

<400> SEQUENCE: 16
ccaagtaggg tttctaacaa tc 22

<210> SEQ ID NO 17
<211> LENGTH: 21
<212> TYPE: DNA
<213> ORGANISM: Unknown
<220> FEATURE:
<223> OTHER INFORMATION: Synthetic oligonucleotide

<400> SEQUENCE: 17
gagtcagcct tttacaattg g 21

<210> SEQ ID NO 18
<211> LENGTH: 19
<212> TYPE: DNA

<213> ORGANISM: Unknown
<220> FEATURE:
<223> OTHER INFORMATION: Synthetic oligonucleotide

<400> SEQUENCE: 18
atgccagtca gcataagga 19

<210> SEQ ID NO 19
<211> LENGTH: 21
<212> TYPE: DNA
<213> ORGANISM: Unknown
<220> FEATURE:
<223> OTHER INFORMATION: Synthetic oligonucleotide

<400> SEQUENCE: 19
cagacctctg gtaggatgta c 21

<210> SEQ ID NO 20
<211> LENGTH: 20
<212> TYPE: DNA
<213> ORGANISM: Unknown
<220> FEATURE:
<223> OTHER INFORMATION: Synthetic oligonucleotide

<400> SEQUENCE: 20
tcggcactac cgacacgaac 20

<210> SEQ ID NO 21
<211> LENGTH: 1091
<212> TYPE: DNA
<213> ORGANISM: Legionella pneumophila

<400> SEQUENCE: 21
taacaatcat ttttttgctt aatatccgac catttaatgg gttcacctat agataccttg 60
ttttgtaatt cccagccatt taccagatcc cagtattggg taggaactcc cttacaagga 120
aaggcaaagg ttgtattatc aaggctaatt agagagccgg gttgaagttt ttgctttgca 180
accaaacaag ttctttgaga gctgccaagt actcctttta taggggtttc tagatctcgc 240
attggttgac ctaaagcttg ccaacaattg taaattgttt caagagtctt ggctaattga 300
tcaatcccca tagtatgtga tatgtcctga tcgatatctt ctggatagag atgaactcct 360
ttttccagga ttgaagctcc caatgcaata gacatataca acatttcaat tccattataa 420
tggtcagata aaccaactgg taatgaaaaa cattggttta aagttcgtaa cattcttagg 480
ttatgtgctt ctggcaaagc aggatgtcca tcagggctat gttcaataat aattttttca 540
catccggcac tttttgctgt ttcaactgct ttgcatatat cagttaagga agatcttcca 600
gtgtcaataa tgagcggtaa tcctgttttt gccagatgac gaattaaagg aatatggaca 660
atgttcgatg aagaggtttt gagtgcgcag gccccctgct ttatcgcaaa atcaatagtg 720
tccaattcat aaatcgaaac tatgaagggt aaattggcat tctttaatag tgaaaatagc 780
atactataat gttctaaagg cagtactttt ctctcaatta atgagcggta gttttccttg 840
cgaacctcac ctgatttact ggtataggtt tcttcataat caacaggtag gcaaatgttt 900
gggttattta aaatttctgt ttttagtata agaggttggt atggtacttt atccctgatg 960
gttataattt tgtgtagcaa ttgttcagct atgccaagat cctgattaaa aaaagtacct 1020
atttctgcta aaaaaatagg aggatgattt tcttcaacag agaatggacc aattgtaaaa 1080
ggctgactca t 1091

-continued

<210> SEQ ID NO 22
<211> LENGTH: 1091
<212> TYPE: DNA
<213> ORGANISM: Legionella pneumophila

<400> SEQUENCE: 22
taacaatcat ttttttgctt aatatccgac catttaatgg gttcacctat agataccttg 60
ttttgtaatt cccagccatt taccagatcc cagtattggg taggaactcc cttacaagga 120
aaggcaaagg ttgtattatc aaggctaatt agagagccgg gttgaagttt ttgctttgca 180
accaaacaag ttctttgaga gctgccaagt actcctttta taggggtttc tagatctcgc 240
attggttgac ctaaagcttg ccaacaattg taaattgttt caagagtctt ggctaattga 300
tcaatcccca tagtatgtga tatgtcctga tcgatatctt ctggatagag atgaactcct 360
ttttccagga ttgaagctcc caatgcaata gacatataca acatttcaat tccattataa 420
tggtcagata aaccaactgg taatgaaaaa cattggttta aagttcgtaa cattcttagg 480
ttatgtgctt ctggcaaagc aggatgtcca tcagggctat gttcaataat aatttttca 540 catccggcac tttttgctgt ttcaactgct ttgcatatat cagttaagga agatcttcca 600
gtgtcaataa tgagcggtaa tcctgttttt gccagatgac gaattaaagg aatatggaca 660
atgttcgatg aagaggtttt gagtgcgcag gccccctgct ttatcgcaaa atcaatagtg 720
tccaattcat aaatcgaaac tatgaagggt aaattggcat tctttaatag tgaaaatagc 780
atactataat gttctaaagg cagtactttt ctctcaatta atgagcggta gttttccttg 840
cgaacctcac ctgatttact ggtataggtt tcttcataat caacaggtag gcaaatgttt 900
gggttattta aaatttctgt ttttagcata agaggttggt atggtacttt atccctgatg 960
gttataattt tgtgtagcaa ttgttcagct atgccaagat cctgattaaa aaaagtacct 1020
atttctgcta aaaaaatagg aggatgattt tcttcaacag agaatggacc aattgtaaaa 1080
ggctgactca t 1091

<210> SEQ ID NO 23
<211> LENGTH: 1091
<212> TYPE: DNA
<213> ORGANISM: Legionella pneumophila

<400> SEQUENCE: 23
ctaacaatca tttttttgct taatatccga ccatttaatg ggttcaccta tagatacctt 60
gttttgtaat tcccacccat ttaccagatc ccagtattgg gtcggtactc ccttgcaagg 120
aaaggcaaag gttgtattat caaggctaat tagagtacca ggatgaagtt cttgttttgc 180
aaccaaacaa gttctttgag agctaccaag tactcctttt atgggagctt ctagatctcg 240
catcggttga cctaaagctt gccaacaatt gtaaattgtt taagagtctt ggctaattgc 300
tcaatcccca tagtatgtga tatgtcctga tcaatatctt ctggatagag atgaactcct 360
ttttccagga ttgaagctcc caatgcaata gacatataca acatttcaat tccattataa 420
tggtcagata aaccaactgg taatgaaaaa cattggttta aagttcgtaa cattcttagg 480
ttatgtgctt ctggcaaagc aggatgtcca tcaggactat gttcaataat aatttttca 540 catccggcac tttttgctgt ttcaactgct ttgcatatat cagttaaaga agatcttcca 600
gtgtcaataa tgagcggtaa tcctgttttt gccagatgac gaattaaagg aacatggaca 660
atgttcgatg aagaggtttt gagtgcgcag gcaccctgct ttatcgcaaa atcaatagtg 720
tccaattcat aaatcgaaac tatgaagggt aaattggcat tctttaatag tgaaaatagc 780

-continued

```
atactataat gttctaaagg cagtactttt ctctcaatta atgagcggta gttttccttg    840

cggacctcac ctgatttact ggtataggtt tcttcataat caacaggtag gcaaatgttt    900

gggttattta aaatttctgt ttttagtata agaggttgat acggtacttt atccctgatg    960

gttataattt tgtgtagtaa ttgttcggct acaccaagat cctgattaaa aaaagtacca   1020

atttctgcca aaaaaatagg aggatgattt tctccaatag agaatggacc aattgtaaaa   1080

ggctgactca t                                                         1091
```

<210> SEQ ID NO 24
<211> LENGTH: 1074
<212> TYPE: DNA
<213> ORGANISM: Legionella pneumophila

<400> SEQUENCE: 24

```
taacaatcat ttttttgctt aatatccgac catttaatgg gttcacctat agataccttg     60

ttttgtaatt cccagccatt taccagatcc cagtattggg taggaactcc cttacaagga    120

aaggcaaagg ttgtattatc aaggctaatt agagagccgg gttgaagttt ttgctttgca    180

accaaacaag ttctttgaga gctgccaagt actcctttta taggggtttc tagatctcgc    240

attggttgac ctaaagcttg ccaacaattg taaattgttt caagagtctt ggctaattga    300

tcaatcccca tagtatgtga tatgtcctga tcgatatctt ctggatagag atgaactcct    360

ttttccagga ttgaagctcc caatgcaata gacatataca acatttcaat tccattataa    420

tggtcagata aaccaactgg taatgaaaaa cattggttta aagttcgtaa cattcttagg    480

ttatgtgctt ctggcaaagc aggatgtcca tcaggactat gttcaataat aatttttttca    540

catccggcac tttttgctgt ttcaactgct ttgcatatat cagttaagga agatcttcca    600

gtgtcaataa tgagcggtaa tcctgttttt gccagatgac gaattaaagg aatatggaca    660

atgttcgatg aagaggtttt gagtgcgcag gccccctgct ttatcgcaaa atcaatagtg    720

tccaattcat aaatcgaaac tatgaagggt aaattggcat tctttaatag tgaaaatagc    780

atactataat gttctaaagg cagtactttt ctctcaatta atgagcggta gttttccttg    840

cgaacctcac ctgatttact ggtataggtt tcttcataat caacaggtag gcaaatgttt    900

gggttattta aaatttctgt ttttagtata agaggttgat acggtatttt atccctgata    960

cttataattt tgtgtagcaa ttgttcagct atgccaagat cctgattaaa aaaagtacct   1020

atttctgcta aaaaaatagg aggatgattt tctccaatag agtaggggcc aatt         1074
```

<210> SEQ ID NO 25
<211> LENGTH: 1074
<212> TYPE: DNA
<213> ORGANISM: Legionella pneumophila

<400> SEQUENCE: 25

```
taacaatcat ttttttgctt aatatccgac catttaatgg gttcacctat agataccttg     60

ttttgtaatt cccagccatt taccagatcc cagtattggg taggaactcc cttacaagga    120

aaggcaaagg ttgtattatc aaggctaatt agagagccgg gttgaagttt ttgctttgca    180

accaaacaag ttctttgaga gctgccaagt actcctttta taggggtttc tagatctcgc    240

attggttgac ctaaagcttg ccaacaattg taaattgttt caagagtctt ggctaattga    300

tcaatcccca tagtatgtga tatgtcctga tcgatatctt ctggatagag atgaactcct    360

ttttccagga ttgaagctcc caatgcaata gacatataca acatttcaat tccattataa    420

tggtcagata aaccaactgg taatgaaaaa cattggttta aagttcgtaa cattcttagg    480
```

```
ttatgtgctt ctggcaaagc aggatgtcca tcaggactat gttcaataat aatttttttca    540

catccggcac tttttgctgt ttcaactgct ttgcatatat cagttaagga agatcttcca    600

gtgtcaataa tgagcggtaa tcctgttttt gccagatgac gaattaaagg aatatggaca    660

atgttcgatg aagaggtttt gagtgcgcag gccccctgct ttatcgcaaa atcaatagtg    720

tccaattcat aaatcgaaac tatgaagggt aaattggcat tctttaatag tgaaaatagc    780

atactataat gttctaaagg cagtactttt ctctcaatta atgagcggta gttttccttg    840

cgaacctcac ctgatttact ggtataggtt tcttcataat caacaggtag gcaaatgttt    900

gggttattta aaatttctgt ttttagtata agaggttgat acggtatttt atccctgata    960

cttataattt tgtgtagcaa ttgttcagct atgccaagat cctgattaaa aaaagtacct   1020

atttctgcta aaaaaatagg aggatgattt tctccaatag agtaggggcc aatt         1074
```

<210> SEQ ID NO 26
<211> LENGTH: 1074
<212> TYPE: DNA
<213> ORGANISM: Legionella pneumophila

<400> SEQUENCE: 26

```
taacaatcat ttttttgctt aatatccgac catttaatgg gttcacctat agataccttg     60

ttttgtaatt cccagccatt taccagatcc cagtattggg taggaactcc cttacaagga    120

aaggcaaagg ttgtattatc aaggctaatt agagagccgg gttgaagttt ttgctttgca    180

accaaacaag ttctttgaga gctgccaagt actcctttta taggggtttc tagatctcgc    240

attggttgac ctaaagcttg ccaacaattg taaattgttt caagagtctt ggctaattga    300

tcaatcccca tagtatgtga tatgtcctga tcgatatctt ctggatagag atgaactcct    360

ttttccagga ttgaagctcc caatgcaata gacatataca acatttcaat tccattataa    420

tggtcagata aaccaactgg taatgaaaaa cattggttta aagttcgtaa cattcttagg    480

ttatgtgctt ctggcaaagc aggatgtcca tcaggactat gttcaataat aatttttttca    540

catccggcac tttttgctgt ttcaactgct ttgcatatat cagttaagga agatcttcca    600

gtgtcaataa tgagcggtaa tcctgttttt gccagatgac gaattaaagg aatatggaca    660

atgttcgatg aagaggtttt gagtgcgcag gccccctgct ttatcgcaaa atcaatagtg    720

tccaattcat aaatcgaaac tatgaagggt aaattggcat tctttaatag tgaaaatagc    780

atactataat gttctaaagg cagtactttt ctctcaatta atgagcggta gttttccttg    840

cgaacctcac ctgatttact ggtataggtt tcttcataat caacaggtag gcaaatgttt    900

gggttattta aaatttctgt ttttagtata agaggttgat acggtatttt atccctgata    960

cttataattt tgtgtagcaa ttgttcagct atgccaagat cctgattaaa aaaagtacct   1020

atttctgcta aaaaaatagg aggatgattt tctccaatag agtaggggcc aatt         1074
```

<210> SEQ ID NO 27
<211> LENGTH: 1074
<212> TYPE: DNA
<213> ORGANISM: Legionella pneumophila

<400> SEQUENCE: 27

```
taacaatcat ttttttgctt aatatccgac catttaatgg gttcacctat agataccttg     60

ttttgtaatt cccagccatt taccagatcc cagtattggg taggaactcc cttacaagga    120

aaggcaaagg ttgtattatc aaggctaatt agagagccgg gttgaagttt ttgctttgca    180
```

```
accaaacaag ttctttgaga gctgccaagt actcctttta taggggtttc tagatctcgc    240
attggttgac ctaaagcttg ccaacaattg taaattgttt caagagtctt ggctaattga    300
tcaatcccca tagtatgtga tatgtcctga tcgatatctt ctggatagag atgaactcct    360
ttttccagga ttgaagctcc caatgcaata gacatataca acatttcaat tccattataa    420
tggtcagata aaccaactgg taatgaaaaa cattggttta aagttcgtaa cattcttagg    480
ttatgtgctt ctggcaaagc aggatgtcca tcaggactat gttcaataat aatttttca    540
catccggcac tttttgctgt ttcaactgct ttgcatatat cagttaagga agatcttcca    600
gtgtcaataa tgagcggtaa tcctgttttt gccagatgac gaattaaagg aatatggaca    660
atgttcgatg aagaggtttt gagtgcgcag gccccctgct ttatcgcaaa atcaatagtg    720
tccaattcat aaatcgaaac tatgaagggt aaattggcat tctttaatag tgaaaatagc    780
atactataat gttctaaagg cagtactttt ctctcaatta atgagcggta gttttccttg    840
cgaacctcac ctgatttact ggtataggtt tcttcataat caacaggtag gcaaatgttt    900
gggttattta aaatttctgt ttttagtata agaggttgat acggtatttt atccctgata    960
cttataattt tgtgtagcaa ttgttcagct atgccaagat cctgattaaa aaaagtacct   1020
atttctgcta aaaaaatagg aggatgattt tctccaatag agtaggggcc aatt         1074
```

<210> SEQ ID NO 28
<211> LENGTH: 1074
<212> TYPE: DNA
<213> ORGANISM: Legionella pneumophila

<400> SEQUENCE: 28

```
taacaatcat ttttttgctt aatatccgac catttaatgg gttcacctat agataccttg     60
ttttgtaatt cccagccatt taccagatcc cagtattggg taggaactcc cttacaagga    120
aaggcaaagg ttgtattatc aaggctaatt agagagccgg gttgaagttt ttgctttgca    180
accaaacaag ttctttgaga gctgccaagt actcctttta taggggtttc tagatctcgc    240
attggttgac ctaaagcttg ccaacaattg taaattgttt caagagtctt ggctaattga    300
tcaatcccca tagtatgtga tatgtcctga tcgatatctt ctggatagag atgaactcct    360
ttttccagga ttgaagctcc caatgcaata gacatataca acatttcaat tccattataa    420
tggtcagata aaccaactgg taatgaaaaa cattggttta aagttcgtaa cattcttagg    480
ttatgtgctt ctggcaaagc aggatgtcca tcaggactat gttcaataat aatttttca    540
catccggcac tttttgctgt ttcaactgct ttgcatatat cagttaagga agatcttcca    600
gtgtcaataa tgagcggtaa tcctgttttt gccagatgac gaattaaagg aatatggaca    660
atgttcgatg aagaggtttt gagtgcgcag gccccctgct ttatcgcaaa atcaatagtg    720
tccaattcat aaatcgaaac tatgaagggt aaattggcat tctttaatag tgaaaatagc    780
atactataat gttctaaagg cagtactttt ctctcaatta atgagcggta gttttccttg    840
cgaacctcac ctgatttact ggtataggtt tcttcataat caacaggtag gcaaatgttt    900
gggttattta aaatttctgt ttttagtata agaggttgat acggtatttt atccctgata    960
cttataattt tgtgtagcaa ttgttcagct atgccaagat cctgattaaa aaaagtacct   1020
atttctgcta aaaaaatagg aggatgattt tctccaatag agtaggggcc aatt         1074
```

<210> SEQ ID NO 29
<211> LENGTH: 1074
<212> TYPE: DNA
<213> ORGANISM: Legionella pneumophila -continued

<400> SEQUENCE: 29

```
taacaatcat ttttttgctt aatatccgac catttaatgg gttcacctat agataccttg      60
ttttgtaatt cccagccatt taccagatcc cagtattggg taggaactcc cttacaagga     120
aaggcaaagg ttgtattatc aaggctaatt agagagccgg gttgaagttt ttgctttgca     180
accaaacaag ttctttgaga gctgccaagt actcctttta taggggtttc tagatctcgc     240
attggttgac ctaaagcttg ccaacaattg taaattgttt caagagtctt ggctaattga     300
tcaatcccca tagtatgtga tatgtcctga tcgatatctt ctggatagag atgaactcct     360
ttttccagga ttgaagctcc caatgcaata gacatataca acatttcaat tccattataa     420
tggtcagata aaccaactgg taatgaaaaa cattggttta aagttcgtaa cattcttagg     480
ttatgtgctt ctggcaaagc aggatgtcca tcaggactat gttcaataat aatttttttca    540
catccggcac tttttgctgt ttcaactgct ttgcatatat cagttaagga agatcttcca     600
gtgtcaataa tgagcggtaa tcctgttttt gccagatgac gaattaaagg aatatggaca     660
atgttcgatg aagaggtttt gagtgcgcag gccccctgct ttatcgcaaa atcaatagtg     720
tccaattcat aaatcgaaac tatgaagggt aaattggcat tctttaatag tgaaaatagc     780
atactataat gttctaaagg cagtactttt ctctcaatta atgagcggta gttttccttg     840
cgaacctcac ctgatttact ggtataggtt tcttcataat caacaggtag gcaaatgttt     900
gggttattta aaatttctgt ttttagtata agaggttgat acggtatttt atccctgata     960
cttataattt tgtgtagcaa ttgttcagct atgccaagat cctgattaaa aaaagtacct    1020
atttctgcta aaaaaatagg aggatgattt tctccaatag agtaggggcc aatt          1074
```

<210> SEQ ID NO 30
<211> LENGTH: 1074
<212> TYPE: DNA
<213> ORGANISM: Legionella pneumophila

<400> SEQUENCE: 30

```
taacaatcat ttttttgctt aatatccgac catttaatgg gttcacctat agataccttg      60
ttttgtaatt cccagccatt taccagatcc cagtattggg taggaactcc cttacaagga     120
aaggcaaagg ttgtattatc aaggctaatt agagagccgg gttgaagttt ttgctttgca     180
accaaacaag ttctttgaga gctgccaagt actcctttta taggggtttc tagatctcgc     240
attggttgac ctaaagcttg ccaacaattg taaattgttt caagagtctt ggctaattga     300
tcaatcccca tagtatgtga tatgtcctga tcgatatctt ctggatagag atgaactcct     360
ttttccagga ttgaagctcc caatgcaata gacatataca acatttcaat tccattataa     420
tggtcagata aaccaactgg taatgaaaaa cattggttta aagttcgtaa cattcttagg     480
ttatgtgctt ctggcaaagc aggatgtcca tcaggactat gttcaataat aatttttttca    540
catccggcac tttttgctgt ttcaactgct ttgcatatat cagttaagga agatcttcca     600
gtgtcaataa tgagcggtaa tcctgttttt gccagatgac gaattaaagg aatatggaca     660
atgttcgatg aagaggtttt gagtgcgcag gccccctgct ttatcgcaaa atcaatagtg     720
tccaattcat aaatcgaaac tatgaagggt aaattggcat tctttaatag tgaaaatagc     780
atactataat gttctaaagg cagtactttt ctctcaatta atgagcggta gttttccttg     840
cgaacctcac ctgatttact ggtataggtt tcttcataat caacaggtag gcaaatgttt     900
gggttattta aaatttctgt ttttagtata agaggttgat acggtatttt atccctgata     960
```

-continued

```
cttataattt tgtgtagcaa ttgttcagct atgccaagat cctgattaaa aaaagtacct   1020

atttctgcta aaaaaatagg aggatgattt tctccaatag agtaggggcc aatt         1074


<210> SEQ ID NO 31
<211> LENGTH: 1092
<212> TYPE: DNA
<213> ORGANISM: Legionella pneumophila

<400> SEQUENCE: 31

ctaacaatca tttttttgct taatatctga ccatttaatg ggctcaccta tagatacctt     60

gttttgtagt tcccagccat ttaccagatc ccagtattgg gtaggaactc ccttacaagg    120

aaaggcaaag gttgtattat caaggctaat tagagagccg ggttgaagct tttgctttgc    180

aaccaaacaa gttctttgag agctgccaag tactcctttt ataggggttt ctagatctcg    240

catcggttga cctaaagctt gccaacaatt gtaaattgtt tcaagagtct tggctaattg    300

atcaatcccc atagtatgtg atatgtcctg atcaatatct tctggataga gatgaacccc    360

tttttccagg attgaagctc ccaatgcaat agacatatac aacatttcaa ttccattata    420

atggtcagat aatccaactg gtaatgaaaa acattggttt aaagttcgta acattcttaa    480

gttatgtgct tctggcaaag caggatgtcc atcaggacta tgttcaataa taatttttc     540

acatccggca ttttttgctg tttcaactgc tttgcatata tcagttaagg aagatcttcc    600

agtgtcaata ataagcggta atcctgtttt tgccagatga cgaattaaag gaatatggac    660

aatgttcgat gaagaggttt tgagtgcgca ggccccttgc tttattgcaa aatcaatagt    720

gtccaattca taaattgaaa ctatgaaggg taaattggca ttctttaata gtgagaatag    780

catactgtaa tgttctaaag gcagtatttt tctctcaatt aatgagcggt agttttcctt    840

gcgaacctca cctgatttac tagtataggt ttcttcataa tcaacaggta ggcaaatgtt    900

tgggttattt aaaatttctg tttttagtat aagaggttga tacggtactt tatctctgat    960

ggttataatt ttgtgtagca attgttcagc tatgccaaga tcctgattaa aaaaagtacc   1020

tatttctgct aaaaaaatag gaggatgatt ttctccaata gagaatggtc caattgtaaa   1080

aggctgactc at                                                       1092


<210> SEQ ID NO 32
<211> LENGTH: 1092
<212> TYPE: DNA
<213> ORGANISM: Legionella pneumophila

<400> SEQUENCE: 32

ctaacaatca tttttttgct taatatccga ccatttaatg ggttcaccta tagatacctt     60

gttttgtaat tcccagccat ttaccagatc ccagtattgg gtcgggactc ccttacaagg    120

aaaggcaaag gttgtattat caaggctaat tagagagcca ggttgaagtt tttgctttgc    180

aaccaaacaa gttctttgag agctgccaag tactcctttt ataggagctt ctagatctcg    240

catcggttga cctaaagctt gccaacaatt gtaaattgtt tcaagagtct tggctaattg    300

ctcaatcccc atagtatgtg atatgtcctg atcaatatct tctggataga gatgaactcc    360

tttttccagg attgaagctc ccaatgcaat agacatatac aacatttcaa ttccattata    420

atggtcagat aaaccaactg gtaatgaaaa acattggttt aaagttcgta acattcttag    480

gttatgtgct tctggcaaag caggatgtcc atcaggacta tgttcaataa taatttttc     540

acatccggca ctttttgctg tttcaactgc tttgcatata tcagttaaag aagatcttcc    600

agtgtcaata atgagcggta atcctgtttt tgccagatga cgaattaaag gaacatggac    660
```

aatgttcgat gaagaggttt tgagtgcgca ggcaccctgc tttatcgcaa aatcaatagt 720
gtccaattca taaatcgaaa ctatgaaggg taaattggca ttctttaata gtgaaaatag 780
catactataa tgttctaaag gcagtacttt tctctcaatt aatgagcggt agttttcctt 840
gcggacctca ccggatttac tggtataggt ttcttcataa tcaacaggta ggcaaatgtt 900
tgggttattt aaaatttctg tttttagtat aagaggttgg tatggtactt tatccctgat 960
ggttataatt ttgtgtagca attgttcagc tatgccaaga tcctgattaa aaaaagtacc 1020
tatttctgct aaaaaaatag gaggatgatt ttcttcaaca gagaatggac caattgtaaa 1080
aggctgactc at 1092

<210> SEQ ID NO 33
<211> LENGTH: 1092
<212> TYPE: DNA
<213> ORGANISM: Legionella pneumophila

<400> SEQUENCE: 33
ctaacaatca ttttttgct taatatccga ccatttaatg ggttcaccta tagatacctt 60
gttttgtaat tcccagccat ttaccagatc ccagtattgg gtcgggactc ccttacaagg 120
aaaggcaaag gttgtattat caaggctaat tagagagcca ggttgaagtt tttgctttgc 180
aaccaaacaa gttctttgag agctgccaag tactcctttt ataggagctt ctagatctcg 240
catcggttga cctaaagctt gccaacaatt gtaaattgtt tcaagagtct tggctaattg 300
ctcaatcccc atagtatgtg atatgtcctg atcaatatct tctggataga gatgaactcc 360
tttttccagg attgaagctc ccaatgcaat agacatatac aacatttcaa ttccattata 420
atggtcagat aaaccaactg gtaatgaaaa acattggttt aaagttcgta acattcttag 480
gttatgtgct tctggcaaag caggatgtcc atcaggacta tgttcaataa taattttttc 540
acatccggca ctttttgctg tttcaactgc tttgcatata tcagttaaag aagatcttcc 600
agtgtcaata atgagcggta atcctgtttt tgccagatga cgaattaaag gaacatggac 660
aatgttcgat gaagaggttt tgagtgcgca ggcaccctgc tttatcgcaa aatcaatagt 720
gtccaattca taaatcgaaa ctatgaaggg taaattggca ttctttaata gtgaaaatag 780
catactataa tgttctaaag gcagtacttt tctctcaatt aatgagcggt agttttcctt 840
gcggacctca ccggatttac tggtataggt ttcttcataa tcaacaggta ggcaaatgtt 900
tgggttattt aaaatttctg tttttagtat aagaggttgg tatggtactt tatccctgat 960
ggttataatt ttgtgtagca attgttcagc tatgccaaga tcctgattaa aaaaagtacc 1020
tatttctgct aaaaaaatag gaggatgatt ttcttcaaca gagaatggac caattgtaaa 1080
aggctgactc at 1092

<210> SEQ ID NO 34
<211> LENGTH: 1092
<212> TYPE: DNA
<213> ORGANISM: Legionella pneumophila

<400> SEQUENCE: 34
ctaacaatca ttttttgct taatatccga ccatttaatg ggttcaccta tagatacctt 60
gttttgtaat tcccagccat ttaccagatc ccagtattgg gtcgggactc ccttacaagg 120
aaaggcaaag gttgtattat caaggctaat tagagagcca ggttgaagtt tttgctttgc 180
aaccaaacaa gttctttgag agctgccaag tactcctttt ataggagctt ctagatctcg 240

-continued

```
catcggttga cctaaagctt gccaacaatt gtaaattgtt tcaagagtct tggctaattg    300

ctcaatcccc atagtatgtg atatgtcctg atcaatatct tctggataga gatgaactcc    360

tttttccagg attgaagctc ccaatgcaat agacatatac aacatttcaa ttccattata    420

atggtcagat aaaccaactg gtaatgaaaa acattggttt aaagttcgta acattcttag    480

gttatgtgct tctggcaaag caggatgtcc atcaggacta tgttcaataa taattttttc    540

acatccggca ctttttgctg tttcaactgc tttgcatata tcagttaaag aagatcttcc    600

agtgtcaata atgagcggta atcctgtttt tgccagatga cgaattaaag gaacatggac    660

aatgttcgat gaagaggttt tgagtgcgca ggcaccctgc tttatcgcaa aatcaatagt    720

gtccaattca taaatcgaaa ctatgaaggg taaattggca ttctttaata gtgaaaatag    780

catactataa tgttctaaag gcagtacttt tctctcaatt aatgagcggt agttttcctt    840

gcggacctca ccggatttac tggtataggt ttcttcataa tcaacaggta ggcaaatgtt    900

tgggttattt aaaatttctg tttttagtat aagaggttgg tatggtactt tatccctgat    960

ggttataatt ttgtgtagca attgttcagc tatgccaaga tcctgattaa aaaaagtacc   1020

tatttctgct aaaaaaatag gaggatgatt ttcttcaaca gagaatggac caattgtaaa   1080

aggctgactc at                                                       1092
```

<210> SEQ ID NO 35
<211> LENGTH: 1092
<212> TYPE: DNA
<213> ORGANISM: Legionella pneumophila

<400> SEQUENCE: 35

```
ctaacaatca ttttttgct taatatccga ccatttaatg ggttcaccta tagatacctt     60

gttttgtaat tcccagccat ttaccagatc ccagtattgg gtcgggactc ccttacaagg    120

aaaggcaaag gttgtattat caaggctaat tagagagcca ggttgaagtt tttgctttgc    180

aaccaaacaa gttctttgag agctgccaag tactcctttt ataggagctt ctagatctcg    240

catcggttga cctaaagctt gccaacaatt gtaaattgtt tcaagagtct tggctaattg    300

ctcaatcccc atagtatgtg atatgtcctg atcaatatct tctggataga gatgaactcc    360

tttttccagg attgaagctc ccaatgcaat agacatatac aacatttcaa ttccattata    420

atggtcagat aaaccaactg gtaatgaaaa acattggttt aaagttcgta acattcttag    480

gttatgtgct tctggcaaag caggatgtcc atcaggacta tgttcaataa taattttttc    540

acatccggca ctttttgctg tttcaactgc tttgcatata tcagttaaag aagatcttcc    600

agtgtcaata atgagcggta atcctgtttt tgccagatga cgaattaaag gaacatggac    660

aatgttcgat gaagaggttt tgagtgcgca ggcaccctgc tttatcgcaa aatcaatagt    720

gtccaattca taaatcgaaa ctatgaaggg taaattggca ttctttaata gtgaaaatag    780

catactataa tgttctaaag gcagtacttt tctctcaatt aatgagcggt agttttcctt    840

gcggacctca ccggatttac tggtataggt ttcttcataa tcaacaggta ggcaaatgtt    900

tgggttattt aaaatttctg tttttagtat aagaggttgg tatggtactt tatccctgat    960

ggttataatt ttgtgtagca attgttcagc tatgccaaga tcctgattaa aaaaagtacc   1020

tatttctgct aaaaaaatag gaggatgatt ttcttcaaca gagaatggac caattgtaaa   1080

aggctgactc at                                                       1092
```

<210> SEQ ID NO 36
<211> LENGTH: 1060

<212> TYPE: DNA
<213> ORGANISM: Legionella pneumophila

<400> SEQUENCE: 36
atttttttgc ttaatatccg accatttaat gggttcacct atagatacct tgttttgtaa 60
ttcccagcca tttaccagat cccagtattg ggtcgggact cccttacaag gaaaggcaaa 120
ggttgtatta tcaaggctaa ttagagagcc aggttgaagt ttttgctttg caaccaaaca 180
agttctttga gagctgccaa gtactccttt tataggagct tctagatctc gcatcggttg 240
acctaaagct tgccaacaat tgtaaattgt ttcaagagtc ttggctaatt gctcaatccc 300
catagtatgt gatatgtcct gatcaatatc ttctggatag agatgaactc ctttttccag 360
gattgaagct cccaatgcaa tagacatata caacatttca attccattat aatggtcaga 420
taaaccaact ggtaatgaaa aacattggtt taaagttcgt aacattctta ggttatgtgc 480
ttctggcaaa gcaggatgtc catcaggact atgttcaata ataatttttt cacatccggc 540
actttttgct gtttcaactg ctttgcatat atcagttaaa gaagatcttc cagtgtcaat 600
aatgagcggt aatcctgttt ttgccagatg acgaattaaa ggaacatgga caatgttcga 660
tgaagaggtt ttgagtgcgc aggcaccctg ctttatcgca aaatcaatag tgtccaattc 720
ataaatcgaa actatgaagg gtaaattggc attctttaat agtgaaaata gcatactata 780
atgttctaaa ggcagtactt ttctctcaat taatgagcgg tagttttcct tgcggacctc 840
accggattta ctggtatagg tttcttcata atcaacaggt aggcaaatgt ttgggttatt 900
taaaatttct gtttttagta taagaggttg gtatggtact ttatccctga tggttataat 960
tttgtgtagc aattgttcag ctatgccaag atcctgatta aaaaaagtac ctatttctgc 1020
taaaaaaata ggaggatgat tttcttcaac agagaatgga 1060

<210> SEQ ID NO 37
<211> LENGTH: 1060
<212> TYPE: DNA
<213> ORGANISM: Legionella pneumophila

<400> SEQUENCE: 37
atttttttgc ttaatatctg accatttaat gggctcacct atagatacct tgttttgtag 60
ttcccagcca tttaccagat cccagtattg ggtaggaaat cccttacaag gaaaggcaaa 120
ggttgtatta tcaaggctaa ttagagagcc gggttgaagc ttttgctttg caaccaaaca 180
agttctttga gagctgccaa gtactccttt tataggggtt tctagatctc gcatcggttg 240
acctaaagct tgccaacaat tgtaaattgt ttcaagagtc ttggctaatt gatcaatccc 300
catagtatgt gatatgtcct gatcaatatc ttctggatag agatgaaccc ctttttccag 360
gattgaagct cccaatgcaa tagacatata caacatttca attccattat aatggtcaga 420
taatccaact ggtaatgaaa aacattggtt taaagttcgt aacattctta agttatgtgc 480
ttctggcaaa gcaggatgtc catcaggact atgttcaata ataatttttt cacatccggc 540
attttttgct gtttcaactg ctttgcatat atcagttaag gaagatcttc cagtgtcaat 600
aataagcggt aatcctgttt ttgccagatg acgaattaaa ggaatatgga caatgttcga 660
tgaagaggtt ttgagtgcgc aggccccttg ctttattgca aaatcaatag tgtccaattc 720
ataaattgaa actatgaagg gtaaattggc attctttaat agtgagaata gcatactgta 780
atgttctaaa ggcagtattt ttctctcaat taatgagcgg tagttttcct tgcgaacctc 840
acctgattta ctagtatagg tttcttcata atcaacaggt aggcaaatgt ttgggttatt 900
taaaatttct gtttttagta taagaggttg atacggtact ttatctctga tggttataat 960
tttgtgtagc aattgttcag ctatgccaag atcctgatta aaaaaagtac ctatttctgc 1020
taaaaaaata ggaggatgat tttctccaat agagaatggt 1060

<210> SEQ ID NO 38
<211> LENGTH: 1060
<212> TYPE: DNA
<213> ORGANISM: Legionella pneumophila

<400> SEQUENCE: 38 attttttgc ttaatatccg accatttaat gggttcacct atagatacct tgttttgtaa 60
ttcccagcca tttaccagat cccagtattg ggtcgggact cccttacaag gaaaggcaaa 120
ggttgtatta tcaaggctaa ttagagagcc aggttgaagt ttttgctttg caaccaaaca 180
agttctttga gagctgccaa gtactccttt tataggagct tctagatctc gcatcggttg 240
acctaaagct tgccaacaat tgtaaattgt ttcaagagtc ttggctaatt gctcaatccc 300
catagtatgt gatatgtcct gatcaatatc ttctggatag agatgaactc ctttttccag 360
gattgaagct cccaatgcaa tagacatata caacatttca attccattat aatggtcaga 420
taaaccaact ggtaatgaaa aacattggtt taaagttcgt aacattctta ggttatgtgc 480
ttctggcaaa gcaggatgtc catcaggact atgttcaata ataatttttt cacatccggc 540
actttttgct gtttcaactg ctttgcatat atcagttaaa gaagatcttc cagtgtcaat 600
aatgagcggt aatcctgttt ttgccagatg acgaattaaa ggaacatgga caatgttcga 660
tgaagaggtt ttgagtgcgc aggcaccctg ctttatcgca aaatcaatag tgtccaattc 720
ataaatcgaa actatgaagg gtaaattggc attctttaat agtgaaaata gcatactata 780
atgttctaaa ggcagtactt ttctctcaat taatgagcgg tagttttcct tgcggacctc 840
accggattta ctggtatagg tttcttcata atcaacaggt aggcaaatgt ttgggttatt 900
taaaatttct gtttttagta taagaggttg gtatggtact ttatccctga tggttataat 960
tttgtgtagc aattgttcag ctatgccaag atcctgatta aaaaaagtac ctatttctgc 1020
taaaaaaata ggaggatgat tttcttcaac agagaatgga 1060

<210> SEQ ID NO 39
<211> LENGTH: 1060
<212> TYPE: DNA
<213> ORGANISM: Legionella pneumophila

<400> SEQUENCE: 39 attttttgc ttaatatccg accatttaat gggttcacct atagatacct tgttttgtaa 60
ttcccagcca tttaccagat cccagtattg ggtcgggact cccttacaag gaaaggcaaa 120
ggttgtatta tcaaggctaa ttagagagcc aggttgaagt ttttgctttg caaccaaaca 180
agttctttga gagctgccaa gtactccttt tataggagct tctagatctc gcatcggttg 240
acctaaagct tgccaacaat tgtaaattgt ttcaagagtc ttggctaatt gctcaatccc 300
catagtatgt gatatgtcct gatcaatatc ttctggatag agatgaactc ctttttccag 360
gattgaagct cccaatgcaa tagacatata caacatttca attccattat aatggtcaga 420
taaaccaact ggtaatgaaa aacattggtt taaagttcgt aacattctta ggttatgtgc 480
ttctggcaaa gcaggatgtc catcaggact atgttcaata ataatttttt cacatccggc 540
actttttgct gtttcaactg ctttgcatat atcagttaaa gaagatcttc cagtgtcaat 600
aatgagcggt aatcctgttt ttgccagatg acgaattaaa ggaacatgga caatgttcga 660
tgaagaggtt ttgagtgcgc aggcaccctg ctttatcgca aaatcaatag tgtccaattc 720
ataaatcgaa actatgaagg gtaaattggc attctttaat agtgaaaata gcatactata 780
atgttctaaa ggcagtactt ttctctcaat taatgagcgg tagttttcct tgcggacctc 840
accggattta ctggtatagg tttcttcata atcaacaggt aggcaaatgt ttgggttatt 900
taaaatttct gtttttagta taagaggttg gtatggtact ttatccctga tggttataat 960
tttgtgtagc aattgttcag ctatgccaag atcctgatta aaaaaagtac ctatttctgc 1020
taaaaaaata ggaggatgat tttcttcaac agagaatgga 1060

<210> SEQ ID NO 40
<211> LENGTH: 1060
<212> TYPE: DNA
<213> ORGANISM: Legionella pneumophila

<400> SEQUENCE: 40 attttttgc ttaatatccg accatttaat gggttcacct atagatacct tgttttgtaa 60
ttcccagcca tttaccagat cccagtattg ggtcgggact cccttacaag gaaaggcaaa 120
ggttgtatta tcaaggctaa ttagagagcc aggttgaagt ttttgctttg caaccaaaca 180
agttctttga gagctgccaa gtactccttt tataggagct tctagatctc gcatcggttg 240
acctaaagct tgccaacaat tgtaaattgt ttcaagagtc ttggctaatt gctcaatccc 300
catagtatgt gatatgtcct gatcaatatc ttctggatag agatgaactc ctttttccag 360
gattgaagct cccaatgcaa tagacatata caacatttca attccattat aatggtcaga 420
taaaccaact ggtaatgaaa aacattggtt taaagttcgt aacattctta ggttatgtgc 480
ttctggcaaa gcaggatgtc catcaggact atgttcaata ataatttttt cacatccggc 540
actttttgct gtttcaactg ctttgcatat atcagttaaa gaagatcttc cagtgtcaat 600
aatgagcggt aatcctgttt ttgccagatg acgaattaaa ggaacatgga caatgttcga 660
tgaagaggtt ttgagtgcgc aggcaccctg ctttatcgca aaatcaatag tgtccaattc 720
ataaatcgaa actatgaagg gtaaattggc attctttaat agtgaaaata gcatactata 780
atgttctaaa ggcagtactt ttctctcaat taatgagcgg tagttttcct tgcggacctc 840
accggattta ctggtatagg tttcttcata atcaacaggt aggcaaatgt ttgggttatt 900
taaaatttct gtttttagta taagaggttg gtatggtact ttatccctga tggttataat 960
tttgtgtagc aattgttcag ctatgccaag atcctgatta aaaaaagtac ctatttctgc 1020
taaaaaaata ggaggatgat tttcttcaac agagaatgga 1060

<210> SEQ ID NO 41
<211> LENGTH: 1060
<212> TYPE: DNA
<213> ORGANISM: Legionella pneumophila

<400> SEQUENCE: 41 attttttgc ttaatatccg accatttaat gggttcacct atagatacct tgttttgtaa 60
ttcccagcca tttaccagat cccagtattg ggtcgggact cccttacaag gaaaggcaaa 120
ggttgtatta tcaaggctaa ttagagagcc aggttgaagt ttttgctttg caaccaaaca 180
agttctttga gagctgccaa gtactccttt tataggagct tctagatctc gcatcggttg 240
acctaaagct tgccaacaat tgtaaattgt ttcaagagtc ttggctaatt gctcaatccc 300
catagtatgt gatatgtcct gatcaatatc ttctggatag agatgaactc ctttttccag 360

-continued gattgaagct cccaatgcaa tagacatata caacatttca attccattat aatggtcaga 420
taaaccaact ggtaatgaaa aacattggtt taaagttcgt aacattctta ggttatgtgc 480
ttctggcaaa gcaggatgtc catcaggact atgttcaata ataatttttt cacatccggc 540
actttttgct gtttcaactg ctttgcatat atcagttaaa gaagatcttc cagtgtcaat 600
aatgagcggt aatcctgttt ttgccagatg acgaattaaa ggaacatgga caatgttcga 660
tgaagaggtt ttgagtgcgc aggcaccctg ctttatcgca aaatcaatag tgtccaattc 720
ataaatcgaa actatgaagg gtaaattggc attctttaat agtgaaaata gcatactata 780
atgttctaaa ggcagtactt ttctctcaat taatgagcgg tagttttcct tgcggacctc 840
accggattta ctggtatagg tttcttcata atcaacaggt aggcaaatgt ttgggttatt 900
taaaatttct gtttttagta taagaggttg gtatggtact ttatccctga tggttataat 960
tttgtgtagc aattgttcag ctatgccaag atcctgatta aaaaaagtac ctatttctgc 1020
taaaaaaata ggaggatgat tttcttcaac agagaatgga 1060

<210> SEQ ID NO 42
<211> LENGTH: 1060
<212> TYPE: DNA
<213> ORGANISM: Legionella pneumophila

<400> SEQUENCE: 42 attttttgc ttaatatctg accatttaat gggctcacct atagatacct tgttttgtag 60
ttcccagcca tttaccagat cccagtattg ggtaggaaat cccttacaag gaaaggcaaa 120
ggttgtatta tcaaggctaa ttagagagcc gggttgaagc ttttgctttg caaccaaaca 180
agttctttga gagctgccaa gtactccttt tatagggggtt tctagatctc gcatcggttg 240
acctaaagct tgccaacaat tgtaaattgt ttcaagagtc ttggctaatt gatcaatccc 300
catagtatgt gatatgtcct gatcaatatc ttctggatag agatgaaccc ctttttccag 360
gattgaagct cccaatgcaa tagacatata caacatttca attccattat aatggtcaga 420
taatccaact ggtaatgaaa aacattggtt taaagttcgt aacattctta agttatgtgc 480
ttctggcaaa gcaggatgtc catcaggact atgttcaata ataatttttt cacatccggc 540
attttttgct gtttcaactg ctttgcatat atcagttaag gaagatcttc cagtgtcaat 600
aataagcggt aatcctgttt ttgccagatg acgaattaaa ggaatatgga caatgttcga 660
tgaagaggtt ttgagtgcgc aggccccttg ctttattgca aaatcaatag tgtccaattc 720
ataaattgaa actatgaagg gtaaattggc attctttaat agtgagaata gcatactgta 780
atgttctaaa ggcagtattt ttctctcaat taatgagcgg tagttttcct tgcgaacctc 840
acctgattta ctagtatagg tttcttcata atcaacaggt aggcaaatgt ttgggttatt 900
taaaatttct gtttttagta taagaggttg atacggtact ttatctctga tggttataat 960
tttgtgtagc aattgttcag ctatgccaag atcctgatta aaaaaagtac ctatttctgc 1020
taaaaaaata ggaggatgat tttctccaat agagaatggt 1060

<210> SEQ ID NO 43
<211> LENGTH: 1060
<212> TYPE: DNA
<213> ORGANISM: Legionella pneumophila

<400> SEQUENCE: 43 attttttgc ttaatatctg accatttaat gggctcacct atagatacct tgttttgtag 60
ttcccagcca tttaccagat cccagtattg ggtaggaact cccttacaag gaaaggcaaa 120

-continued

```
ggttgtatta tcaaggctaa ttagagagcc gggttgaagc ttttgctttg caaccaaaca    180
agttctttga gagctgccaa gtactccttt tataggggtt tccagatctc gcattggttg    240
acctaaagct tgccaacaat tgtaaattgt ttcaagagtc ttggctaatt gatcaatccc    300
catagtatgt gatatgtcct gatcaatatc ttctggatag agatgaaccc ctttttccag    360
gattgaagct cccaatgcaa tagacatata caacatttca attccattat aatggtcaga    420
taatccaact ggtaatgaaa aacattggtt taaagttcgt aacattctta agttatgtgc    480
ttctggcaaa gcaggatggc catcaggact atgttcaata ataatttttt cacatccggc    540
attttttgct gtttcaactg ctttgcatat atcagttaag gaagatcttc cagtgtcaat    600
aatgagcggt aatcctgttt ttgccagatg acgaattaaa ggaatatgga caatgtttga    660
tgaagaggtt ttgagtgcgc aggccccttg ctttattgca aaatcaatag tgtccaattc    720
ataaattgaa actatgaagg gtaaattggc attctttaat agtgagaata gcatactgta    780
atgttctaaa ggcagtattt ttctctcaat taatgagcgg tagttttcct tgcgaacctc    840
acctgattta ctagtgtagg tttcttcata atcaacaggt aggcaaatgt ttgggttatt    900
taaaatttct gtttttagta taagaggttg atacggtact ttatctctga tggttataat    960
tttgtgtagc aattgttcag ctatgccaag atcctgatta aaaaaagtac ctatttctgc   1020
taaaaaaata ggaggatgat tttctccaat agagaatggt                          1060
```

<210> SEQ ID NO 44
<211> LENGTH: 1060
<212> TYPE: DNA
<213> ORGANISM: Legionella pneumophila

<400> SEQUENCE: 44

```
atttttttgc ttaatatccg accatttaat gggttcacct atagatacct tgttttgtaa     60
ttcccagcca tttaccagat cccagtattg ggtcgggact cccttacaag gaaaggcaaa    120
ggttgtatta tcaaggctaa ttagagagcc aggttgaagt ttttgctttg caaccaaaca    180
agttctttga gagctgccaa gtactccttt tataggagct tctagatctc gcatcggttg    240
acctaaagct tgccaacaat tgtaaattgt ttcaagagtc ttggctaatt gctcaatccc    300
catagtatgt gatatgtcct gatcaatatc ttctggatag agatgaactc ctttttccag    360
gattgaagct cccaatgcaa tagacatata caacatttca attccattat aatggtcaga    420
taaaccaact ggtaatgaaa aacattggtt taaagttcgt aacattctta ggttatgtgc    480
ttctggcaaa gcaggatgtc catcaggact atgttcaata ataatttttt cacatccggc    540
actttttgct gtttcaactg ctttgcatat atcagttaaa gaagatcttc cagtgtcaat    600
aatgagcggt aatcctgttt ttgccagatg acgaattaaa ggaacatgga caatgttcga    660
tgaagaggtt ttgagtgcgc aggcaccctg ctttatcgca aaatcaatag tgtccaattc    720
ataaatcgaa actatgaagg gtaaattggc attctttaat agtgaaaata gcatactata    780
atgttctaaa ggcagtactt ttctctcaat taatgagcgg tagttttcct tgcggacctc    840
accggattta ctggtatagg tttcttcata atcaacaggt aggcaaatgt ttgggttatt    900
taaaatttct gtttttagta taagaggttg gtatggtact ttatccctga tggttataat    960
tttgtgtagc aattgttcag ctatgccaag atcctgatta aaaaaagtac ctatttctgc   1020
taaaaaaata ggaggatgat tttcttcaac agagaatgga                          1060
```

<210> SEQ ID NO 45

<211> LENGTH: 1060
<212> TYPE: DNA
<213> ORGANISM: Legionella pneumophila

<400> SEQUENCE: 45

```
atttttttgc ttaatatccg accatttaat gggttcacct atagatacct tgttttgtaa     60
ttcccagcca tttaccagat cccagtattg ggtaggaact cccttacaag gaaaggcaaa    120
ggttgtatta tcaaggctaa ttagagagcc gggttgaagt ttttgctttg caaccaaaca    180
agttctttga gagctgccaa gtactccttt tataggggtt tctagatctc gcattggttg    240
acctaaagct tgccaacaat tgtaaattgt ttcaagagtc ttggctaatt gatcaatccc    300
catagtatgt gatatgtcct gatcgatatc ttctggatag agatgaactc ctttttccag    360
gattgaagct cccaatgcaa tagacatata caacatttca attccattat aatggtcaga    420
taaaccaact ggtaatgaaa aacattggtt taaagttcgt aacattctta ggttatgtgc    480
ttctggcaaa gcaggatgtc catcagggct atgttcaata ataatttttt cacatccggc    540
actttttgct gtttcaactg ctttgcatat atcagttaag gaagatcttc cagtgtcaat    600
aatgagcggt aatcctgttt ttgccagatg acgaattaaa ggaatatgga caatgttcga    660
tgaagaggtt ttgagtgcgc aggccccctg ctttatcgca aaatcaatag tgtccaattc    720
ataaatcgaa actatgaagg gtaaattggc attctttaat agtgaaaata gcatactata    780
atgttctaaa ggcagtactt ttctctcaat taatgagcgg tagttttcct tgcgaacctc    840
acctgattta ctggtatagg tttcttcata atcaacaggt aggcaaatgt ttgggttatt    900
taaaatttct gtttttagta taagaggttg gtatggtact ttatccctga tggttataat    960
tttgtgtagc aattgttcag ctatgccaag atcctgatta aaaaaagtac ctatttctgc   1020
taaaaaaata ggaggatgat tttcttcaac agagaatgga                         1060
```

<210> SEQ ID NO 46
<211> LENGTH: 1060
<212> TYPE: DNA
<213> ORGANISM: Legionella pneumophila

<400> SEQUENCE: 46

```
atttttttgc ttaatatctg accatttaat gggctcacct atagatacct tgttttgtag     60
ttcccagcca tttaccagat cccagtattg ggtaggaact cccttacaag gaaaggcaaa    120
ggttgtatta tcaaggctaa ttagagagcc gggttgaagc ttttgctttg caaccaaaca    180
agttctttga gagctgccaa gtactccttt tataggggtt tccagatctc gcattggttg    240
acctaaagct tgccaacaat tgtaaattgt ttcaagagtc ttggctaatt gatcaatccc    300
catagtatgt gatatgtcct gatcaatatc ttctggatag agatgaaccc ctttttccag    360
gattgaagct cccaatgcaa tagacatata caacatttca attccattat aatggtcaga    420
taatccaact ggtaatgaaa aacattggtt taaagttcgt aacattctta agttatgtgc    480
ttctggcaaa gcaggatggc catcaggact atgttcaata ataatttttt cacatccggc    540
atttttttgct gtttcaactg ctttgcatat atcagttaag gaagatcttc cagtgtcaat    600
aatgagcggt aatcctgttt ttgccagatg acgaattaaa ggaatatgga caatgtttga    660
tgaagaggtt ttgagtgcgc aggccccttg ctttattgca aaatcaatag tgtccaattc    720
ataaattgaa actatgaagg gtaaattggc attctttaat agtgagaata gcatactgta    780
atgttctaaa ggcagtattt ttctctcaat taatgagcgg tagttttcct tgcgaacctc    840
acctgattta ctagtgtagg tttcttcata atcaacaggt aggcaaatgt ttgggttatt    900
```

-continued

```
taaaatttct gtttttagta taagaggttg atacggtact ttatctctga tggttataat    960

tttgtgtagc aattgttcag ctatgccaag atcctgatta aaaaaagtac ctatttctgc   1020

taaaaaaata ggaggatgat tttctccaat agagaatggt                         1060


<210> SEQ ID NO 47
<211> LENGTH: 1113
<212> TYPE: DNA
<213> ORGANISM: Legionella pneumophila

<400> SEQUENCE: 47

gatagtcaat gagtcagcct tttacaattg gtccattctc tgttgaagaa aatcatcctc     60

ctattttttt agcagaaata ggtacttttt ttaatcagga tcttggcata gctgaacaat    120

tgctacacaa aattataacc atcagggata aagtaccata ccaacctctt atactaaaaa    180

cagaaatttt aaataaccca aacatttgcc tacctgttga ttatgaagaa acctatacca    240

gtaaatccgg tgaggtccgc aaggaaaact accgctcatt aattgagaga aaagtactgc    300

ctttagaaca ttatagtatg ctattttcac tattaaagaa tgccaattta cccttcatag    360

tttcgattta tgaattggac actattgatt ttgcgataaa gcagggtgcc tgcgcactca    420

aaacctcttc atcgaacatt gtccatgttc ctttaattcg tcatctggca aaaacaggat    480

taccgctcat tattgacact ggaagatctt ctttaactga tatatgcaaa gcagttgaaa    540

cagcaaaaag tgccggatgt gaaaaaatta ttattgaaca tagtcctgat ggacatcctg    600

ctttgccaga agcacataac ctaagaatgt tacgaacttt aaaccaatgt ttttcattac    660

cagttggttt atctgaccat tataatggaa ttgaaatgtt gtatatgtct attgcattgg    720

gagcttcaat cctggaaaaa ggagttcatc tctatccaga agatattgat caggacatat    780

cacatactat ggggattgag caattagcca agactcttga aacaatttac aattgttggc    840

aagctttagg tcaaccgatg cgagatctag aagctcctat aaaaggagta cttggcagct    900

ctcaaagaac ttgtttggtt gcaaagcaaa aacttcaacc tggctctcta attagccttg    960

ataatacaac ctttgccttt ccttgtaagg gagtcccgac ccaatactgg gatctggtaa   1020

atggctggga attacaaaac aaggtatcta taggtgaacc cattaaatgg tcggatatta   1080

agcaaaaaaa tgattgttag aaaccctact tgg                                1113


<210> SEQ ID NO 48
<211> LENGTH: 1113
<212> TYPE: DNA
<213> ORGANISM: Legionella pneumophila

<400> SEQUENCE: 48

gatagtcaat gagtcagcct tttacaattg gtccattctc tgttgaagaa aatcatcctc     60

ctattttttt agcagaaata ggtacttttt ttaatcagga tcttggcata gctgaacaat    120

tgctacacaa aattataacc atcagggata aagtaccata ccaacctctt atactaaaaa    180

cagaaatttt aaataaccca aacatttgcc tacctgttga ttatgaagaa acctatacca    240

gtaaatccgg tgaggtccgc aaggaaaact accgctcatt aattgagaga aaagtactgc    300

ctttagaaca ttatagtatg ctattttcac tattaaagaa tgccaattta cccttcatag    360

tttcgattta tgaattggac actattgatt ttgcgataaa gcagggtgcc tgcgcactca    420

aaacctcttc atcgaacatt gtccatgttc ctttaattcg tcatctggca aaaacaggat    480

taccgctcat tattgacact ggaagatctt ctttaactga tatatgcaaa gcagttgaaa    540
```

-continued

```
cagcaaaaag tgccggatgt gaaaaaatta ttattgaaca tagtcctgat ggacatcctg    600

ctttgccaga agcacataac ctaagaatgt tacgaacttt aaaccaatgt ttttcattac    660

cagttggttt atctgaccat tataatggaa ttgaaatgtt gtatatgtct attgcattgg    720

gagcttcaat cctggaaaaa ggagttcatc tctatccaga agatattgat caggacatat    780

cacatactat ggggattgag caattagcca agactcttga aacaatttac aattgttggc    840

aagctttagg tcaaccgatg cgagatctag aagctcctat aaaaggagta cttggcagct    900

ctcaaagaac ttgtttggtt gcaaagcaaa aacttcaacc tggctctcta attagccttg    960

ataatacaac ctttgccttt ccttgtaagg gagtcccgac ccaatactgg gatctggtaa   1020

atggctggga attacaaaac aaggtatcta taggtgaacc cattaaatgg tcggatatta   1080

agcaaaaaaa tgattgttag aaaccctact tgg                                1113


<210> SEQ ID NO 49
<211> LENGTH: 18
<212> TYPE: DNA
<213> ORGANISM: Unknown
<220> FEATURE:
<223> OTHER INFORMATION: Synthetic oligonucleotide

<400> SEQUENCE: 49

gatcaatacg aagcaggc                                                   18


<210> SEQ ID NO 50
<211> LENGTH: 20
<212> TYPE: DNA
<213> ORGANISM: Unknown
<220> FEATURE:
<223> OTHER INFORMATION: Synthetic oligonucleotide

<400> SEQUENCE: 50

ccttgycttt caacacttcc                                                 20


<210> SEQ ID NO 51
<211> LENGTH: 25
<212> TYPE: DNA
<213> ORGANISM: Unknown
<220> FEATURE:
<223> OTHER INFORMATION: Synthetic oligonucleotide

<400> SEQUENCE: 51

catccactca ttttattcct gatcc                                           25


<210> SEQ ID NO 52
<211> LENGTH: 25
<212> TYPE: DNA
<213> ORGANISM: Unknown
<220> FEATURE:
<223> OTHER INFORMATION: Synthetic oligonucleotide

<400> SEQUENCE: 52

catctactca ttttattcct gatcc                                           25
```

METHOD FOR THE DETECTION OF LEGIONELLA

CROSS-REFERENCE TO RELATED APPLICATIONS

This application claims priority to, and the benefit of, International Application Number PCT/EP2017/075265, filed Oct. 4, 2017, and EP Application EP16192489.9, filed Oct. 5, 2016. The contents of both applications are incorporated herein by reference for all purposes.

FIELD OF THE INVENTION

This invention relates to the detection of *Legionella*, more specifically *Legionella pneumophila*, more specifically *Legionella pneumophila* serogroup 1, in a sample. Methods of detection, and assays and kits useful for detection are also disclosed.

BACKGROUND OF THE INVENTION

Infections acquired in buildings, hospitals, and healthcare institutions affect approximately 2 million people, result in approximately 98,000 deaths, and cost a reported USD29 billion in the United States alone each year. The economic burden of infections acquired in hospitals in Europe is estimated to be €7 billion per annum.

Water, water distribution, and premise plumbing systems have been identified as a source of many of these infections, and can pose a significant threat to human health, especially in patients with weakened immune systems, and high dependency patients in critical care units. As infection control and prevention teams within clinical settings increasingly recognise the risks to patient health, a variety of testing and treatment technologies are being employed to attempt to eradicate pathogenic microorganisms from water. Despite the range of technologies being applied, the problem of waterborne infection, particularly from *Legionella* species, in the healthcare setting continues to persist.

Legionnaires' disease was first recognised in 1976 during an outbreak of pneumonia at an American Legion convention in Philadelphia. *Legionella* spp., the causative agent of Legionnaires disease, are responsible for outbreaks of both hospital acquired and community acquired pneumonia. In healthcare settings, there are increasing proportions of immunologically compromised patients leading to added potential for infection of patients by such opportunistic pathogenic microorganisms. The most common microorganism associated with Legionnaires disease is *Legionella pneumophila. L. pneumophila* serogroup 1 is the most clinically relevant. Currently, routine testing for *L. pneumophila* serogroup 1 is performed using traditional microbiological based techniques. This method is limited by the fastidious nature and long incubation periods required by *Legionella* spp. and also by the presence of viable but non-culturable Legionellae.

Prior art gold standard, culture-based methodologies are centuries old and are slow to deliver a result for *Legionella*, taking up to 2 weeks. Furthermore, prior art culture-based methodologies alone cannot specifically identify if *L. pneumophila* serogroup 1 is present in a sample. Serogroup 1 is the most important serogroup from a human health perspective, as it causes ~95% of infections. There are also a number of prior art biochemical and immunodetection-based kits for these microorganisms. However, they are not very sensitive and are not truly quantitative.

SUMMARY OF THE INVENTION

According to the present invention, there is provided a method for identifying the presence, absence, or quantity of *Legionella pneumophila* serogroup 1 in a sample, the method comprising the steps of:

(a) detecting the presence, absence, or quantity of at least part of the nucleic acid sequence of the lpg0768 gene, or an expression product thereof; and (b) correlating the presence, absence, or quantity of the at least part of the nucleic acid sequence of the lpg0768 gene or expression product thereof to the presence, absence, or quantity of *Legionella pneumophila* serogroup 1 in the sample.

Optionally, the method further comprises the steps of:

(ai) detecting the presence, absence, or quantity of at least part of the nucleic acid sequence of the smpB gene, or an expression product thereof; and correlating the presence, absence, or quantity of the at least part of the nucleic acid sequence of the smpB gene or expression product thereof to the presence, absence, or quantity of *Legionella pneumophila* in the sample.

Optionally or additionally, the method further comprises the steps of:

(aii) detecting the presence, absence, or quantity of at least part of the nucleic acid sequence of the ssrA gene, or an expression product thereof; and correlating the presence, absence, or quantity of the at least part of the nucleic acid sequence of the ssrA gene or expression product thereof to the presence, absence, or quantity of *Legionella* genus in the sample.

Optionally, the method comprises the steps of:

(a) detecting the presence, absence, or quantity of at least part of the nucleic acid sequence of the lpg0768 gene or an expression product thereof;

(ai) detecting the presence, absence, or quantity of at least part of the nucleic acid sequence of the smpB gene or an expression product thereof;

(b) correlating the presence, absence, or quantity of the at least part of the nucleic acid sequence of the lpg0768 gene or expression product thereof to the presence, absence, or quantity of *Legionella pneumophila* serogroup 1 in the sample; and correlating the presence, absence, or quantity of the at least part of the nucleic acid sequence of the smpB gene or expression product thereof to the presence, absence, or quantity of *Legionella pneumophila* in the sample.

Optionally, the method comprises the steps of:

(a) detecting the presence, absence, or quantity of at least part of the nucleic acid sequence of the lpg0768 gene or an expression product thereof;

(aii) detecting the presence, absence, or quantity of at least part of the nucleic acid sequence of the ssrA gene or an expression product thereof;

(b) correlating the presence, absence, or quantity of the at least part the lpg0768 gene or expression product thereof to the presence, absence, or quantity of *Legionella pneumophila* serogroup 1 in the sample; and correlating the presence, absence, or quantity of the at least part of the nucleic acid sequence of the ssrA gene or expression product thereof to the presence, absence, or quantity of *Legionella* genus in the sample.

Optionally, the method comprising the steps of:

(a) detecting the presence, absence, or quantity of at least part of the nucleic acid sequence of the lpg0768 gene or an expression product thereof;

(ai) detecting the presence, absence, or quantity of at least part of the nucleic acid sequence of the smpB gene or an expression product thereof;

(aii) detecting the presence, absence, or quantity of at least part of the nucleic acid sequence of the ssrA gene or an expression product thereof;

(b) correlating the presence, absence, or quantity of the at least part of the nucleic acid sequence the lpg0768 gene or expression product thereof to the presence, absence, or quantity of *Legionella pneumophila* serogroup 1 in the sample; correlating the presence, absence, or quantity of the at least part of the nucleic acid sequence of the smpB gene or expression product thereof to the presence, absence, or quantity of *Legionella pneumophila* in the sample; and correlating the presence, absence, or quantity of the at least part of the nucleic acid sequence of the ssrA gene or expression product thereof to the presence, absence, or quantity of *Legionella* genus in the sample.

Optionally, the presence of the at least part of the nucleic acid sequence of the lpg0768 gene or an expression product thereof indicates the presence of *Legionella pneumophila* serogroup 1.

Optionally, the absence of the at least part of the nucleic acid sequence of the lpg0768 gene or an expression product thereof indicates the absence of *Legionella pneumophila* serogroup 1.

Optionally, the quantity of the at least part of the nucleic acid sequence of the lpg0768 gene or an expression product thereof indicates the quantity of *Legionella pneumophila* serogroup 1.

Optionally, the at least part of the nucleic acid sequence of the lpg0768 gene comprises at least part of the nucleic acid sequence which encodes spore coat polysaccharide biosynthesis protein E (neuB).

Optionally, the at least part of the nucleic acid sequence of the lpg0768 gene comprises at least part of the nucleic acid sequence defined by Genbank Accession Number AE017354; base pairs 839972 to 840171.

Optionally, the at least part of the nucleic acid sequence of the lpg0768 gene comprises a nucleic acid sequence having at least 85% sequence identity with at least part of the nucleic acid sequence defined by any one of SEQ ID NOs 1 and 21-48.

Optionally, the at least part of the nucleic acid sequence of the lpg0768 gene comprises a nucleic acid sequence having at least 85%, 87.5%, 88%, 88.5%, 94%, 94.5%, 95%, or 100% sequence identity with at least part of the nucleic acid sequence defined by any one of SEQ ID NOs 1 and 21-48.

Optionally, the at least part of the nucleic acid sequence of the lpg0768 gene comprises a nucleic acid sequence defined by any one of SEQ ID NOs 1 and 21-48.

Optionally, the detecting step (a) comprises: contacting the sample with at least one primer capable of hybridizing to at least part of the at least part of the nucleic acid sequence of the lpg0768 gene, optionally at least part of the nucleic acid sequence defined by any one of SEQ ID NOs 1 and 21-48; under conditions suitable for an in vitro amplification, optionally an in vitro amplification selected from the group comprising: polymerase chain reaction (PCR), Nucleic Acid Sequence Based Amplification (NASBA), Rolling Circle Amplification (RCA), Ligase Chain Reaction (LCR), Signal Mediated Amplification of RNA Technology (SMART), Strand Displacement Amplification (SDA), Loop Mediated Isothermal Amplification (LAMP), Isothermal Multiple Displacement Amplification (IMDA), Helicase-Dependent Amplification (HDA), Single Primer Isothermal Amplification (SIPA), circular Helicase Dependent Amplification (cHDA), and Next Generation Sequencing (NGS).

Optionally, polymerase chain reaction (PCR) is selected from real-time PCR and quantitative real-time PCR.

Optionally, the polymerase chain reaction (PCR), optionally the real-time PCR, optionally the quantitative real-time PCR, further comprises pyrosequencing.

Optionally, the detecting step (a) comprises: contacting the sample with at least one primer having a nucleic acid sequence defined by at least one of SEQ ID NO. 2, SEQ ID NO. 3, and the reverse complement each thereof; under conditions suitable for an in vitro amplification, optionally an in vitro amplification selected from the group comprising: polymerase chain reaction (PCR), Nucleic Acid Sequence Based Amplification (NASBA), Rolling Circle Amplification (RCA), Ligase Chain Reaction (LCR), Signal Mediated Amplification of RNA Technology (SMART), Strand Displacement Amplification (SDA), Loop Mediated Isothermal Amplification (LAMP), Isothermal Multiple Displacement Amplification (IMDA), Helicase-Dependent Amplification (HDA), Single Primer Isothermal Amplification (SIPA), circular Helicase Dependent Amplification (cHDA), and Next Generation Sequencing (NGS).

Optionally, polymerase chain reaction (PCR) is selected from real-time PCR and quantitative real-time PCR.

Optionally, the polymerase chain reaction (PCR), optionally the real-time PCR, optionally the quantitative real-time PCR, further comprises pyrosequencing.

Optionally, the at least one primer has a final concentration of about 0.05-0.5 μM, optionally 0.05 μM, optionally 0.5 μM.

Optionally, the detecting step (a) comprises: contacting the sample with at least one probe capable of hybridizing to at least part of the at least part of the lpg0768 gene, optionally at least part of the nucleic acid sequence defined by any one of SEQ ID NOs 1 and 21-48, under conditions suitable for hybridization.

Optionally, the detecting step (a) comprises: contacting the sample with at least one probe having a nucleic acid sequence defined by at least one of SEQ ID NO. 4 and the reverse complement thereof, under conditions suitable for hybridisation.

Optionally, the at least one probe comprises at least one marker, optionally at least one dye, optionally at least one fluorophore, optionally hexachlorofluorescein.

Optionally or additionally, the at least one probe comprises at least one fluorescence quenching dye.

Optionally the polymerase chain reaction, or real-time PCR, or quantitative real-time PCR, cycling parameters comprise about 10 minutes incubation at about 95° C., optionally or additionally about 50 cycles of about 95° C. for about 10 seconds and about 60° C. for about 30 seconds, optionally or additionally followed by a cooling step at about 40° C. for about 10 seconds.

Optionally, the at least one probe has a final concentration of about 0.02-0.8 μM, optionally 0.02 μM, optionally 0.08 μM, optionally 0.2 μM, optionally 0.8 μM.

Optionally, the presence of the at least part of the nucleic acid sequence of the smpB gene or expression product thereof indicates the presence of *Legionella pneumophila*.

Optionally, the absence of the at least part of the nucleic acid sequence of the smpB gene or expression product thereof indicates the absence of *Legionella pneumophila*.

Optionally, the presence of the at least part of the nucleic acid sequence of the smpB gene or expression product thereof, and the presence of the at least part of the nucleic acid sequence of the lpg0768 gene or expression product thereof, indicates the presence of each of *Legionella pneumophila* serogroup 1 and *Legionella pneumophila*.

Optionally, the presence of the at least part of the nucleic acid sequence of the smpB gene or expression product thereof, and the absence of the at least part of the nucleic acid sequence of the lpg0768 gene or expression product thereof, indicates the presence of *Legionella pneumophila* and the absence of *Legionella pneumophila* serogroup 1.

Optionally, the presence of the at least part of the nucleic acid sequence of the smpB gene or expression product thereof, and the absence of the at least part of the nucleic acid sequence of the lpg0768 gene or an expression product thereof, indicates the presence of at least one organism selected from *Legionella pneumophila* serogroups 2-16.

Optionally, the absence of the at least part of the nucleic acid sequence of the smpB gene or expression product thereof, and the presence of the at least part of the lpg0768 gene, or expression product thereof, indicates at least one false result selected from: a false negative result in detecting step (ai), and a false positive result in detecting step (a).

Optionally, the absence of the at least part of the nucleic acid sequence of the smpB gene or expression product thereof, and the absence of the at least part of the nucleic acid sequence of the lpg0768 gene or expression product thereof, indicates the absence of each of *Legionella pneumophila* and *Legionella pneumophila* serogroup 1.

Optionally, the at least part of the nucleic acid sequence of the smpB gene comprises at least part of the nucleic acid sequence which encodes small protein B (smpB).

Optionally, the at least part of the nucleic acid sequence of the smpB gene comprises at least part of the nucleic acid sequence defined by Genbank Accession number AE017354; base pairs 3213961 to 3214076.

Optionally, the at least part of the nucleic acid sequence of the smpB gene comprises at least part of the nucleic acid sequence defined by SEQ ID NO. 6.

Optionally, the detecting step (ai) comprises: contacting the sample with at least one primer capable of hybridizing to at least part of the nucleic acid sequence of the smpB gene, optionally at least part of the nucleic acid sequence defined by SEQ ID NO. 6, under conditions suitable for an in vitro amplification, optionally an in vitro amplification selected from the group comprising: polymerase chain reaction (PCR), Nucleic Acid Sequence Based Amplification (NASBA), Rolling Circle Amplification (RCA), Ligase Chain Reaction (LCR), Signal Mediated Amplification of RNA Technology (SMART), Strand Displacement Amplification (SDA), Loop Mediated Isothermal Amplification (LAMP), Isothermal Multiple Displacement Amplification (IMDA), Helicase-Dependent Amplification (HDA), Single Primer Isothermal Amplification (SIPA), circular Helicase Dependent Amplification (cHDA), and Next Generation Sequencing (NGS).

Optionally, polymerase chain reaction (PCR) is selected from real-time PCR and quantitative real-time PCR.

Optionally, the polymerase chain reaction (PCR), optionally the real-time PCR, optionally the quantitative real-time PCR, further comprises pyrosequencing.

Optionally, the detecting step (ai) comprises: contacting the sample with at least one primer having a nucleic acid sequence defined by at least one of SEQ ID NO. 7, SEQ ID NO. 8, SEQ ID NO. 13, and the reverse complement each thereof, under conditions suitable for an in vitro amplification, optionally an in vitro amplification selected from the group comprising: polymerase chain reaction (PCR), Nucleic Acid Sequence Based Amplification (NASBA), Rolling Circle Amplification (RCA), Ligase Chain Reaction (LCR), Signal Mediated Amplification of RNA Technology (SMART), Strand Displacement Amplification (SDA), Loop Mediated Isothermal Amplification (LAMP), Isothermal Multiple Displacement Amplification (IMDA), Helicase-Dependent Amplification (HDA), Single Primer Isothermal Amplification (SIPA), circular Helicase Dependent Amplification (cHDA), and Next Generation Sequencing (NGS).

Optionally, the detecting step (ai) comprises: contacting the sample with at least one primer having a nucleic acid sequence defined by at least one of SEQ ID NO. 7, SEQ ID NO. 8, SEQ ID NO. 13, SEQ ID NO. 49, SEQ ID NO. 50, and the reverse complement each thereof, under conditions suitable for an in vitro amplification, optionally an in vitro amplification selected from the group comprising: polymerase chain reaction (PCR), Nucleic Acid Sequence Based Amplification (NASBA), Rolling Circle Amplification (RCA), Ligase Chain Reaction (LCR), Signal Mediated Amplification of RNA Technology (SMART), Strand Displacement Amplification (SDA), Loop Mediated Isothermal Amplification (LAMP), Isothermal Multiple Displacement Amplification (IMDA), Helicase-Dependent Amplification (HDA), Single Primer Isothermal Amplification (SIPA), circular Helicase Dependent Amplification (cHDA), and Next Generation Sequencing (NGS).

Optionally, polymerase chain reaction (PCR) is selected from real-time PCR and quantitative real-time PCR.

Optionally, the polymerase chain reaction (PCR), optionally the real-time PCR, optionally the quantitative real-time PCR, further comprises pyrosequencing.

Optionally, the at least one primer has a final concentration of about 0.05-0.5 μM, optionally 0.05 μM, optionally 0.5 μM.

Optionally the polymerase chain reaction, or real-time PCR, or quantitative real-time PCR, cycling parameters comprise about 5 minutes incubation at about 95° C., optionally or additionally 50 cycles at about 95° C. for about 10 seconds and about 60° C. for about 30 seconds, optionally or additionally followed by a cooling step at about 40° C. for about 10 seconds.

Optionally, the detecting step (ai) comprises: contacting the sample with at least one probe capable of hybridizing to at least part of the nucleic acid sequence of the smpB gene, optionally at least part of the nucleic acid sequence defined by SEQ ID NO. 6, under conditions suitable for hybridisation.

Optionally, the detecting step (ai) comprises: contacting the sample with at least one probe having a nucleic acid sequence defined by at least one of SEQ ID NO. 9 or the reverse complement thereof, under conditions suitable for hybridisation.

Optionally, the detecting step (ai) comprises: contacting the sample with at least one probe having a nucleic acid sequence defined by at least one of SEQ ID NO. 9, SEQ ID NO 51, SEQ ID NO. 52, and the reverse complement each thereof, under conditions suitable for hybridisation.

Optionally, the at least one probe comprises at least one marker, optionally at least one dye, optionally at least one fluorophore, optionally rhodamine.

Optionally, or additionally, the at least one probe comprises at least one fluorescence quenching dye.

Optionally, the at least one probe has a final concentration of about 0.02-0.8 μM, optionally 0.02 μM, optionally 0.08 μM, optionally 0.2 μM, optionally 0.8 μM.

Optionally, the presence of the at least part of the nucleic acid sequence of the ssrA gene or expression product thereof indicates the presence of *Legionella* genus.

Optionally, the absence of the at least part of the nucleic acid sequence of the ssrA gene or expression product thereof indicates the absence of *Legionella* genus.

Optionally, the presence of the at least part of the nucleic acid sequence of the ssrA gene or expression product thereof, and the presence of the at least part of the lpg0768 gene or expression product thereof, indicates the presence of each of the *Legionella* genus and *Legionella pneumophila* serogroup 1.

Optionally, the presence of the at least part of the nucleic acid sequence of the ssrA gene or expression product thereof, and the absence of the at least part of the nucleic acid sequence of the lpg0768 gene or expression product thereof, indicates the presence of the *Legionella* genus and the absence of *Legionella pneumophila* serogroup 1.

Optionally, the presence of the at least part of the nucleic acid sequence of the ssrA gene or expression product thereof, and the absence of the at least part of the nucleic acid sequence of the lpg0768 gene or expression product thereof, indicates the presence of at least one organism selected from *Legionella pneumophila* serogroups 2-16, *Legionella anisa, L. birminghamensis, L. birminghamensis, L. bozemanii, L. bozemanii, L. cincinnatiensis, L. dumoffii, L. dumoffii, L. erythra, L. feeleii*-1, *L. feelii*-2, *L. gormanii, L. gormanii, L. hackeliae*-1, *L. hackeliae*-2, *L. jordanis, L. jordanis, L. lansingensis, L. longbeachae*-1, *L. maceachemii, L. miodadei, L. oakridgensis, L. oakridgensis, L. parisiensis, L. wadworthii, L. cherrii, L. jamestowniensis, L. londoniensis, L. taurinsis, L. moravica, L. adelaidensis, L. donaldsonii, L. gratiana, L. gresilensis, L. fairfieldensis, L. israelensis, L. fallonii, L. brunensis, L. busanensis, L. quinlivanii*, and *L. rubrilicens* or other non-*Legionella pneumophila* species Optionally, the absence of the at least part of the nucleic acid sequence of the ssrA gene or expression product thereof, and the presence of the at least part of the nucleic acid sequence of the lpg0768 gene or expression product thereof, indicates at least one false result selected from: a false negative result in detecting step (aii), and a false positive result in detecting step (a).

Optionally, the absence of the at least part of the nucleic acid sequence of the ssrA gene or expression product thereof, and the absence of the at least part of the nucleic acid sequence of the lpg0768 gene or expression product thereof, indicates the absence of each of the *Legionella* genus and *Legionella pneumophila* serogroup 1.

Optionally, the presence of the at least part of the nucleic acid sequence of the ssrA gene or expression product thereof, and the presence of the at least part of the nucleic acid sequence of the smpB gene or expression product thereof, and the presence of the at least part of the nucleic acid sequence of the lpg0768 gene or expression product thereof, indicates the presence of each of the *Legionella* genus, *Legionella pneumophila*, and *Legionella pneumophila* serogroup 1.

Optionally, the presence of the at least part of the nucleic acid sequence of the ssrA gene or expression product thereof, and the presence of the at least part of the nucleic acid sequence of the smpB gene or expression product thereof, and the absence of the at least part of the nucleic acid sequence of the lpg0768 gene or an expression product thereof, indicates the presence of *Legionella* genus and *Legionella pneumophila*, and the absence of *Legionella pneumophila* serogroup 1.

Optionally, the presence of the at least part of the nucleic acid sequence of the ssrA gene or expression product thereof, and the presence of the at least part of the nucleic acid sequence of the smpB gene or expression product thereof, and the absence of the at least part of the nucleic acid sequence of the lpg0768 gene or expression product thereof, indicates the presence of the *Legionella* genus and at least one organism selected from *Legionella pneumophila* serogroup 2-16.

Optionally, the presence of the at least part of the nucleic acid sequence of the ssrA gene or expression product thereof, and the absence of the at least part of the nucleic acid sequence of the smpB gene or expression product thereof, and the presence of the at least part of the lpg0768 gene or expression product thereof, indicates the presence of the *Legionella* genus, and also indicates at least one false result selected from: a false negative result in detecting step (ai), a false positive result in detecting step (a).

Optionally, the presence of the at least part of the nucleic acid sequence of the ssrA gene or expression product thereof, and the absence of the at least part of the nucleic acid sequence of the smpB gene or expression product thereof, and the presence of the at least part of the nucleic acid sequence of the lpg0768 gene or expression product thereof, indicates the presence of at least one organism selected from *Legionella anisa, L. birminghamensis, L. birminghamensis, L. bozemanii, L. bozemanii, L. cincinnatiensis, L. dumoffii, L. dumoffii, L. erythra, L. feeleii*-1, *L. feelii*-2, *L. gormanii, L. gormanii, L. hackeliae*-1, *L. hackeliae*-2, *L. jordanis, L. jordanis, L. lansingensis, L. longbeachae*-1, *L. maceachemii, L. miodadei, L. oakridgensis, L. oakridgensis, L. parisiensis, L. wadworthii, L. cherrii, L. jamestowniensis, L. londoniensis, L. taurinsis, L. moravica, L. adelaidensis, L. donaldsonii, L. gratiana, L. gresilensis, L. fairfieldensis, L. israelensis, L. fallonii, L. brunensis, L. busanensis, L. quinlivanii, L. rubrilicens*, or other non-*Legionella pneumophila* species, and also indicates at least one false result selected from: a false negative result in detecting step (ai), a false positive result in detecting step (a).

Optionally, the presence of the at least part of the nucleic acid sequence of the ssrA gene or expression product thereof, and the absence of the at least part of the nucleic acid sequence of the smpB gene or expression product thereof, and the absence of the at least part of the nucleic acid sequence of the lpg0768 gene or expression product thereof, indicates the presence of at least one organism selected from the *Legionella* genus, and the absence of each of *Legionella pneumophila* species and *Legionella pneumophila* serogroup 1.

Optionally, the presence of the at least part of the nucleic acid sequence of the ssrA gene or expression product thereof, and the absence of the at least part of the nucleic acid sequence of the smpB gene or expression product thereof, and the absence of the at least part of the nucleic acid sequence of the lpg0768 gene or expression product thereof, indicates the presence of at least one organism selected from *Legionella anisa, L. birminghamensis, L. birminghamensis, L. bozemanii, L. bozemanii, L. cincinnatiensis, L. dumoffii, L. dumoffii, L. erythra, L. feeleii*-1, *L. feelii*-2, *L. gormanii, L. gormanii, L. hackeliae*-1, *L. hackeliae*-2, *L. jordanis, L. jordanis, L. lansingensis, L. longbeachae*-1, *L. maceachemii, L. miodadei, L. oakridgensis, L. oakridgensis, L. parisiensis, L. wadworthii, L. cherrii, L.*

*jamestowniensis, L. londoniensis, L. taurinsis, L. moravica, L. adelaidensis, L. donaldsonii, L. gratiana, L. gresilensis, L. fairfieldensis, L. israelensis, L. fallonii, L. brunensis, L. busanensis, L. quinlivanii, L. rubrilicens*, or other non-*Legionella pneumophila* species, and the absence of *Legionella pneumophila* species or *Legionella pneumophila* serogroup 1.

Optionally, the absence of the at least part of the nucleic acid sequence of the ssrA gene or expression product thereof, the presence of the at least part of the nucleic acid sequence of the smpB gene or expression product thereof, and the presence of the at least part of the nucleic acid sequence of the lpg0768 gene or expression product thereof, indicates at least one false result selected from: a false negative result in detecting step (aii), a false positive result in detecting step (ai), and a false positive result in detecting step (a).

Optionally, the absence of the at least part of the nucleic acid sequence of the ssrA gene or expression product thereof, the presence of the at least part of the nucleic acid sequence of the smpB gene or expression product thereof, and the absence of the at least part of the nucleic acid sequence of the lpg0768 gene or expression product thereof, indicates at least one false result selected from: a false negative result in detecting step (aii), a false positive result in detecting step (ai), and a false negative result in detecting step (a).

Optionally, the absence of the at least part of the nucleic acid sequence of the ssrA gene or expression product thereof, the absence of the at least part of the nucleic acid sequence of the smpB gene or expression product thereof, and the absence of the at least part of the nucleic acid sequence of the lpg0768 gene or expression product thereof, indicates the absence of each of the *Legionella* genus, *Legionella pneumophila* species, and *Legionella pneumophila* serogroup 1.

Optionally, the at least part of the nucleic acid sequence of the ssrA gene comprises at least part of the nucleic acid sequence defined by Genbank Accession number AE017354; base pairs 172917 to 173144.

Optionally, the at least part of the nucleic acid sequence of the ssrA gene comprises at least part of the nucleic acid sequence defined by SEQ ID NO. 5.

Optionally, the detecting step (aii) comprises: contacting the sample with at least one primer capable of hybridizing to at least part of the nucleic acid sequence of the ssrA gene, optionally at least part of the nucleic acid sequence defined by SEQ ID NO. 5, under conditions suitable for an in vitro amplification, optionally an in vitro amplification selected from the group comprising: polymerase chain reaction (PCR), Nucleic Acid Sequence Based Amplification (NASBA), Rolling Circle Amplification (RCA), Ligase Chain Reaction (LCR), Signal Mediated Amplification of RNA Technology (SMART), Strand Displacement Amplification (SDA), Loop Mediated Isothermal Amplification (LAMP), Isothermal Multiple Displacement Amplification (IMDA), Helicase-Dependent Amplification (HDA), Single Primer Isothermal Amplification (SIPA), circular Helicase Dependent Amplification (cHDA), and Next Generation Sequencing (NGS).

Optionally, polymerase chain reaction (PCR) is selected from real-time PCR and quantitative real-time PCR.

Optionally, the polymerase chain reaction (PCR), optionally the real-time PCR, optionally the quantitative real-time PCR, further comprises pyrosequencing.

Optionally, the detecting step (aii) comprises: contacting the sample with at least one primer having a nucleic acid sequence defined by at least one of SEQ ID NO. 10, SEQ ID NO. 11, and the reverse complement each thereof, under conditions suitable for an in vitro amplification, optionally an in vitro amplification selected from the group comprising: polymerase chain reaction (PCR), Nucleic Acid Sequence Based Amplification (NASBA), Rolling Circle Amplification (RCA), Ligase Chain Reaction (LCR), Signal Mediated Amplification of RNA Technology (SMART), Strand Displacement Amplification (SDA), Loop Mediated Isothermal Amplification (LAMP), Isothermal Multiple Displacement Amplification (IMDA), Helicase-Dependent Amplification (HDA), Single Primer Isothermal Amplification (SIPA), circular Helicase Dependent Amplification (cHDA), and Next Generation Sequencing (NGS).

Optionally, polymerase chain reaction (PCR) is selected from real-time PCR and quantitative real-time PCR.

Optionally, the polymerase chain reaction (PCR), optionally the real-time PCR, optionally the quantitative real-time PCR, further comprises pyrosequencing.

Optionally, the at least one primer has a final concentration of about 0.05-0.5 μM, optionally 0.05 μM, optionally 0.5 μM.

Optionally the polymerase chain reaction, or real-time PCR, or quantitative real-time PCR, cycling parameters comprise about 10 minutes incubation at about 95° C., optionally or additionally 50 cycles at about 95° C. for about 10 seconds and about 63° C. for about 30 seconds, optionally or additionally followed by a cooling step at about 40° C. for about 10 seconds.

Optionally, the detecting step (ai) comprises: contacting the sample with a probe capable of hybridizing to at least part of the nucleic acid sequence of the ssrA gene, optionally at least part of the nucleic acid sequence defined by SEQ ID NO. 5, under conditions suitable for hybridisation.

Optionally, the detecting step (ai) comprises: contacting the sample with a probe having a nucleic acid sequence defined by SEQ ID NO. 12 or the reverse complement thereof, under conditions suitable for hybridisation.

Optionally, the at least one probe comprises at least one marker, optionally at least one dye, optionally at least one fluorophore, optionally fluorescein.

Optionally, or additionally, the at least one probe comprises at least one fluorescence quenching dye.

Optionally, the at least one probe has a final concentration of about 0.02-0.8 μM, optionally 0.02 μM, optionally 0.08 μM, optionally 0.2 μM, optionally 0.8 μM.

Optionally, the method is a multiplex method.

Optionally, the method is a multiplex polymerase chain reaction method.

This invention provides a multiplex in vitro nucleic acid amplification method for identifying a serogroup of *Legionella pneumophila* present in a sample, wherein the method comprises detecting the presence or absence of a plurality of nucleic acid molecule targets in the sample in one reaction, wherein at least one of the nucleic acid molecule targets is present in the genome of one or more, but not all, of the serogroups of *Legionella pneumophila.*

Previous methods for the detection of *Legionella pneumophila* have not been capable of specifically identifying *Legionella pneumophila* serogroup 1 in a manner that is practically useful. This means that diagnosis and treatment provision is not tailored to the specific serogroup present unless extensive experimentation is carried out. This requires significant time and effort that is incompatible with rapid and effective diagnosis and treatment. This invention, for the first time, provides a method that is able to identify members of *Legionella pneumophila* serogroup 1 in a rapid and easily-interpretable manner. The inventors have surprisingly found that there is sufficient variation between serogroups yet sufficient conservation between isolates of the same serogroup to specifically identify *Legionella pneumophila* serogroup 1 in a single reaction multiplex nucleic acid amplification assay. By identifying and characterising a series of sequences that are either shared or not shared between the different members of the *Legionella*, the present invention thus allows the use of multiplex nucleic acid amplification methods to specifically detect *Legionella pneumophila* serogroup 1.

The serogroups that make up *Legionella pneumophila* are closely related but differ significantly in their pathology and susceptibility to certain treatments. Therefore, although it is important to be able to distinguish between the different serogroups, it has previously not been possible to do this in any straightforward way that is amenable to use in rapid diagnosis. The different members of *Legionella pneumophila* share a significant proportion of their genetic material. The present invention has successfully identified sufficient differences between the genomes of the members of *Legionella pneumophila* to be able to distinguish between them in multiplex in vitro nucleic acid amplification assays. In contrast to the methods of the prior art, the methods of the present invention allow a single multiplex reaction to be performed that gives clear signals to identify which serogroup is present in the tested sample. It is not necessary to run gels or to undertake complex interpretation of the results.

The present inventors have surprisingly found that it is possible to identify serogroup 1 of *Legionella pneumophila*, despite the high sequence homology that exists between the serogroups of *Legionella pneumophila*. In particular, the present invention provides a multiplex in vitro nucleic acid amplification assay that is capable of identifying serogroups of *Legionella pneumophila*, such as *Legionella pneumophila* serogroup 1 in a single reaction. The inventors have also discovered that the presence of at least one organism selected from the other serogroups in the *Legionella pneumophila* species, including any of serogroups 1-16, can also be identified in the same single reaction. Furthermore, the inventors have devised a method for detecting the presence of other members of the *Legionella* genus, including *Legionella anisa, L. birminghamensis, L. birminghamensis, L. bozemanii, L. bozemanii, L. cincinnatiensis, L. dumoffii, L. dumoffii, L. erythra, L. feeleii*-1, *L. feelii*-2, *L. gormanii, L. gormanii, L. hackeliae*-1, *L. hackeliae*-2, *L. jordanis, L. jordanis, L. lansingensis, L. longbeachae*-1, *L. maceachemii, L. miodadei, L. oakridgensis, L. oakridgensis, L. parisiensis, L. wadworthii, L. cherrii, L. jamestowniensis, L. londoniensis, L. taurinsis, L. moravica, L. adelaidensis, L. donaldsonii, L. gratiana, L. gresilensis, L. fairfieldensis, L. israelensis, L. fallonii, L. brunensis, L. busanensis, L. quinlivanii*, and *L. rubrilicens*.

The present invention contemplates the use of any appropriate method for amplification of target regions. The method of amplification will in general be PCR. Real-time PCR (RT-PCR) is one example of this. In certain embodiments RT-PCR using fluorescent reporter probes is used. The use of the reporter probes significantly increases specificity, and enables quantification even in the presence of non-specific DNA amplification. Fluorescent probes are particularly suited to multiplex assays, as specific probes with different-coloured labels can be used. RT-PCR relies on a DNA-based probe with a fluorescent reporter at one end and a quencher of fluorescence at the opposite end of the probe. The close proximity of the reporter to the quencher prevents detection of its fluorescence; breakdown of the probe by the 5' to 3' exonuclease activity of the DNA polymerase (for example Taq polymerase) breaks the reporter-quencher proximity, and results in emission of fluorescence. An increase in the product targeted by the reporter probe at each PCR cycle therefore causes a proportional increase in fluorescence due to the breakdown of the probe and release of the reporter.

Further, the methods of the invention may therefore be configured to allow quantitation, i.e. the method comprises determining the amount of a member of a group of bacterial organisms in a sample. This may be achieved e.g. by selecting appropriate parameters for amplification (e.g. the number of cycles of amplification).

Other appropriate methods of amplification are referred to below.

Also contemplated for use in the present invention is Nucleic Acid Sequence Based Amplification (NASBA). Nucleic acid sequence-based amplification (NASBA) is an isothermal amplification technique which uses three enzymes (RNase H, AMV reverse transcriptase and T7 RNA polymerase) working in concert at a low isothermal temperature (generally 41° C.). The product of a NASBA reaction is mainly single-stranded RNA, which can be detected by gel electrophoresis, enzyme-linked gel assay (ELGA) or electrochemiluminescent detection (ECL). Alternatively, NASBA products can be detected in real time using molecular beacons included in the reaction. In microbial diagnostics, NASBA has been successfully combined with electrochemiluminescent (ECL), ELISA labelled dendrimer and molecular beacon-based methods to detect and identify viral and bacterial pathogens (Scheler et al., 2009).

Also contemplated for use in the present invention is Rolling Circle Amplification (RCA). RCA describes a process of unidirectional nucleic acid replication that can rapidly synthesize multiple copies of circular molecules of DNA or RNA. RCA is a technology that is adaptable to an on-chip signal amplification format. RCA is well suited to solid phase formats such as microarrays for generating localized signals at specific microarray locations. This distinctive property of RCA should allow many assays to be performed simultaneously (multiplexing) without interference.

Also contemplated for use in the present invention is the Ligase Chain Reaction (LCR). LCR uses two complementary pairs of probes which, when the correct template is available, hybridize next to each other and then are ligated together. These ligated probes plus the original template serve as the template for the next cycle of hybridization and ligation. As subsequent cycles are performed, the amplification proceeds exponentially. A commercially available kit using this technology is the LCx *M. tuberculosis* complex specific kit available from Abbott Diagnostics.

Further isothermal amplification technologies that are contemplated for use with the present invention are provided in and include signal mediated amplification of RNA technology (SMART), strand displacement amplification (SDA), loop mediated isothermal amplification (LAMP), isothermal multiple displacement amplification (IMDA), helicase-dependent amplification (HDA), single primer isothermal amplification (SIPA) and circular helicase dependent amplification (cHDA). As exemplified by SMART, the amplification method used with the invention may comprise signal amplification rather than target amplification.

Also contemplated for use in the present invention is Next Generation Sequencing (NGS). Next generation sequencing is a relatively new field of sequencing which allows for the rapid high throughput process. NGS has the capacity to generate gigabases of nucleotide sequence, depending on the instrument used, in a single run. A recently described assay combines the use of real-time PCR in combination with pyrosequencing which allows for the rapid detection of MTC DNA in addition to sequencing of an 81-bp core region of the rpoB gene associated with rifampin resistance (Halse et al., 2010).

Optionally the sample substantially comprises a water sample.

Optionally the sample substantially comprises an environmental water sample.

Optionally the sample substantially comprises a sample from a water distribution system.

Optionally the sample substantially comprises a sample from a plumbing system.

Optionally the sample substantially comprises a sample from a healthcare facility water system.

Also disclosed is a *Legionella* detection kit comprising at least one primer or probe capable of hybridizing to at least one nucleic acid sequence selected from: at least part of the nucleic acid sequence of the lpg0768 gene or an expression product thereof, at least part of the nucleic acid sequence of the smpB gene or an expression product thereof, at least part of the nucleic acid sequence of the ssrA gene or an expression product thereof; and instructions for use.

Optionally, the kit comprises at least one primer or probe capable of hybridizing to at least one nucleic acid sequence defined by any of SEQ ID NOs 1, 5, 6, and 21-48, or any expression product each thereof; and instructions for use.

Optionally, the kit comprises at least one primer or probe having the nucleic acid sequence defined by any of SEQ ID NOs 2, 3, 4, 7, 8, 9 and 13; and instructions for use.

Also disclosed is a *Legionella* detection assay comprising a solid support and at least one primer or probe capable of hybridizing to at least one nucleic acid sequence selected from: at least part of the nucleic acid sequence of the lpg0768 gene or an expression product thereof, at least part of the nucleic acid sequence of the smpB gene or an expression product thereof, at least part of the nucleic acid sequence of the ssrA gene or an expression product thereof.

Optionally, the assay comprises a solid support and at least one primer or probe capable of hybridizing to at least one nucleic acid sequence defined by any of SEQ ID NOs 1, 5, 6, and 21-48, or any expression product each thereof.

Optionally, the assay comprises a solid support and at least one primer or probe having the nucleic acid sequence defined by any of SEQ ID NOs 2, 3, 4, 7, 8, 9 and 13.

Optionally, the assay is a microarray comprising at least one primer or probe capable of hybridizing to at least one nucleic acid sequence selected from: at least part of the nucleic acid sequence of the lpg0768 gene or an expression product thereof, the at least part of the nucleic acid sequence of the smpB gene or an expression product thereof, the at least part of the nucleic acid sequence of the ssrA gene or an expression product thereof.

Optionally, the microarray comprises at least one primer or probe capable of hybridizing to at least one nucleic acid sequence defined by any of SEQ ID NOs 1, 5, 6, and 21-48, or any expression product each thereof.

Optionally, the microarray discloses at least one primer or probe having the nucleic acid sequence defined by any of SEQ ID NOs 2, 3, 4, 7, 8, 9 and 13.

Also disclosed is a method for detecting Legionnaires' disease comprising a method according to the invention, wherein the presence of at least part of the nucleic acid sequence of the lpg0768 gene or expression product thereof indicates the presence of Legionnaires' disease.

Optionally, the method for detecting Legionnaires' disease comprises the steps of:

(a) detecting the presence, absence, or quantity of at least part of the nucleic acid sequence of the lpg0768 gene or an expression product thereof; and
(b) correlating the presence, absence, or quantity of the at least part of the nucleic acid sequence of the lpg0768 gene or expression product thereof, to the presence, absence, or quantity of Legionnaires' disease.

Optionally, the method is an in vitro method.

Optionally, any probe used in the method for detecting Legionnaires' disease may further comprise at least one dye, optionally at least one fluorophore, optionally hexachlorofluorescein, optionally rhodamine, optionally fluorescein.

Optionally or additionally, the probe may further comprise at least one fluorescence quenching dye.

The term "expression product" refers to any molecule that may be obtained from a nucleic acid sequence by transcription, translation, post-translational modification, or reverse transcription; including but not limited to RNA, amino acid polypeptide, protein, and complementary DNA.

The term "sg1" is synonymous with the term "serogroup 1".

The term "terminal quencher" refers to a fluorescence quenching dye, which can be located at or adjacent at least one end, optionally located at or adjacent at least one terminal end, of a probe; for example, located at or adjacent at least the 3' end of an oligonucleotide probe.

The term "internal quencher" refers to a fluorescence quenching dye, which can be located between the ends, optionally located between the terminal ends of a probe; for example, located between the 3' and 5' ends of an oligonucleotide probe.

BRIEF DESCRIPTION OF THE DRAWINGS

Embodiments of the invention will now be described with reference to the accompanying drawings in which:

FIG. 1(*b*) illustrates quantitative real-time PCR amplification curves, showing exclusivity testing of the *L. pneumophila* serogroup 1 assay targeting a region of the lpg0768 gene. No cross reactions were observed with strains closely related to *L. pneumophila* serogroup 1;

FIG. 2(*b*) illustrates quantitative real-time PCR amplification curves, showing exclusivity testing of the *L. pneumophila* species assay targeting a region of the smpB gene. No cross reactions were observed with non-*Legionella pneumophila* species and strains tested for.

FIG. 3(*b*) illustrates quantitative real-time PCR amplification curves, showing the specificity of the *L. pneumophila* serogroup 1 assay targeting a region of the lpg0768 gene for detection of *L. pneumophila* serogroup 1 isolates;

FIG. 3(*c*) illustrates quantitative real-time PCR amplification curves, showing the specificity of the *L. pneumophila* species assay targeting a region of the smpB gene for detection of all *L. pneumophila* strains and non-detection of other *Legionella* species; and FIG. 3(*d*) illustrates quantitative real-time PCR amplification curves, showing detection of the Internal Amplification Control (IAC) assay in each sample tested for.

FIG. 4(D) illustrates quantitative real-time PCR amplification curves, showing detection of the Internal Amplification Control (IAC) assay in each sample tested for.

EXAMPLES

Figure 1A:
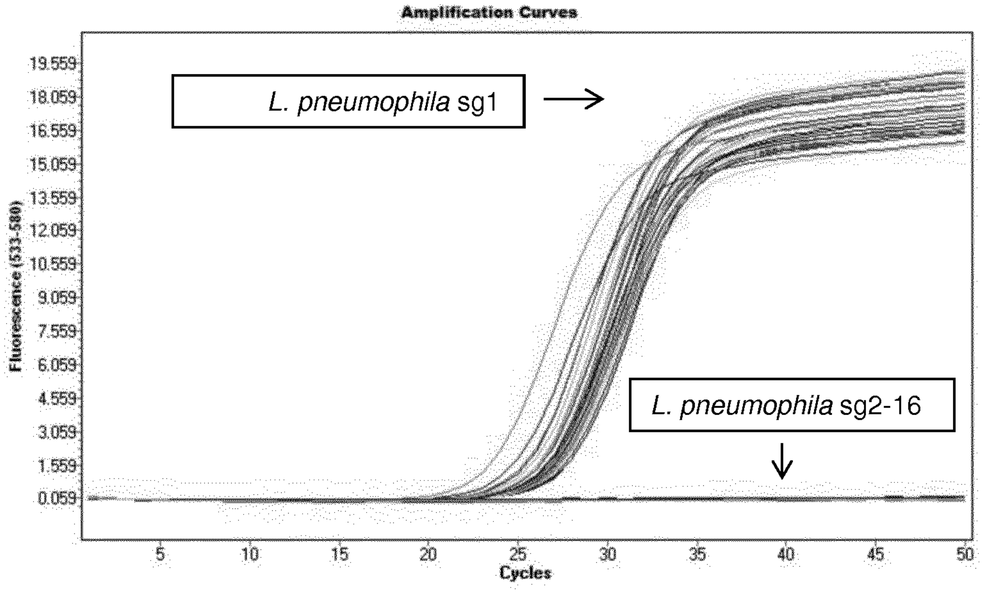
FIG. 1(*a*) illustrates quantitative real-time PCR amplification curves, showing inclusivity testing of the *L. pneumophila* serogroup 1 assay targeting a region of the lpg0768 gene for detection of *L. pneumophila* serogroup 1 strains.

Embodiments of the present invention will now be described with reference to the following non-limiting examples:

Example 1

Real-Time PCR Assay for the Detection of *Legionella pneumophila* Serogroup 1

In Silico Target Identification

Publicly available whole genome sequence information was retrieved from the National Center for Biotechnology Information website (www.ncbi.nlm.nih.gov/) for *Legionella pneumophila* serogroup 1 and *Legionella pneumophila* serogroup 6 and serogroup 12. Regions potentially unique to *L. pneumophila* serogroup 1 were identified using WEBACT (www.webact.org/). This resulted in a number of regions of difference in *L. pneumophila* serogroup 1. Each identified putative target nucleotide sequence was BLAST analysed (blast.ncbi.nlm.nih.gov/Blast.cgi) to determine if they were present in all *L. pneumophila* serogroup 1 and absent in all other *L. pneumophila* serogroups or closely related *Legionella* species. One region was present in all *L. pneumophila* serogroup 1 analysed with very low or no sequence similarity to other *L. pneumophila* serogroups or closely related *Legionella* species. This region was the lpg0768 gene (SEQ ID NOs 1 and 21-48) which codes for spore coat polysaccharide biosynthesis protein E, NeuB. Closely related nucleotide sequences were aligned using ClustalW (www.ebi.ac.uk/Tools/msa/clustalw2/).

In this example, the following exemplary real-time PCR assay primers and probe for the lpg0768 gene (SEQ ID NOs 1 and 21-48) were used: spore coat polysaccharide biosynthesis protein E forward primer (SEQ ID NO. 2), spore coat polysaccharide biosynthesis protein E reverse primer (SEQ ID NO. 3), spore coat polysaccharide biosynthesis protein E probe (SEQ ID NO. 4). The spore coat probe (SEQ ID NO. 4) comprised at least one marker, optionally at least one dye, optionally at least one fluorophore, optionally hexachlorofluorescein (5' HEX, Integrated DNA Technologies). Optionally, the spore coat polysaccharide biosynthesis protein E probe (SEQ ID NO. 4) comprises at least one fluorescence quenching dye, optionally an internal quencher, such as ZEN™ quencher, Integrated DNA Technologies; and/or a terminal quencher, such as 3' Iowa Black® FQ, Integrated DNA Technologies; or Black Hole Quencher 1®, LGC Biosearch.

Bacterial Strains, Culture Media, and Growth Conditions

A panel of 26 *Legionella pneumophila* strains and 41 other *Legionella* species were used in this study (Table 1(a) and 1(b)). These species and strains were purchased from the German Collection of Microorganisms and Cell Cultures (Deutsche Sammlung von Mikroorganismen und Zellkulturen GmbH, DSMZ. Braunschweig, Germany), the National Collection of Type Cultures (NCTC, Public Health England, Salisbury, United Kingdom), American Type Culture Collection (ATCC, provided by LGC standards, Middlesex United Kingdom). All *Legionella* species and strains were cultured on buffered charcoal yeast extract (BCYE) media at 37° C. 18-24 hours or until sufficient growth was observed.

TABLE 1(a)

Inclusivity panel

| Strain | Culture collection number |
|---|---|
| *Legionella pneumophila* subsp. *pneumophila*-1 | DSM 7513 |
| *Legionella pneumophila* subsp. *pneumophila*-1 | NCTC 11191 |
| *Legionella pneumophila* subsp. *pneumophila*-1 | NCTC 11231 |
| *Legionella pneumophila* subsp. *pneumophila*-1 | NCTC 11286 |
| *Legionella pneumophila* subsp. *pneumophila*-1 | NCTC 11378 |
| *Legionella pneumophila* subsp. *pneumophila*-1 | NCTC 11404 |
| *Legionella pneumophila* subsp. *pneumophila*-1 | DSM 25019 |
| *Legionella pneumophila* subsp. *pneumophila*-1 | DSM 25021 |
| *Legionella pneumophila* subsp. *pneumophila*-1 | DSM 25199 |
| *Legionella pneumophila* subsp. *pneumophila*-1 | DSM 25200 |
| *Legionella pneumophila* subsp. *pneumophila*-1 | DSM 25213 |
| *Legionella pneumophila* subsp. *pneumophila*-1 | DSM 37564 |

TABLE 1(b)

Exclusivity panel

| Species | Culture collection number |
|---|---|
| *Legionella pneumophila* subsp. *fraseri*-4 | DSM 7514 |
| *Legionella pneumophila* subsp. *pasculei*-5 | DSM 7515 |
| *Legionella pneumophila* subsp. *pneumophila*-1 | NCTC 11231 |
| *Legionella pneumophila* subsp. *pneumophila*-3 | NCTC 11232 |
| *Legionella pneumophila* subsp. *pneumophila*-6 | NCTC 11287 |
| *Legionella pneumophila* subsp. *pneumophila*-5 | NCTC 11417 |
| *Legionella pneumophila* subsp. *pneumophila*-7 | NCTC 11984 |
| *Legionella pneumophila* subsp. *pneumophila*-8 | NCTC 11985 |
| *Legionella pneumophila* subsp. *pneumophila*-9 | NCTC 11986 |
| *Legionella pneumophila* subsp. *pneumophila*-10 | NCTC 12000 |
| *Legionella pneumophila* subsp. *pneumophila*-14 | NCTC 12174 |
| *Legionella pneumophila* subsp. *pneumophila*-11 | NCTC 12179 |
| *Legionella pneumophila* subsp. *pneumophila*-12 | NCTC 12180 |
| *Legionella pneumophila* subsp. *pneumophila*-13 | NCTC 12181 |
| *Legionella anisa* | DSM 17627 |
| *Legionella birminghamensis* | DSM 19232 |
| *Legionella. birminghamensis* | ATCC 700709 |
| *Legionella bozemanii* | NCTC 11975 |
| *Legionella bozemanii* | DSM 16523 |
| *Legionella cincinnatiensis* | DSM 19233 |
| *Legionella dumoffii* | DSM 17625 |
| *Legionella dumoffii* | ATCC 33343 |
| *Legionella erythra* | DSM 17644 |
| *Legionella feeleii*-1 | DSM 17645 |

TABLE 1(b)-continued

| Exclusivity panel | |
|---|---|
| Species | Culture collection number |
| *Legionella feelii*-2 | NCTC 11978 |
| *Legionella gormanii* | DSM 16641 |
| *Legionella gormanii* | ATCC 43769 |
| *Legionella hackeliae*-1 | DSM 19214 |
| *Legionella hackeliae*-2 | NCTC 11980 |
| *Legionella jordanis* | DSM 19212 |
| *Legionella jordanis* | ATCC 700762 |
| *Legionella lansingensis* | DSM 19556 |
| *Legionella longbeachae*-1 | DSM 10572 |
| *Legionella maceachemii* | DSM 16642 |
| *Legionella miodadei* | NCTC 11403 |
| *Legionella oakridgensis* | NCTC 11531 |
| *Legionella oakridgensis* | ATCC 700515 |
| *Legionella parisiensis* | DSM 19216 |
| *Legionella wadworthii* | NCTC 11532 |
| *Legionella cherrii* | DSM 19213 |
| *Legionella jamestowniensis* | DSM 19215 |
| *Legionella londoniensis* | DSM 21234 |
| *Legionella taurinsis* | CCUG 44901 |
| *Legionella moravica* | DSM 19234 |
| *Legionella adelaidensis* | DSM 19888 |
| *Legionella donaldsonii* | ATCC BAA-693 |
| *Legionella gratiana* | DSM 21233 |
| *Legionella gresilensis* | DSM 21218 |
| *Legionella fairfieldensis* | NCTC 12488 |
| *Legionella israelensis* | DSM 19235 |
| *Legionella fallonii* | CCUG 43887 |
| *Legionella brunensis* | DSM 19236 |
| *Legionella busanensis* | ATCC BAA-518 |
| *Legionella quinlivanii* | NCTC 12434 |
| *Legionella rubrilicens* | DSM 11884 |

DNA Isolation and Quantification

Genomic DNA from *Legionella* cultures were isolated using a modified procedure combining mechanical lysis (IDI lysis kit; Becton Dickenson, Canada) and purification using a DNA purification kit (quick gDNA kit; Zymo Research, Irvine, CA, USA). Briefly, a loop of culture was resuspended in 250 ul lysis buffer (IDI lysis buffer). The suspension was transferred to a cell lysis tube (GeneOhm) and bead beaten (Mini-Bead-Beater-16; Stratech, United Kingdom) for 3 minutes. After bead beating, 200 µl was transferred to a nucleic acid purification spin column (Zymo-Spin™ Column) in a collection tube and steps 2 to 5 of the procedure for purification of total DNA from cell suspensions were followed, according to the manufacturers instructions.

Assay Design

All oligonucleotide primers and probes used in this study were designed in accordance with published guidelines.

Real-Time PCR

This *Legionella pneumophila* serogroup 1 specific assay was then tested in a real-time PCR format against a panel of well characterised *Legionella* species to determine assay specificity (Inclusivity and Exclusivity testing) and suitability of the target nucleotide sequence as a diagnostics marker.

Real-time PCR was performed on a real-time PCR amplification device (LightCycler® 480 Instrument, Roche Diagnostics) using a real-time PCR probes kit (LightCycler® 480 Probes Master kit, Roche Diagnostics). The reaction mixture comprised: master mix (LightCycler® 480 Probes Master; 6.4 mM $MgCl_2$) forward and reverse primer (0.5 µM final conc.), carboxyfluorescein (FAM) labelled probe (0.2 µM final conc.), template DNA (5 µl) and nuclease free $dH_2O$ to a final volume of 20 µl. The cycling parameters consisted of 10 minutes incubation at 95° C. to activate the polymerase (Taq), 50 cycles of 95° C. for 10 seconds and 60° C. for 30 s, followed by a cooling step at 40° C. for 10 s. The temperature transition rate (ramp rate on the LightCycler® 480 Instrument) was 4.4° C./s while heating and 2.2° C./s while cooling.

Figure 1B:
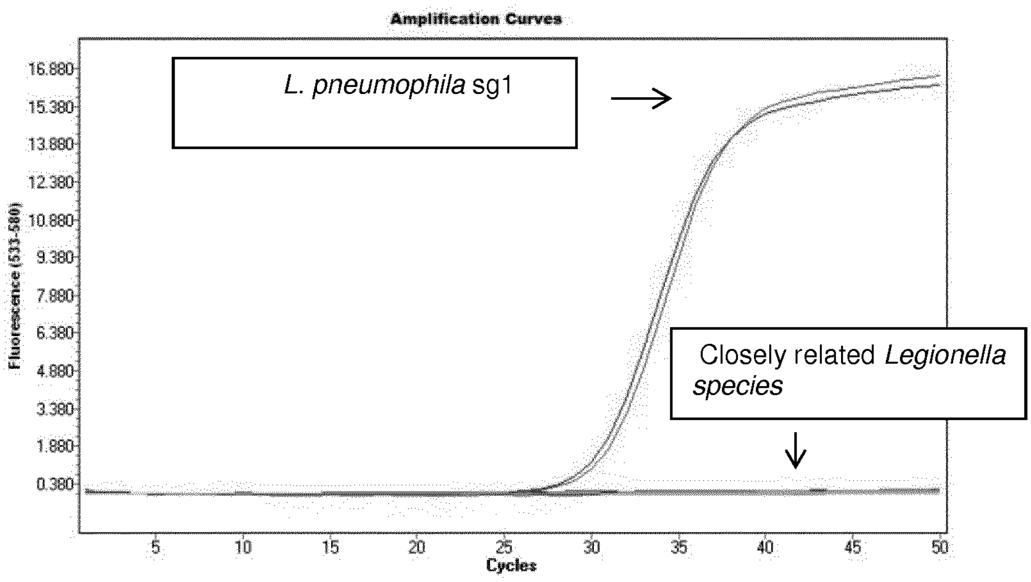

As demonstrated (FIG. 1(*a*)), the assay targeting a region of the lpg0768 gene detected all 12 *Legionella pneumophila* serogroup 1 strains tested for (Table 1(a)); but the assay did not detect *Legionella pneumophila* serogroup 2-16 strains, or the no template control. The remaining *Legionella* species tested for (Table 1(b)) were not detected by the assay targeting a region of the lpg0768 gene (FIG. 1(*b*)).

Example 2

Assay for the Detection of *Legionella pneumophila*

In Silico Analysis

Publicly available smpB gene nucleotide sequence information was retrieved from the National Center for Biotechnology Information website (www.ncbi.nlm.nih.gov/) for *Legionella pneumophila* and aligned using ClustalW (www.ebi.ac.uk/Tools/msa/clustalw2/). Partial gene sequence was also generated for a number of culture collection strains using sequencing primers and then aligned. All publicly available and generated nucleotide sequences for *Legionella pneumophila* sequences were subsequently aligned which demonstrated sufficient nucleotide similarity to design oligonucleotide primers and probes.

In this example, the following exemplary real-time PCR assay primers and probe for the smpB gene nucleotide sequence (SEQ ID NO. 6) were used: smpB forward primer (SEQ ID NO. 7), smpB reverse primer (SEQ ID NO. 8), smpB probe (SEQ ID NO. 9). Optionally an alternative smpB reverse primer (SEQ ID No. 13) could be used. The smpB probe (SEQ ID NO. 9) comprised at least one marker, optionally at least one dye, optionally at least one fluorophore, optionally rhodamine (5' ROX, Integrated DNA Technologies). Optionally, the smpB probe (SEQ ID NO. 9) comprised at least one fluorescence quenching dye, optionally a terminal quencher (3' Iowa Black® RQ, Integrated DNA Technologies; or Black Hole Quencher 2®, LGC Biosearch).

Nucleotide Sequencing

To generate a partial smpB gene nucleotide sequence for *L. pneumophila*, conventional PCR was performed using sequencing primers on a thermal cycler (iCycler iQ thermal cycler; Bio-Rad Laboratories Inc., California, USA). All reactions were carried out in a final volume of 50 µl, containing 5 µl 10× buffer (15 mM $MgCl_2$), 1 µl forward and reverse primers (0.2 µM final conc.), 2 µl DNA polymerase (Taq; 1 U/µl, Roche Diagnostics, Basel, Switzerland), 1 µl dNTP mix (10 mM deoxynucleoside triphosphate set; Roche Diagnostics), 5 µl of template DNA and 35 µl nuclease free water (Applied Biosystems/Ambion, Texas, USA). The cycling parameters consisted of initial denaturation at 95° C. for 5 minutes, followed by 35 cycles of denaturation at 95° C. (1 minutes), annealing at 50° C. (1 minutes), and extension at 72° C. (1 minutes), with a final elongation step at 72° C. for 10 minutes.

PCR products were visualised on a 1.5% agarose gel and subsequently purified using a PCR product purification kit (High Pure PCR Product Purification Kit, Roche Diagnostics). Purified PCR products were sent for sequencing externally (Sequiserve, Vaterstetten, Germany).

DNA Isolation and Quantification

Genomic DNA from *Legionella* cultures were isolated using a modified procedure combining mechanical lysis (IDI lysis kit; Becton Dickenson, Canada) and purification using a DNA purification kit (quick gDNA kit, Zymo Research, Irvine, CA, USA). Briefly, a loop of culture was resuspended in 250 ul lysis buffer (IDI lysis buffer). The suspension was transferred to a cell lysis tube (GeneOhm) and bead beaten (Mini-Bead-Beater-16; Stratech, United Kingdom) for 3 minutes. After bead beating, 200 μl was transferred to a nucleic acid purification spin column (Zymo-Spin™ Column) in a collection tube and steps 2 to 5 of the procedure for purification of total DNA from cell suspensions were followed, according to the manufacturers instructions.

Bacterial Strains, Culture Media, and Growth Conditions

A panel of 26 *Legionella pneumophila* strains and 41 other *Legionella* species and 14 other bacteria were used in this study (Table 2(a) and Table 2(b)). These species and strains were purchased from the German Collection of Microorganisms and Cell Cultures (Deutsche Sammlung von Mikroorganismen und Zellkulturen GmbH, DSMZ. Braunschweig, Germany), the National Collection of Type Cultures (NCTC, Public Health England, Salisbury, United Kingdom), American Type Culture Collection (ATCC, provided by LGC standards, Middlesex United Kingdom) and Culture Collection, University of Göteborg, (CCUG, Sweden). All *Legionella* species and strains were cultured on BCYE media at 37° C. 18-24 hours or until sufficient growth was observed.

TABLE 2(a)

*Legionella pneumophila* strains used in this study

| Strain | Culture collection |
|---|---|
| *Legionella pneumophila* subsp. *pneumophila*-1 | DSM 7513 |
| *Legionella pneumophila* subsp. *fraseri*-4 | DSM 7514 |
| *Legionella pneumophila* subsp. *pasculei*-5 | DSM 7515 |
| *Legionella pneumophila* subsp. *pneumophila*-1 | NCTC 11191 |
| *Legionella pneumophila* subsp. *pneumophila*-2 | NCTC 11230 |
| *Legionella pneumophila* subsp. *pneumophila*-1 | NCTC 11231 |
| Legionella pneumophila subsp. *pneumophila*-3 | NCTC 11232 |
| *Legionella pneumophila* subsp. *pneumophila*-1 | NCTC 11286 |
| *Legionella pneumophila* subsp. *pneumophila*-6 | NCTC 11287 |
| *Legionella pneumophila* subsp. *pneumophila*-1 | NCTC 11378 |
| *Legionella pneumophila* subsp. *pneumophila*-1 | NCTC 11404 |
| *Legionella pneumophila* subsp. *pneumophila*-5 | NCTC 11417 |
| *Legionella pneumophila* subsp. *pneumophila*-7 | NCTC 11984 |
| *Legionella pneumophila* subsp. *pneumophila*-8 | NCTC 11985 |
| *Legionella pneumophila* subsp. *pneumophila*-9 | NCTC 11986 |
| *Legionella pneumophila* subsp. *pneumophila*-10 | NCTC 12000 |
| *Legionella pneumophila* subsp. *pneumophila*-14 | NCTC 12174 |
| *Legionella pneumophila* subsp. *pneumophila*-11 | NCTC 12179 |
| *Legionella pneumophila* subsp. *pneumophila*-12 | NCTC 12180 |
| *Legionella pneumophila* subsp. *pneumophila*-13 | NCTC 12181 |
| *Legionella pneumophila* subsp. *pneumophila*-1 | DSM 25019 |
| *Legionella pneumophila* subsp. *pneumophila*-1 | DSM 25071 |
| *Legionella pneumophila* subsp. *pneumophila*-1 | DSM 25199 |
| *Legionella pneumophila* subsp. *pneumophila*-1 | DSM 25200 |
| *Legionella pneumophila* subsp. *pneumophila*-1 | DSM 25213 |
| *Legionella pneumophila* subsp. *pneumophila*-1 | DSM 27564 |

DSM = The German Collection of Microorganisms;
NCTC = National Collection of Type Cultures TABLE 2(b)

Other *Legionella* species tested in this study

| Species | culture collection number |
|---|---|
| *Legionella anisa* | DSM 17627 |
| *Legionella birminghamensis* | DSM 19232 |
| *Legionella. birminghamensis* | ATCC 700709 |
| *Legionella bozemanii* | NCTC 11975 |
| *Legionella bozemanii* | DSM 16523 |
| *Legionella cincinnatiensis* | DSM 19233 |
| *Legionella dumoffii* | DSM 17625 |
| *Legionella dumoffii* | ATCC 33343 |
| *Legionella erythra* | DSM 17644 |
| *Legionella feeleii*-1 | DSM 17645 |
| *Legionella feelii*-2 | NCTC 11978 |
| *Legionella gormanii* | DSM 16641 |
| *Legionella gormanii* | ATCC 43769 |
| *Legionella hackeliae*-1 | DSM 19214 |
| *Legionella hackeliae*-2 | NCTC 11980 |
| *Legionella jordanis* | DSM 19212 |
| *Legionella jordanis* | ATCC 700762 |
| *Legionella lansingensis* | DSM 19556 |
| *Legionella longbeachae*-1 | DSM 10572 |
| *Legionella maceachemii* | DSM 16642 |
| *Legionella miodadei* | NCTC 11403 |
| *Legionella oakridgensis* | NCTC 11531 |
| *Legionella oakridgensis* | ATCC 700515 |
| *Legionella parisiensis* | DSM 19216 |
| *Legionella wadworthii* | NCTC 11532 |
| *Legionella cherrii* | DSM 19213 |
| *Legionella jamestowniensis* | DSM 19215 |
| *Legionella londoniensis* | DSM 21234 |
| *Legionella taurinsis* | CCUG 44901 |
| *Legionella moravica* | DSM 19234 |
| *Legionella adelaidensis* | DSM 19888 |
| *Legionella donaldsonii* | ATCC BAA-693 |
| *Legionella gratiana* | DSM 21233 |
| *Legionella gresilensis* | DSM 21218 |
| *Legionella fairfieldensis* | NCTC 12488 |
| *Legionella israelensis* | DSM 19235 |
| *Legionella fallonii* | CCUG 43887 |
| *Legionella brunensis* | DSM 19236 |
| *Legionella busanensis* | ATCC BAA-518 |
| *Legionella quinlivanii* | NCTC 12434 |
| *Legionella rubrilicens* | DSM 11884 |
| *Burkholderia cepacia* | DSM 7522 |
| *Ralstonia pickettii* | DSM 6297 |
| *Serratia marcescens* | DSM 30121 |
| *Cupriavidus pauculus* | DSM 17313 |
| *Stenotrophomonas maltophilia* | DSM 21874 |
| *Pseudomonas maltophila* | DSM 50071 |
| *Klebsiella pneumoniae* | DSM 12059 |
| *Proteus mirabilis* | DSM 4479 |
| *Enterobacter aerogenes* | DSM 2969 |
| *Acinetobacter baumannii* | LMG 984 |
| *Staphylococcus aureus* | DSM 11822 |
| *Bacillus cereus* | DSM 30584 |
| *Clostridium difficile* | DSM 1296 |
| *Sphingomonas paucimobilis* | DSM 1098 |

DSM = The German Collection of Microorganisms;
ATCC = American Type Culture Collection;
NCTC = National Collection of Type Cultures;
CCUG = Culture Collection, University of Göteborg Real-Time PCR The *Legionella pneumophila* specific assay was then tested in a real-time PCR format against a panel of well characterised *Legionella* species to determine assay specificity (Inclusivity and Exclusivity testing) and suitability of the smpB gene nucleotide sequence as a diagnostics marker.

Real-time PCR was performed on a real-time PCR amplification device (LightCycler® 480 Instrument, Roche Diagnostics) using a real-time PCR probes kit (LightCycler® 480 Probes Master kit, Roche Diagnostics). The reaction mixture comprised: master mixture (LightCycler® 480 Probes Master) in 6.4 mM $MgCl_2$, forward and reverse primer (0.5 μM final conc.), carboxyfluorescein (FAM) labelled probe (0.2 μM final conc.), template DNA (5 μl) and nuclease free $dH_2O$ to a final volume of 20 μl. The cycling parameters consisted of 10 minutes incubation at 95° C. to activate the polymerase (Taq), 50 cycles of 95° C. for 10 seconds and 60° C. for 30 s, followed by a cooling step at 40° C. for 10 s. The temperature transition rate, (ramp rate on the LightCycler® 480 Instrument) was 4.4° C./s while heating and 2.2° C./s while cooling.

Figure 2A:
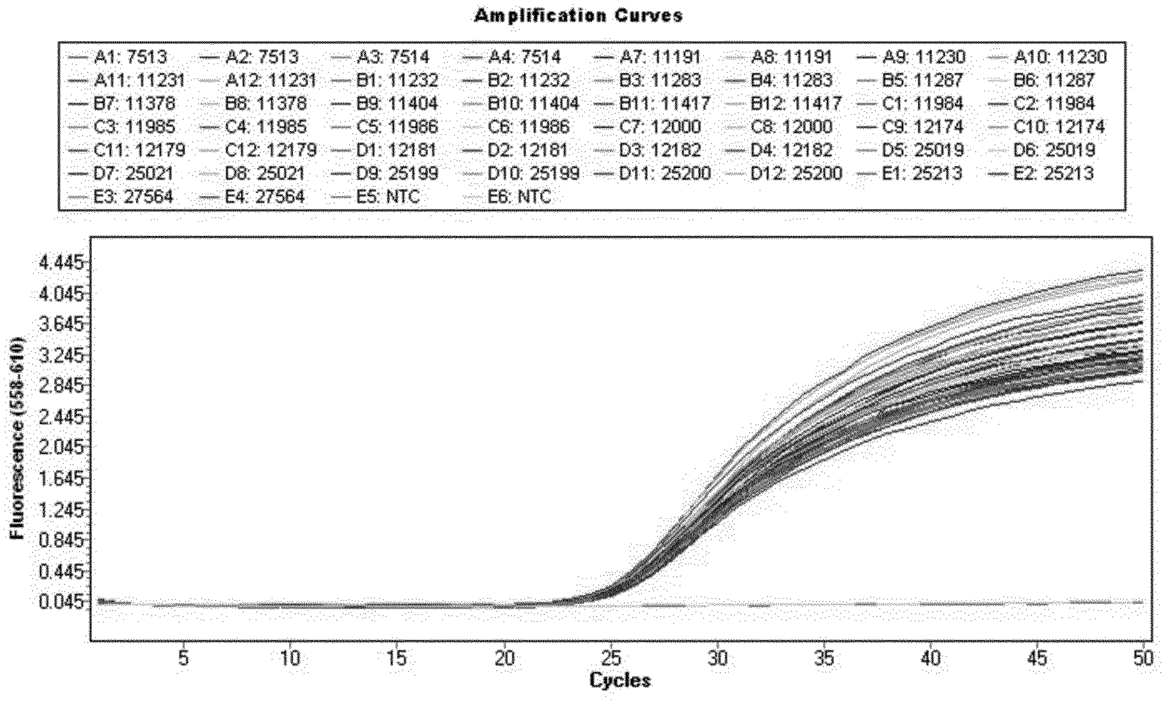
FIG. 2(*a*) illustrates quantitative real-time PCR amplification curves, showing inclusivity testing of the *L. pneumophila* species assay targeting a region of the smpB gene for detection of *L. pneumophila* strains.
Figure 2B:
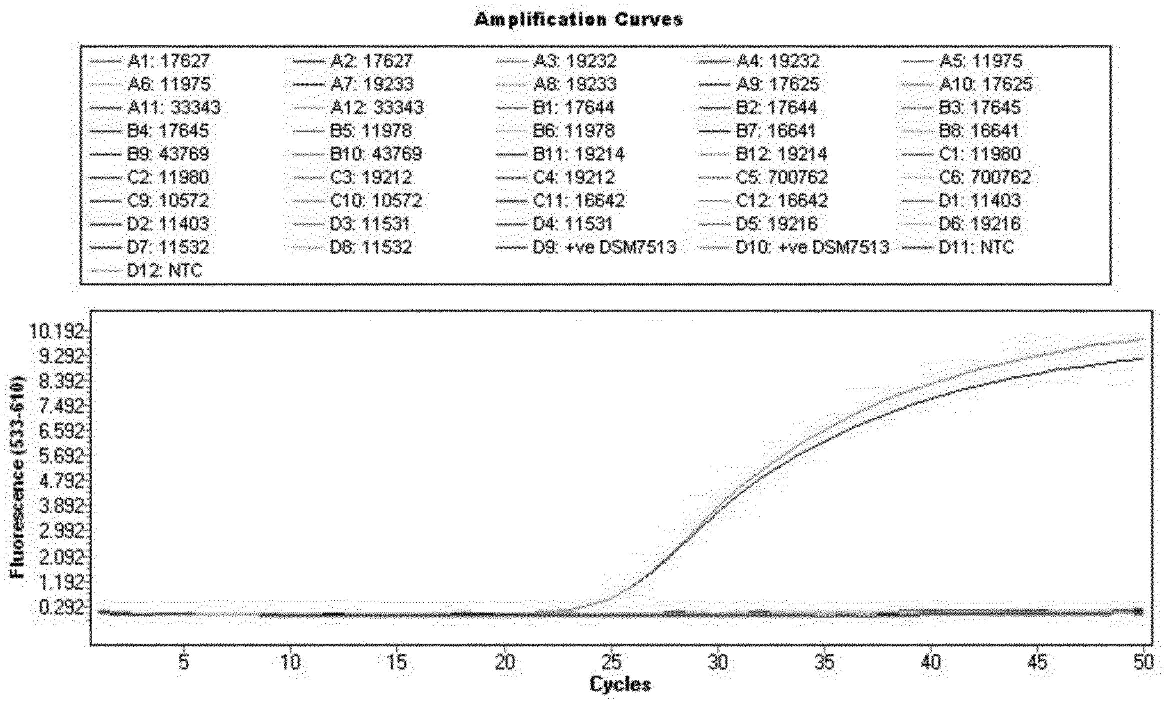
Figure 3A:
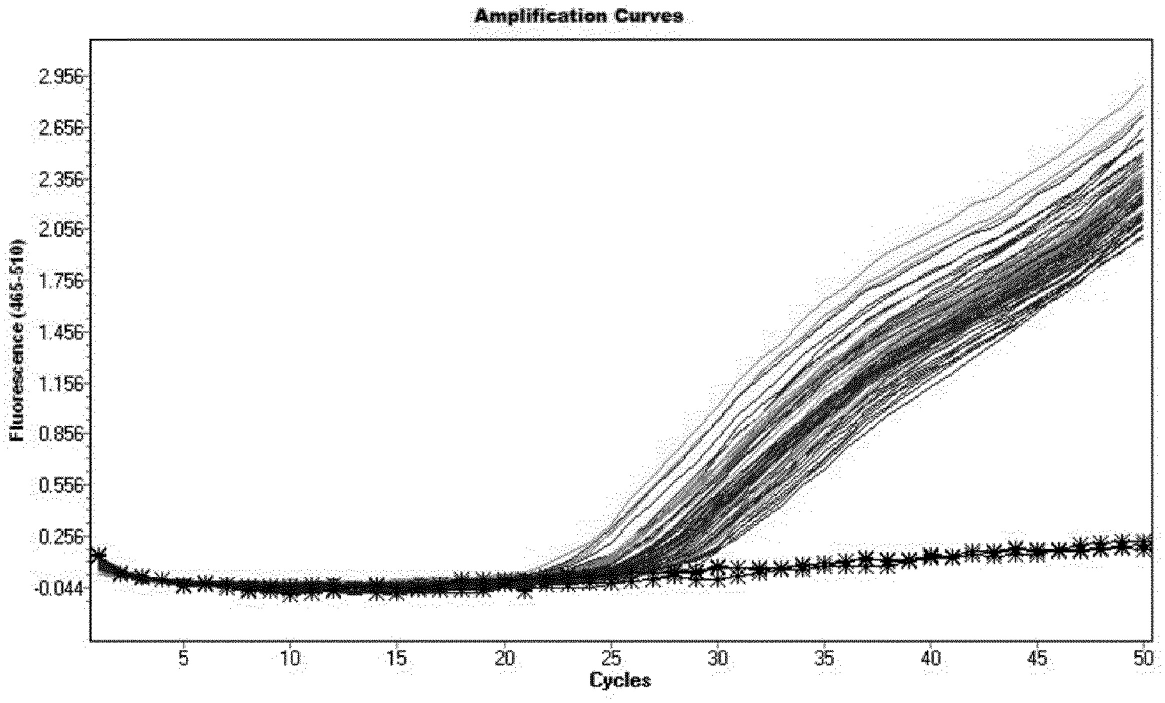
FIG. 3(*a*) illustrates quantitative real-time PCR amplification curves, showing inclusivity testing of species of the *Legionella* genus assay targeting a region of the ssrA gene for detection of *Legionella* strains, using the multiplex assay.
Figure 3B:
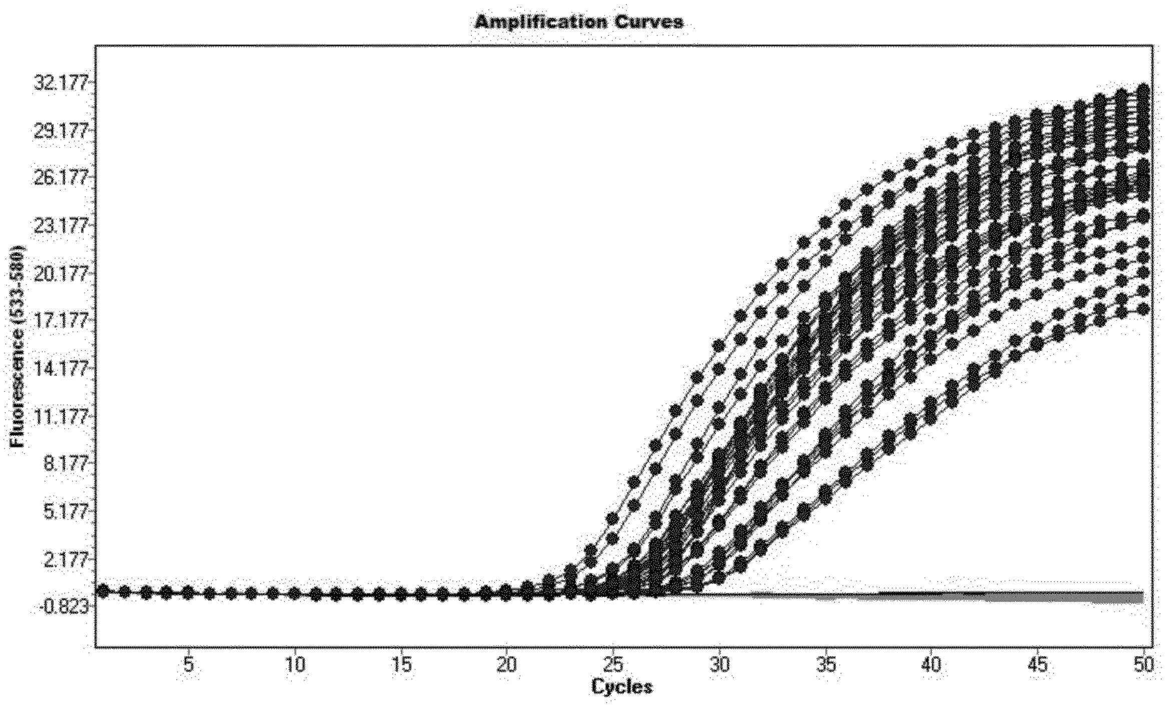
Figure 3C:
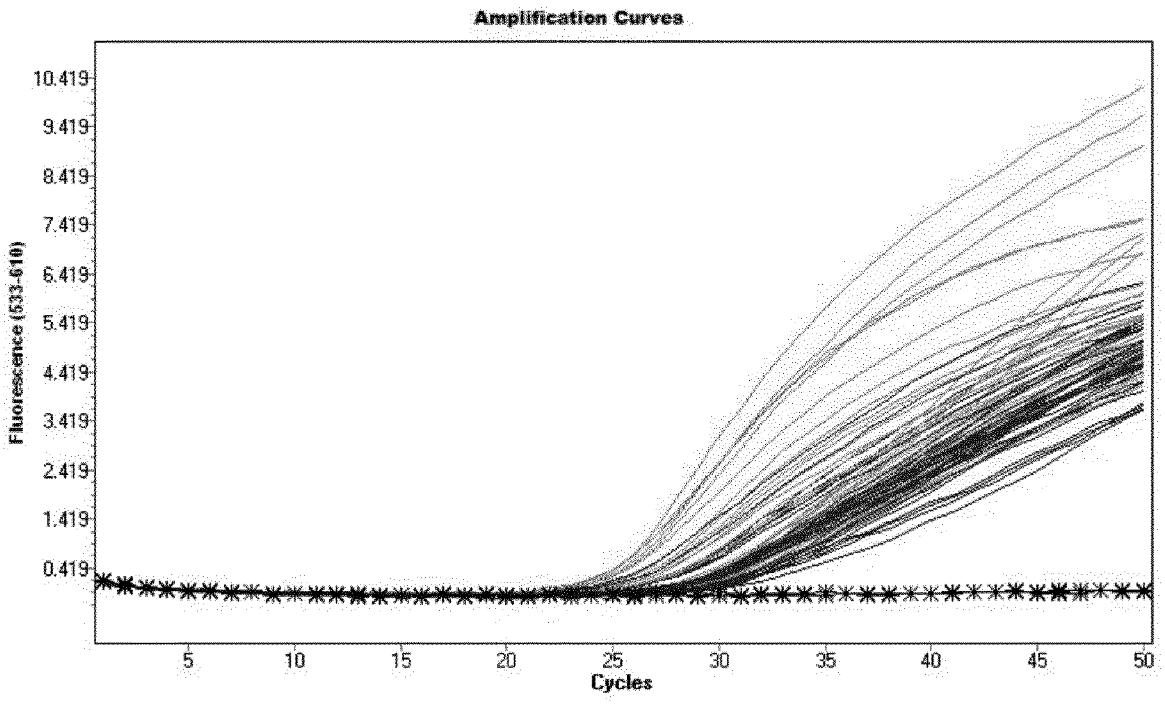
Figure 3D:
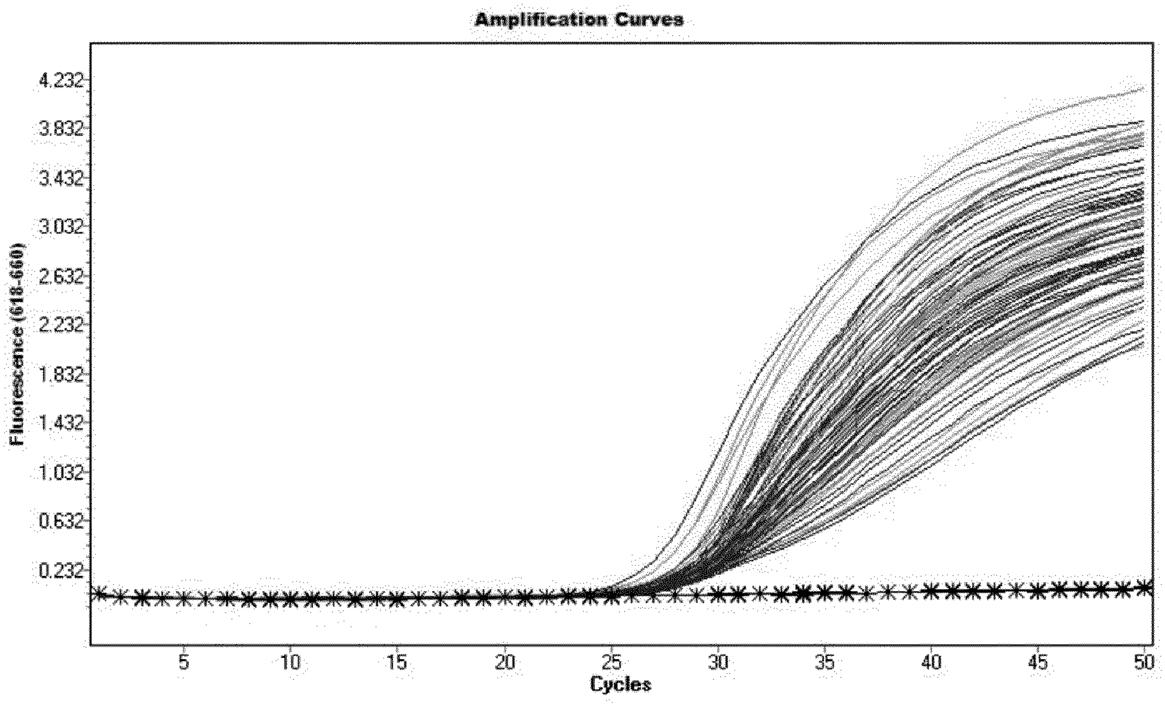
Figure 4A:
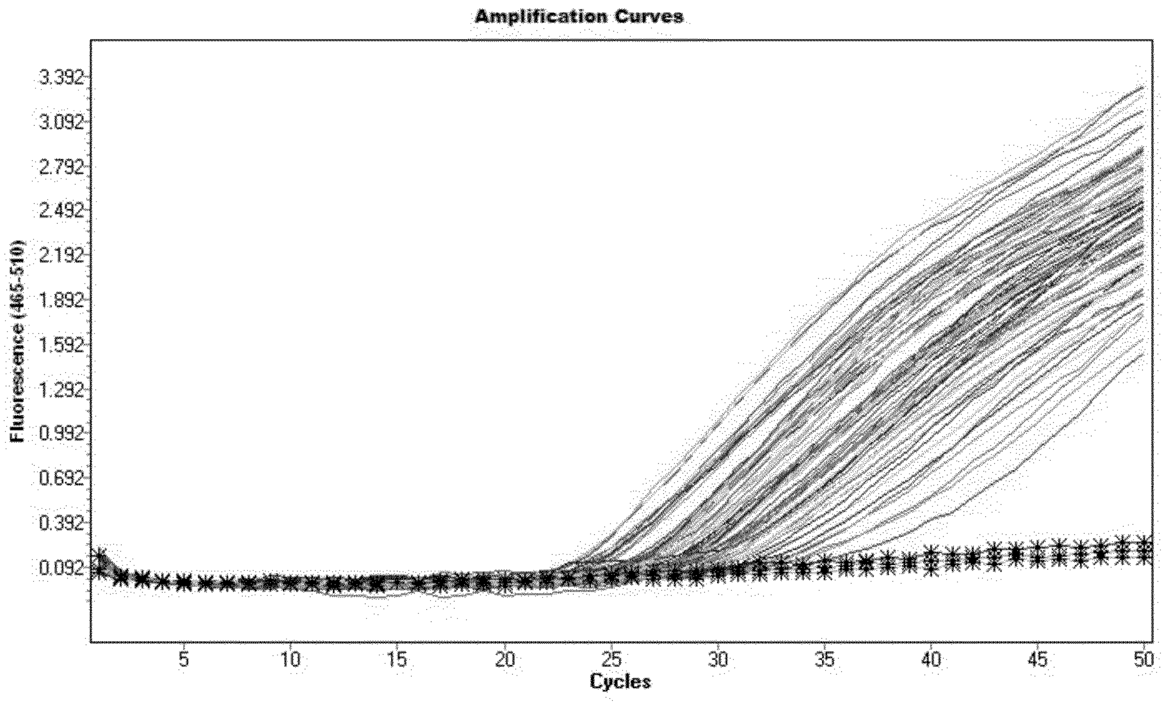
FIG. 4(A) illustrates quantitative real-time PCR amplification curves, showing inclusivity testing of species of the *Legionella* genus assay targeting a region of the ssrA gene for detection of *Legionella* strains, using the multiplex assay.
Figure 4B:
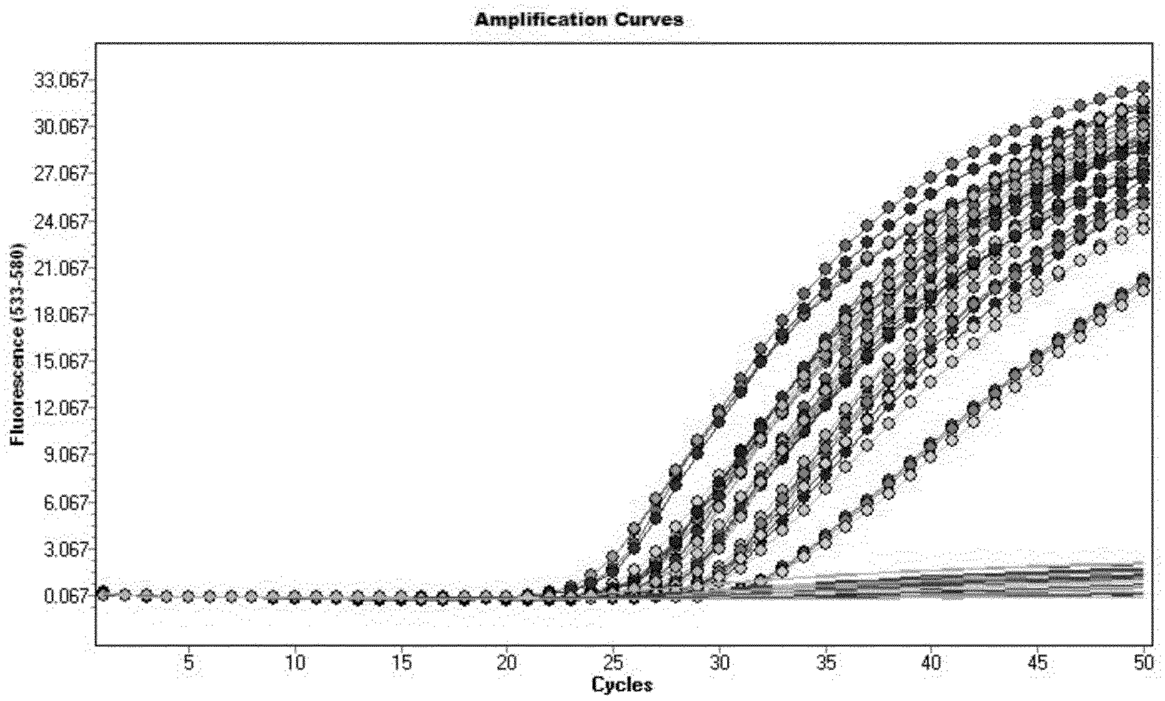
FIG. 4(B) illustrates quantitative real-time PCR amplification curves, showing the specificity of the *L. pneumophila* serogroup 1 assay targeting a region of the lpg0768 gene for detection of *L. pneumophila* serogroup 1 isolates.
Figure 4C:
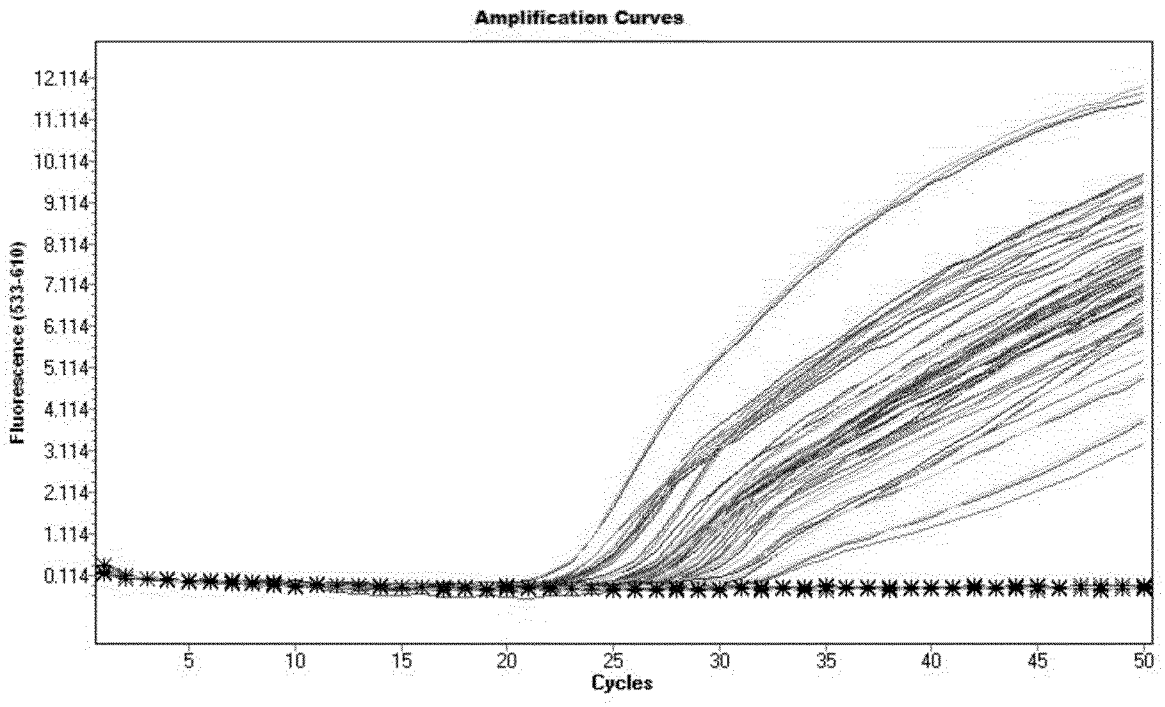
FIG. 4(C) illustrates quantitative real-time PCR amplification curves, showing the specificity of the *L. pneumophila* species assay targeting a region of the smpB gene for detection of all *L. pneumophila* strains and non-detection of other *Legionella* species.
Figure 4D:
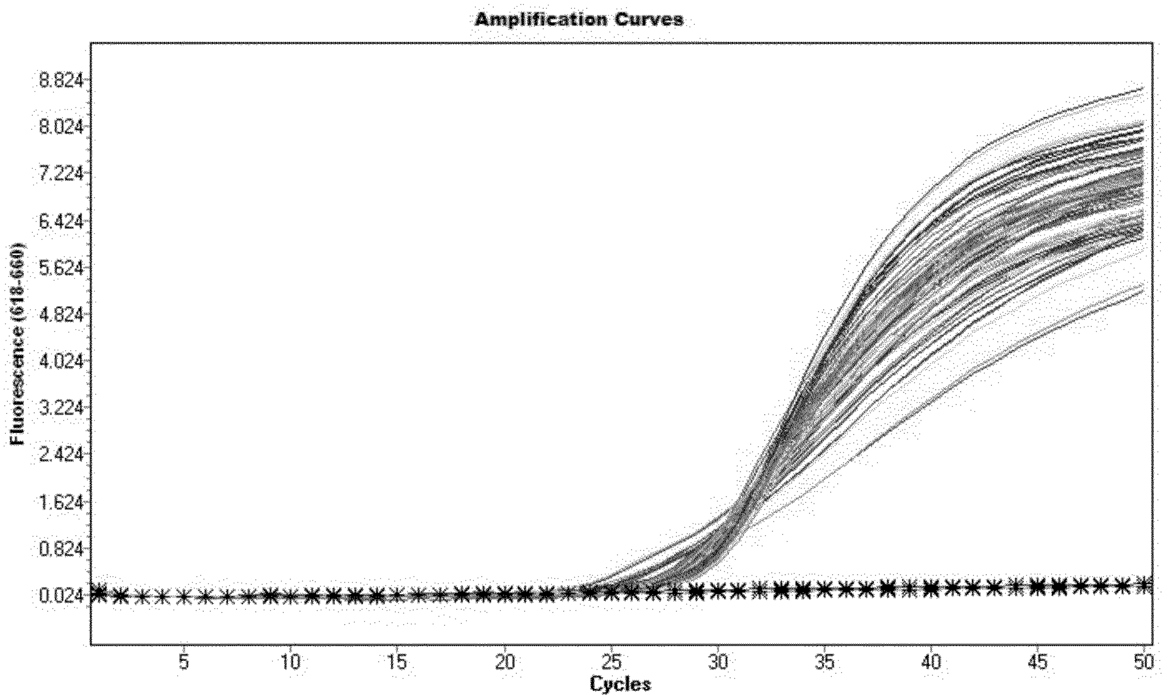

As demonstrated in FIG. 2(*a*), all 26 *Legionella pneumophila* strains tested for (Table 2(a)) were detected by the *L. pneumophila* species assay targeting a region of the smpB gene and the no-template control was not detected by the assay. As shown in FIG. 2(*b*), the *L. pneumophila* species assay targeting a region of the smpB gene detected the one *L. pneumophila* isolate tested for and did not detect the 41 other *Legionella* species and other bacteria that were tested for (Table 2(b)).

Example 3

An Internally Controlled Multiplex Real-Time PCR for the Detection and Identification of *Legionella* Species, *Legionella pneumophila* (Serogroup 1-16) and *Legionella pneumophila* Serogroup 1

Diagnostic Target Identification

A number of housekeeping genes which are highly conserved throughout the *Legionella* genus were evaluated to identify, in silico, a potential diagnostic target which could be used to detect all members of this genus and for the detection of *Legionella pneumophila* strains. The optimal diagnostic target chosen in this study for detection of the *Legionella* genus was the ssrA gene. The ssrA gene codes for tmRNA and has been identified in all bacterial species. The function of tmRNA in bacteria is to rescue stalled ribosomes and to clear the cell of incomplete polypeptides. In silico alignment of publically available nucleotide sequences indicated that while sufficient nucleotide sequence heterogeneity exists between different *Legionella* species, sufficient nucleotide sequence similarity existed to design genus oligonucleotide primers and probes.

In this example, the following exemplary real-time PCR assay primers and probe for the ssrA gene nucleotide sequence (SEQ ID NO. 5) were used: ssrA forward primer (SEQ ID NO. 10), ssrA reverse primer (SEQ ID NO. 11), ssrA probe (SEQ ID NO. 12). The ssrA probe (SEQ ID NO. 12) comprised at least one marker, optionally at least one dye, optionally at least one fluorophore, optionally fluorescein (5' 6-FAM, Integrated DNA Technologies). Optionally, the ssrA probe (SEQ ID NO. 12) comprised at least one fluorescence quenching dye, optionally an internal quencher (ZEN™ quencher, Integrated DNA Technologies), optionally a terminal quencher (3' Iowa Black® FQ, Integrated DNA Technologies; or Black Hole Quencher 1®, LGC Biosearch).

By in silico alignment, it was demonstrated that there is perfect, or near-perfect, conservation of the each of the following nucleotide sequences: the exemplary ssrA forward primer (SEQ ID NO. 10), the exemplary ssrA reverse primer (SEQ ID NO. 11), and the exemplary ssrA probe (SEQ ID NO. 12); among the ssrA gene nucleotide sequences of the following *Legionella* species: *L. pneumophila*ATCC43290, *L. pneumophila*_ThunderBay, *L. pneumophila*_HL06041035, *L. pneumophila*_str.Philadelphia, *L. pneumophila*_Lens, *L. pneumophila*_Paris, *L. pneumophila*_Corby, *L. pneumophila*_2300/99Alcoy, *L. pneumophila*_ Lorraine, *L. longbeachae*D-4968, *L. longbeachae*NSW150, *L. fallonii*_LLAP-10, *L. hackeliae*_LHA, *L. oakridgensis*_ATCC33761 *L. micdadei*_LMI, *L. sainthelensi*_ ATCC35248, *L. wadsworthii*DSM21896, *L. cherrii*_DSM19213, *L. moravica*DSM19234, *L. norrlandica, L. shakespearei*DSM23087, *L. drancourtii*LLAP12 *L. lansingensis*_DSM19556, *L. fairfieldensis*_ATCC_49588, *L. massiliensis*_PRJEB110, and *L. geestiana*DSM21217.

The optimal diagnostic target chosen in this study for detection of the *Legionella pneumophila* was the smpB gene. The smpB gene encodes the RNA binding protein Small Protein B (SmpB) and has been identified in all bacterial species to date. It is considered an essential component of quality control in bacteria as it facilitates the binding of tmRNA to stalled ribosomes which in turn allows for the removal of incomplete polypeptides from the cell. In silico alignment of publically available nucleotide sequences indicated that sufficient nucleotide sequence similarity exists between different serogroups of *Legionella pneumophila* to allow for the design of species specific oligonucleotide primers and probes.

In this example, the following exemplary real-time PCR assay primers and probe for the smpB gene nucleotide sequence (SEQ ID NO. 6) were used: smpB forward primer (SEQ ID NO. 7), smpB reverse primer (SEQ ID NO. 8), smpB probe (SEQ ID NO. 9). Optionally an alternative smpB reverse primer (SEQ ID No. 13) could be used. The smpB probe (SEQ ID NO. 9) comprised at least one marker, optionally at least one dye, optionally at least one fluorophore, optionally rhodamine (5' ROX, Integrated DNA Technologies). Optionally, the smpB probe (SEQ ID NO. 9) comprised at least one fluorescence quenching dye, optionally a terminal quencher (3' Iowa Black® RQ, Integrated DNA Technologies; or Black Hole Quencher 2®, LGC Biosearch).

By in silico alignment, it was demonstrated that there is perfect, or near-perfect, conservation of the each of the following nucleotide sequences: the exemplary smpB forward sequencing primer (SEQ ID NO. 14), the exemplary smpB forward primer (SEQ ID NO. 7), the exemplary smpB reverse sequencing primer (SEQ ID NO. 15), the exemplary smpB reverse primer (SEQ ID NO. 8), and the exemplary smpB probe (SEQ ID NO. 9); among the smpB nucleotide sequences of the following *Legionella* species: *L. pneumophila*_Paris, *L. pneumophila*_Corby, *L. pneumophila*_Pneu, *L. pneumophila*_Lens, *L. pneumophila*_Alcoy, *L. pneumophila*_2868, *L. pneumophila*_3140, *L. pneumophila*_3194, *L. pneumophila*_00189, *L. pneumophila*_2829, *L. pneumophila*_NCTC11986, *L. pneumophila*_NCTC12000, *L. pneumophila*_NCTC12179, *L. pneumophila*_DSM7513, *L. pneumophila*DSM7514, *L. pneumophila*DSM7515, *L. pneumophila*_NCTC11191, *L. pneumophila*_NCTC11230, *L. pneumophila*_NCTC11232, *L. pneumophila*_NCTC11287, *L. pneumophila*_NCTC11984, *L. pneumophila*_NCTC11985.

Based on the evaluation of housekeeping genes performed in this study, it was not possible to identify a *Legionella pneumophila* serogroup 1 specific target. As such whole genome comparisons were performed to identify a novel diagnostics target in silico. Publicly available whole genome sequence information was retrieved from the National Center for Biotechnology Information website (www.ncbi.nlm.nih.gov/) for *Legionella pneumophila* serogroup 1 and *Legionella pneumophila* serogroup 6 and serogroup 12. Regions potentially unique to *L. pneumophila* serogroup 1 were identified using WEBACT (www.webact.org/). This resulted in a number of regions of difference in *L. pneumophila* serogroup 1. Each identified putative target nucleotide sequence was BLAST analysed (blast.ncbi.nlm.nih.gov/Blast.cgi) to determine if they were present in all *L. pneumophila* serogroup 1 and absent in all other *L. pneumophila* serogroups or closely related *Legionella* species. One region was present in all *L. pneumophila* serogroup 1 analysed with very low or no sequence similarity to other *L. pneumophila* serogroups or closely related *Legionella* species. This region was the lpg0768 gene (SEQ ID NOs 1 and 21-48) which encodes the spore coat polysaccharide biosynthesis protein E, NeuB. Closely related nucleotide sequences from *Legionella pneumophila* serogroup 1 strains were aligned using ClustalW (www.ebi.ac.uk/Tools/msa/clustalw2/).

By in silico alignment, it was demonstrated that there is partial, perfect, or near-perfect, conservation of the each of the following nucleotide sequences: the exemplary lpg0768forward sequencing primer (SEQ ID NO. 16), the exemplary lpg0768 forward primer (SEQ ID NO. 2), the exemplary lpg0768 reverse sequencing primer (SEQ ID NO. 17), the exemplary lpg0768 reverse primer (SEQ ID NO. 3), and the exemplary lpg0768 probe (SEQ ID NO. 4); among the lpg0768 nucleotide sequences of the following *Legionella pneumophila* serogroup 1 strains: gi|395129037 *L. pneumophila*_extended, *L. pneumophila*_str.Philadelphia1 (sg1), *L. pneumophila*_str.Paris(sg1), *L. pneumophila*_LPE509(SG1), gi|6688579 *L. pneumophila*(sg1), *L. pneumophila*_str.Lens(sg1), gi|410173912 *L. pneumophila*(sg1), *L. pneumophila*_str.Camperdown1(sg1), *L. pneumophila*_str.Heysham1(sg1), *L. pneumophila*_strUppsala3(sg1), *L. pneumophila*2300/99Alcoy(sg1), *L. pneumophila*_str.Corby (sg1), *L. pneumophila*_str.uppsala3.b(sg1), *L. pneumophila*_str.Lorraine(sg1), *L. pneumophila*_str.Goerlitz6543 (sg1), *L. pneumophila*_str.HL06041035(sg1), *L. pneumophila*_str.Hextuple_3a(sg1), *L. pneumophila*_str.Hextuple_2q(sg1), *L. pneumophila*(sg1)_DSM7513, *L. pneumophila*(sg1)_NCTC11191, *L. pneumophila*(sg1)_NCTC11231, *L. pneumophila*(sg 1)_NCTC11378, *L. pneumophila*(sg1)_NCTC11404, *L. pneumophila*(sg1)_DSM25019, *L. pneumophila*(sg1)_DSM25021, *L. pneumophila*(sg1)_DSM25199, *L. pneumophila*(sg1)_DSM25200, *L. pneumophila*(sg1)_DSM25213, and *L. pneumophila*(sg1)_DSM37564.

Bacterial Strains, Culture Media, and Growth Conditions

A panel of 26 *Legionella pneumophila* strains and 41 other *Legionella* species were used in this study (Tables 2.1 and 2.2). These species and strains were purchased from the German Collection of Microorganisms and Cell Cultures (Deutsche Sammlung von Mikroorganismen und Zellkulturen GmbH, DSMZ. Braunschweig, Germany), the National Collection of Type Cultures (NCTC, Public Health England, Salisbury, United Kingdom), American Type Culture Collection (ATCC, provided by LGC standards, Middlesex United Kingdom) and Culture Collection, University of Göteborg, (CCUG, Sweden). All *Legionella* species and strains were cultured on BCYE media at 37° C. for 18-24 hours or until sufficient growth was observed.

Genomic DNA Isolation and Quantification.

Genomic DNA from *Legionella* cultures were isolated using a modified procedure combining mechanical lysis (IDI lysis kit; Becton Dickenson, Canada) and purification using a DNA purification kit (quick gDNA kit; Zymo Research, Irvine, CA, USA). Briefly, a loop of culture was resuspended in 250 μl lysis buffer (IDI lysis buffer). The suspension was transferred to a cell lysis tube (GeneOhm) and bead beaten (Mini-Bead-Beater-16; Stratech, United Kingdom) for 3 minutes. After bead beating, 200 μl was transferred to a nucleic acid purification spin column (Zymo-Spin™ Column) in a collection tube and steps 2 to 5 of the procedure for purification of total DNA from cell suspensions were followed, according to the manufacturers instructions.

Nucleotide Sequencing

To generate partial smpB nucleotide sequence for *L. pneumophila*, conventional PCR was performed using the sequencing primers outlined in Table 3(a) on a thermal cycler (iCycler iQ thermal cycler; Bio-Rad Laboratories Inc., California, USA). All reactions were carried out in a final volume of 50 μl, containing 5 μl 10× buffer (15 mM $MgCl_2$), 1 μl forward and reverse primers (0.2 μM final conc.), 2 μl DNA polymerase (Taq; 1 U/μl, Roche Diagnostics, Basel, Switzerland), 1 μl dNTP mix (10 mM deoxynucleoside triphosphate set; Roche Diagnostics), 5 μl of template DNA and 35 μl nuclease free water (Applied Biosystems/Ambion, Texas, USA). The cycling parameters consisted of initial denaturation at 95° C. for 5 minutes, followed by 35 cycles of denaturation at 95° C. (1 minutes), annealing at 50° C. (1 minutes), and extension at 72° C. (1 minutes), with a final elongation step at 72° C. for 10 minutes.

TABLE 3(a)

Oligonucleotides used in this study

| Name | Target gene | Function | 5'-3' Sequence | SEQ ID NO. |
|---|---|---|---|---|
| LegGen-F1 | ssrA | Genus real-time PCR assay forward primer | GGCGACCTGGCTTC | 10 |
| LegGen-R1 | ssrA | Genus real-time PCR assay reverse primer | TATGACCGTTGATTCGATACC | 11 |
| LegGen-P1 | ssrA | Genus real-time PCR assay probe | /56-FAM/ACGTGGGTT/ZEN/GCRAAACC/3IABkFQ/ | 12 |
| LgensmpB_F | smpB | *L. pneumophila* forward Seqeuncing primer | GATCAATACGAAGCAGGC | 14 |

TABLE 3(a)-continued

| Name | Target gene | Function | 5'-3' Sequence | SEQ ID NO. |
|---|---|---|---|---|
| Oligonucleotides used in this study | | | | |
| LgensmpB_R | smpB | *L. pneumophila* reverse Seqeuncing primer | GCCATTCTCTGTCTTTGATC | 15 |
| LegPneuF1 | smpB | *L. pneumophila* real-time PCR assay forward primer | CACGTGATAATMAAATACGGT | 7 |
| LegPneuR1 | smpB | *L. pneumophila* real-time PCR assay reverse primer | TTCATCAATAGCTTGCGYG | 8 |
| LegPneuR12 | smpB | *L. pneumophila* real-time PCR assay reverse primer 2 | TTCATCAACAGCTTGCGTG | 13 |
| LegPneuP1 | smpB | *L. pneumophila* real-time PCR assay probe | /56-ROXN/CYGCATCCACTCA TTTTATTCCTGAT/3IAbRQSp/ | 9 |
| L.pneu(sg1)_Fseq | region 5' lpg0768 | *L. pneumophila* sg1 forward Seqeuncing primer | CCAAGTAGGGTTTCTAACAATC | 16 |
| L.pneu(sg1)_Rseq | region 3' lpg0768 | *L. pneumophila* sg1 reverse Seqeuncing primer | GAGTCAGCCTTTTACAATTGG | 17 |
| L.pneu(sg1)_F | lpg0768 | *L. pneumophila* sg1 real-time PCR assay forward primer | AGCTCCCAATGCAATAGAC | 2 |
| L. pneu(sg1)_R | lpg0768 | *L. pneumophila* sg1 real-time PCR assay reverse primer | GCAAAGCAGTTGAAACAGC | 3 |
| L. pneu(sg1)_P | lpg0768 | *L. pneumophila* sg1 real-time PCR assay probe | /5HEX/CCAACTGGT/ZEN/ AATGAAAAACATTGGT/3IABkFQ/ | 4 |
| SIACF1 | synthetic construct | IAC real-time PCR assay forward primer | ATGCCAGTCAGCATAAGGA | 18 |

TABLE 3(a)-continued

Oligonucleotides used in this study

| Name | Target gene | Function | 5'-3' Sequence | SEQ ID NO. |
|---|---|---|---|---|
| SIACF2 | synthetic construct | IAC real-time PCR assay reverse primer | CAGACCTCTGGTAGGATGTAC | 19 |
| SIACP1 | synthetic construct | IAC real-time PCR probe | 5Cy5/TCGGCACTA/TAO/ CCGACACGAAC/3IAbRQSp/ | 20 |

/56-FAM/ = 5' 6-FAM (fluorescein) fluorophore;
/ZEN/ = ZEN ™ internal quencher, made by Integrated DNA Technologies;
/3IABkFQ/ = 3' Iowa Black ® FQ terminal quencher, made by Integrated DNA Technologies;
/56-ROXN/ = 5' ROX (carboxy-X-rhodamine) n-hydroxysuccinimide ester fluorophore;
/5HEX/ = 5' HEX (hexachlorofluorescein) fluorophore;
/5Cy5/ = 5' Cy5 (cyanine) fluorophore;
/TAO/ = TAO ™ internal quencher, made by Integrated DNA Technologies;
/3IAbRQSp/ = 3' Iowa Black ® RQ terminal quencher, made by Integrated DNA Technologies.

To generate the lpg0768 gene nucleotide sequence for *L. pneumophila* serogroup 1 strains, conventional PCR was performed using the sequencing primers outlined in Table 3(a) on the thermal cycler (iCycler iQ thermal cycler; Bio-Rad Laboratories Inc., California, USA). All reactions were carried out in a final volume of 50 µl, containing 5 µl 10× buffer (15 mM $MgCl_2$), 1 µl forward and reverse primers (0.2 µM final conc.), 2 µl DNA polymerase (Taq; 1 U/µl, Roche Diagnostics, Basel, Switzerland), 1 µl dNTP mix (10 mM deoxynucleoside triphosphate set; Roche Diagnostics), 5 µl of template DNA and 35 µl nuclease free water (Applied Biosystems/Ambion, Texas, USA). The cycling parameters consisted of initial denaturation at 95° C. for 5 minutes, followed by 35 cycles of denaturation at 95° C. (1 minutes), annealing at 50° C. (1 minutes), and extension at 72° C. (1 minutes), with a final elongation step at 72° C. for 10 minutes.

PCR products were visualised on a 1.5% agarose gel and subsequently purified using a PCR product purification kit (High Pure Product Purification Kit; Roche Diagnostics). Purified PCR products were sent for sequencing externally (Sequiserve, Vaterstetten, Germany).

Assay Design

All oligonucleotide primers and probes used in this example were designed in accordance with published guidelines. All oligonucleotide primers and probes were purchased from Integrated DNA Technologies (Leuven, Belgium).

Development of an Internal Amplification Control (IAC) for Real-Time PCR

An internal amplification control (IAC) was designed and incorporated in the multiplex assay designed to monitor for PCR inhibition, thermocycler malfunction, degradation of assay components etc. As this multiplex assay is designed for use on environmental samples, a synthetic construct of random sequence was identified to be the most suitable IAC. The synthetic construct sequence is not found in nature and as such the specific oligonucleotide primers and probes will not be mopped up by competing microorganisms commonly found in the environment.

In this example, the following exemplary real-time PCR assay primers and probe for the IAC were used: IAC synthetic construct forward primer (SEQ ID NO. 18), IAC synthetic construct reverse primer (SEQ ID NO. 19), IAC synthetic construct probe (SEQ ID NO. 20). The IAC synthetic construct probe (SEQ ID NO. 20) comprised at least one marker, optionally at least one dye, optionally at least one fluorophore, optionally cyanine (5' Cy5™, Integrated DNA Technologies). Optionally, the synthetic construct probe (SEQ ID NO. 20) comprised at least one fluorescence quenching dye, optionally an internal quencher (TAO™ quencher, Integrated DNA Technologies), optionally a terminal quencher (3' Iowa Black® RQ, Integrated DNA Technologies).

Titrations of synthetic DNA were performed to determine the optimum concentration of IAC target per reaction such that the IAC is always detected without impacting on detection of the primary *Legionella* targets in the multiplex. An internal control concentration of 1000 genome equivalents per reaction allowed for the detection of the IAC all real-time PCR experiments performed.

A multiplex PCR assay was produced using a combination of oligonucleotide primers and probes selected from: the oligonucleotide primers and probes listed in Table 3(a), and the oligonucleotide primers and probes described in example 1, the oligonucleotide primers and probes described in example 2, and the oligonucleotide primers and probes for the IAC synthetic construct described in this example.

Real-Time PCR

To determine the specificity of each of the diagnostics target used in this study, Monoplex real-time PCR was performed on a thermal cycler (LightCycler 480; Roche Diagnostics, Basel, Switzerland) using a probes kit (LightCycler® Probes Master kit; Roche Diagnostics). A final volume of 20 µl was used in each reaction, containing 2× PCR reaction master mixture (master mix) [LightCycler 480 Probes Master (6.4 mM $MgCl_2$)], forward and reverse primer (0.5 mM final conc.), FAM, HEX, ROX or CY5 labelled probe (0.2 mM final conc.), template DNA (2 µl) and the volume adjusted to 20 µl with the addition of nuclease free $dH_2O$. The cycling parameters consisted of incubation for 10 minutes at 95° C. to activate enzymes and DNA denaturation followed by 50 cycles of 95° C. for 10 seconds and 60° C. for 30 s, followed by a cooling step at 40° C. for 10 s. The temperature transition rate for all cycling steps was 4.4° C./s while heating and 2.2° C./s while cooling.

Multiplex real-time PCR reactions were carried out on a thermal cycler (LightCycler 480; Roche Diagnostics, Basel, Switzerland) using a probes kit (LightCycler® Probes Master kit; Roche Diagnostics). A final volume of 20 μl was used for each multiplex experiment. The optimised master mix contained 2× PCR reaction master mixture [LightCycler 480 Probes Master (6.4 mM $MgCl_2$)], forward and reverse primer (0.125-0.25 mM final conc.), FAM, HEX, ROX and CY5 labelled dyes (0.2-0.4 μM final conc.), template DNA (5 μl), IAC DNA 1 μl, and the volume adjusted to 20 μl with the addition of nuclease free $dH_2O$. The internal control DNA was diluted to contain 1000 genome equivalents per μl and all other DNAs were tested at a range of 10*3-10*4 genome equivalents per 5 μl. The cycling parameters used were the same as those used in a monoplex format outlined above. A colour compensation file was generated using the technical note outlined in the Advanced Software Functionalities of the operator manual.

Sensitivity and Specificity of the Real-Time PCR Assays

The specificity of each real-time PCR assay was confirmed both in monoplex and multiplex formats using the specificity panel listed in Table 3(b) and Table 3(c). Using the multiplex assay, all of the *Legionella* strains were detected in the *Legionella* genus assay targeting a region of the ssrA gene. A representation of this can be seen in FIG. 3(*a*), in which the negative control is represented by a line marked with stars. The *L. pneumophila* serogroup 1 specific assay targeting a region of the lpg0768 gene was specific for the detection of *L. pneumophila* serogroup 1 isolates. A representation of this can be seen in FIG. 3(*b*), in which the 12 *L. pneumophila* serogroup 1 strains tested are represented by lines marked with circles. All 12 *L. pneumophila* serogroup 1 strains were detected by the assay. The *L. pneumophila* species assay targeting a region of the smpB gene was specific for the detection of the 26 *L. pneumophila* strains tested for and the 41 other *Legionella* species were not detected by this assay. A representation of this can be seen in FIG. 3(*c*), in which the negative control is represented by a line marked with stars. The specificity of the IAC assay was tested using the full specificity panel (Table 3(b) and Table 3(c)) and was specific for the synthetic construct. As the IAC assay is designed using a non-competitive approach, when spiked into the master mix a positive signal should always be observed in the Cy5 channel. A representation of this can be seen in FIG. 3(*d*), in which the no template control is represented by a line marked with stars. The analytical specificity of this multiplex real-time PCR assay is 100%.

To determine the sensitivity of the multiplex real-time PCR assay developed, serial dilutions ranging from 10*4-1 cell equivalent of *L. pneumophila* were tested in triplicate. The limit of detection of the multiplex assay is between 1-10 genome equivalents.

TABLE 3(b)

*Legionella pneumophila* strains used in this study

| Strain | Culture collection | Number | Serogroup |
|---|---|---|---|
| *Legionella pneumophila* | DSM | 7513 | 1 |
| *Legionella pneumophila* | NCTC | 11191 | 1 |
| *Legionella pneumophila* | NCTC | 11231 | 1 |
| *Legionella pneumophila* | NCTC | 11286 | 1 |
| Legionella pneumophila | NCTC | 11378 | 1 |
| *Legionella pneumophila* | NCTC | 11404 | 1 |
| *Legionella pneumophila* | DSM | 25019 | 1 |
| *Legionella pneumophila* | DSM | 25021 | 1 |

TABLE 3(b)-continued

*Legionella pneumophila* strains used in this study

| Strain | Culture collection | Number | Serogroup |
|---|---|---|---|
| *Legionella pneumophila* | DSM | 25199 | 1 |
| *Legionella pneumophila* | DSM | 25200 | 1 |
| *Legionella pneumophila* | DSM | 25213 | 1 |
| *Legionella pneumophila* | DSM | 27564 | 1 |
| *Legionella pneumophila* | NCTC | 11230 | 2 |
| *Legionella pneumophila* | NCTC | 11232 | 3 |
| *Legionella pneumophila* | DSM | 7414 | 4 |
| *Legionella pneumophila* | DSM | 7415 | 5 |
| *Legionella pneumophila* | NCTC | 11417 | 5 |
| *Legionella pneumophila* | NCTC | 11287 | 6 |
| *Legionella pneumophila* | NCTC | 11984 | 7 |
| *Legionella pneumophila* | NCTC | 11985 | 8 |
| *Legionella pneumophila* | NCTC | 11986 | 9 |
| *Legionella pneumophila* | NCTC | 12000 | 10 |
| *Legionella pneumophila* | NCTC | 12179 | 11 |
| *Legionella pneumophila* | NCTC | 12180 | 12 |
| *Legionella pneumophila* | NCTC | 12181 | 13 |
| *Legionella pneumophila* | NCTC | 12174 | 14 |

DSM = The German Collection of Microorganisms;
NCTC = National Collection of Type Cultures TABLE 3(c)

Other *Legionella* species tested in this study

| Strain | Source |
|---|---|
| *Legionella anisa* | DSM 17627 |
| *Legionella birminghamensis* | DSM 19232 |
| *Legionella birminghamensis* | ATCC 700709 |
| *Fluoribacter bozemanae* (*Legionella bozemanii*) | DSM 16523 |
| *Fluoribacter bozemanae*-2 | NCTC 11975 |
| *Legionella cincinnatiensis* | DSM 19233 |
| *Fluoribacter dumoffii* (*Legionella dumoffii*) | DSM 17625 |
| *Fluoribacter dumoffii* | ATCC 33343 |
| *Legionella erythra* | DSM 17644 |
| *Legionella feeleii*-1 | DSM 17645 |
| *Legionella feeleii*-2 | NCTC 11978 |
| *Flouribacter gormanii* (*Legionella gormanii*) | DSM 16641 |
| *Fluoribacter gormanii* | ATCC 43769 |
| *Legionella hackeliae*-1 | DSM 19214 |
| *Legionella hackeliae*-2 | NCTC 11980 |
| *Legionella jordanis* | DSM 19212 |
| *Legionella jordanis* | ATCC 700762 |
| *Legionella lansingensis* | DSM 19556 |
| *Legionella longbeachae*-1 | DSM 10572 |
| *Legionella maceachwerii* | DSM 10572 |
| *Tatlockia micdadei* (*Legionella micdadei*) | NCTC 11403 |
| *Legionella oakridgensis* | NCTC 11531 |
| *Legionella oakridgensis* | ATCC 700515 |
| *Legionella parisiensis* | DSM 19216 |
| *Legionella wadsworthii* | NCTC 11532 |
| *Legionella adelaidensis* | DSM 19888 |
| *Legionella brunensis* | DSM 19236 |
| *Legionella busanesis* | ATCC-BAA518 |
| *Legionella cherrii* | DSM 19213 |
| *Legionella donaldsonii* | ATCC BAA-693 |
| *Legionella fairfieldensis* | NCTC 12488 |
| *Legionella fallonii* | CCUG 43887 |
| *Legionella gratiana* | DSM 21233 |
| *Legionella gresilensis* | DSM 21218 |
| *Legionella israelensi* | DSM 19235 |
| *Legionella jamestowniensis* | DSM 19215 |
| *Legionella londoniensis* | DSM 21234 |
| *Legionella moravica* | DSM 19234 |
| *Legionella quinlivanii*-1 | NCTC 12433 |
| *Legionella rubrilicens* | DSM 11884 |
| *Legionella taurinsis* | CCUG 44901 |

DSM = The German Collection of Microorganisms;
ATCC = American Type Culture Collection;
NCTC = National Collection of Type Cultures;
CCUG = Culture Collection, University of Göteborg Example 5

Diagnostics Algorithm

For determining which *Legionella* species and/or strains are present in a sample, the user must take into account the combination of results observed for each channel of the real-time in vitro amplification instrument. This are set out in Table 4 below, and explained below.

TABLE 4

Result of multiplex PCRs associated with each diagnosis

| Test | Multiplex 1 | | | | |
|---|---|---|---|---|---|
| (Target) | (ssrA) | (lpg0768) | (smpB) | (IAC) | |
| | • | • | • | • | *Legionella pneumophila* serogroup 1 |
| | • | X | • | • | *Legionella pneumophila* serogroup 2-16 |
| | • | X | X | • | *Legionella* species other than *Legionella pneumophila* |
| | X | X | X | • | *Legionella* species not present |
| | X | X | X | X | Result invalid |

Key:
• = positive signal,
X = not detected

Example 6

An Internally Controlled Multiplex Real-Time PCR for the Detection and Identification of *Legionella* Species, *Legionella pneumophila* (Serogroup 1-16) and *Legionella pneumophila* Serogroup 1

Diagnostic Target Identification

A number of housekeeping genes which are highly conserved throughout the *Legionella* genus were evaluated to identify, in silico, a potential diagnostic target which could be used to detect all members of this genus and for the detection of *Legionella pneumophila* strains. The optimal diagnostic target chosen in this study for detection of the *Legionella* genus was the ssrA gene. The ssrA gene codes for tmRNA and has been identified in all bacterial species. The function of tmRNA in bacteria is to rescue stalled ribosomes and to clear the cell of incomplete polypeptides. In silico alignment of publically available nucleotide sequences indicated that while sufficient nucleotide sequence heterogeneity exists between different *Legionella* species, sufficient nucleotide sequence similarity existed to design genus oligonucleotide primers and probes.

In this example, the following exemplary real-time PCR assay primers and probe for the ssrA gene nucleotide sequence (SEQ ID NO. 5) were used: ssrA forward primer (SEQ ID NO. 10), ssrA reverse primer (SEQ ID NO. 11), ssrA probe (SEQ ID NO. 12). The ssrA probe (SEQ ID NO. 12) comprised at least one marker, optionally at least one dye, optionally at least one fluorophore, optionally fluorescein (5' 6-FAM, Integrated DNA Technologies). Optionally, the ssrA probe (SEQ ID NO. 12) comprised at least one fluorescence quenching dye, optionally an internal quencher (ZEN™ quencher, Integrated DNA Technologies), optionally a terminal quencher (3' Iowa Black® FQ, Integrated DNA Technologies; or Black Hole Quencher 1®, LGC Biosearch).

By in silico alignment, it was demonstrated that there is perfect, or near-perfect, conservation of the each of the following nucleotide sequences: the exemplary ssrA forward primer (SEQ ID NO. 10), the exemplary ssrA reverse primer (SEQ ID NO. 11), and the exemplary ssrA probe (SEQ ID NO. 12); among the ssrA gene nucleotide sequences of the following *Legionella* species: *L. pneumophila*ATCC43290, *L. pneumophila*_ThunderBay, *L. pneumophila*_HL06041035, *L. pneumophila*_str.Philadelphia, *L. pneumophila*_Lens, *L. pneumophila*_Paris, *L. pneumophila*_Corby, *L. pneumophila*_2300/99Alcoy, *L. pneumophila*_Lorraine, *L. longbeachae*D-4968, *L. longbeachae*NSW150, *L. fallonii*_LLAP-10, *L. hackeliae*_LHA, *L. oakridgensis*_ATCC33761 *L. micdadei*_LMI, *L. sainthelensi*_ATCC35248, *L. wadsworthii*DSM21896, *L. cherrii*_DSM19213, *L. moravica*DSM19234, *L. norrlandica, L. shakespearei*DSM23087, *L. drancourtii*LLAP12 *L. lansingensis*_DSM19556, *L. fairfieldensis*_ATCC_49588, *L. massiliensis*_PRJEB110, and *L. geestiana*DSM21217.

The optimal diagnostic target chosen in this study for detection of the *Legionella pneumophila* was the smpB gene. The smpB gene encodes the RNA binding protein Small Protein B (SmpB) and has been identified in all bacterial species to date. It is considered an essential component of quality control in bacteria as it facilitates the binding of tmRNA to stalled ribosomes which in turn allows for the removal of incomplete polypeptides from the cell. In silico alignment of publically available nucleotide sequences indicated that sufficient nucleotide sequence similarity exists between different serogroups of *Legionella pneumophila* to allow for the design of species specific oligonucleotide primers and probes.

In this example, the following exemplary real-time PCR assay primers and probe for the smpB gene nucleotide sequence (SEQ ID NO. 6) were used: smpB forward primer (SEQ ID NO. 49), smpB reverse primer (SEQ ID NO. 50), smpB probes (SEQ ID NO. 51 and SEQ ID NO. 52). The smpB probes (SEQ ID NO. 51 and SEQ ID NO. 52) comprised at least one marker, optionally at least one dye, optionally at least one fluorophore, optionally rhodamine (5' ROX, Integrated DNA Technologies). Optionally, the smpB probes (SEQ ID NO. 51 and SEQ ID NO. 52) comprised at least one fluorescence quenching dye, optionally a terminal quencher (3' Iowa Black® RQ, Integrated DNA Technologies; or Black Hole Quencher 2®, LGC Biosearch).

By in silico alignment, it was demonstrated that there is perfect, or near-perfect, conservation of the each of the following nucleotide sequences: the exemplary smpB forward sequencing primer (SEQ ID NO. 14), the exemplary smpB forward primer (SEQ ID NO. 49), the exemplary smpB reverse sequencing primer (SEQ ID NO. 15), the exemplary smpB reverse primer (SEQ ID NO. 50), and the exemplary smpB probes (SEQ ID NO. 51 and SEQ ID NO. 52); among the smpB nucleotide sequences of the following *Legionella* species: *L. pneumophila*_Paris, *L. pneumophila*_Corby, *L. pneumophila*_Pneu, *L. pneumophila*_Lens, *L. pneumophila*_Alcoy, *L. pneumophila*_2868, *L. pneumophila*_3140, *L. pneumophila*_3194, *L. pneumophila*_00189, *L. pneumophila*_2829, *L. pneumophila*_NCTC11986, *L. pneumophila*_NCTC12000, *L. pneumophila*_NCTC12179, *L. pneumophila*_DSM7513, *L. pneumophila*DSM7514, *L. pneumophila*DSM7515, *L. pneumophila*_NCTC11191, *L. pneumophila*_NCTC11230, *L. pneumophila*_NCTC11232, *L. pneumophila*_NCTC11287, *L. pneumophila*_NCTC11984, *L. pneumophila*_NCTC11985.

Based on the evaluation of housekeeping genes performed in this study, it was not possible to identify a *Legionella*

*pneumophila* serogroup 1 specific target. As such whole genome comparisons were performed to identify a novel diagnostics target in silico. Publicly available whole genome sequence information was retrieved from the National Center for Biotechnology Information website (www.ncbi.nlm-.nih.gov/) for *Legionella pneumophila* serogroup 1 and *Legionella pneumophila* serogroup 6 and serogroup 12. Regions potentially unique to *L. pneumophila* serogroup 1 were identified using WEBACT (www.webact.org/). This resulted in a number of regions of difference in *L. pneumophila* serogroup 1. Each identified putative target nucleotide sequence was BLAST analysed (blast.ncbi.nlm.nih.gov/Blast.cgi) to determine if they were present in all *L. pneumophila* serogroup 1 and absent in all other *L. pneumophila* serogroups or closely related *Legionella* species. One region was present in all *L. pneumophila* serogroup 1 analysed with very low or no sequence similarity to other *L. pneumophila* serogroups or closely related *Legionella* species. This region was the lpg0768 gene (SEQ ID NO. 1, 21-49) which encodes the spore coat polysaccharide biosynthesis protein E, NeuB. Closely related nucleotide sequences from *Legionella pneumophila* serogroup 1 strains were aligned using ClustalW (www.ebi.ac.uk/Tools/msa/clustalw2/).

By in silico alignment, it was demonstrated that there is partial, perfect, or near-perfect, conservation of the each of the following nucleotide sequences: the exemplary lpg0768forward sequencing primer (SEQ ID NO. 16), the exemplary lpg0768 forward primer (SEQ ID NO. 2), the exemplary lpg0768 reverse sequencing primer (SEQ ID NO. 17), the exemplary lpg0768 reverse primer (SEQ ID NO. 3), and the exemplary lpg0768 probe (SEQ ID NO. 4); among the lpg0768 nucleotide sequences of the following *Legionella pneumophila* serogroup 1 strains: gi|395129037 *L. pneumophila*_extended, *L. pneumophila*_str.Philadelphia1 (sg 1), *L. pneumophila*_str.Paris(sg 1), *L. pneumophila*_LPE509(SG1), gi|6688579 *L. pneumophila*(sg1), *L. pneumophila*_str.Lens(sg1), gi|410173912 *L. pneumophila*(sg 1), *L. pneumophila*_str.Camperdown1(sg 1), *L. pneumophila*_str.Heysham1(sg1), *L. pneumophila*_strUppsala3(sg1), *L. pneumophila*2300/99Alcoy(sg1), *L. pneumophila*_str.Corby (sg1), *L. pneumophila*_str.uppsala3.b(sg1), *L. pneumophila*_str.Lorraine(sg1), *L. pneumophila*_str.Goerlitz6543 (sg 1), *L. pneumophila*_str. HL06041035(sg 1), *L. pneumophila*_str.Hextuple_3a(sg1), *L. pneumophila*_str.Hextuple_2q(sg1), *L. pneumophila*(sg1)_DSM7513, *L. pneumophila*(sg1)_NCTC11191, *L. pneumophila*(sg1)_NCTC11231, *L. pneumophila*(sg1)_NCTC11378, *L. pneumophila*(sg1)_NCTC11404, *L. pneumophila*(sg1)_DSM25019, *L. pneumophila*(sg1)_DSM25021, *L. pneumophila*(sg1)_DSM25199, *L. pneumophila*(sg1)_DSM25200, *L. pneumophila*(sg1)_DSM25213, and *L. pneumophila*(sg1)_DSM37564.

Bacterial Strains, Culture Media, and Growth Conditions

A panel of 26 *Legionella pneumophila* strains and 41 other *Legionella* species were used in this study (Tables 2.1 and 2.2). These species and strains were purchased from the German Collection of Microorganisms and Cell Cultures (Deutsche Sammlung von Mikroorganismen und Zellkulturen GmbH, DSMZ. Braunschweig, Germany), the National Collection of Type Cultures (NCTC, Public Health England, Salisbury, United Kingdom), American Type Culture Collection (ATCC, provided by LGC standards, Middlesex United Kingdom) and Culture Collection, University of Göteborg, (CCUG, Sweden). All *Legionella* species and strains were cultured on BCYE media at 37° C. for 18-24 hours or until sufficient growth was observed.

Genomic DNA Isolation and Quantification.

Genomic DNA from *Legionella* cultures were isolated using a modified procedure combining mechanical lysis (IDI lysis kit; Becton Dickenson, Canada) and purification using a DNA purification kit (quick gDNA kit; Zymo Research, Irvine, CA, USA). Briefly, a loop of culture was resuspended in 250 μl lysis buffer (IDI lysis buffer). The suspension was transferred to a cell lysis tube (GeneOhm) and bead beaten (Mini-Bead-Beater-16; Stratech, United Kingdom) for 3 minutes. After bead beating, 200 μl was transferred to a nucleic acid purification spin column (Zymo-Spin™ Column) in a collection tube and steps 2 to 5 of the procedure for purification of total DNA from cell suspensions were followed, according to the manufacturers instructions.

Nucleotide Sequencing

To generate partial smpB nucleotide sequence for *L. pneumophila*, conventional PCR was performed using the sequencing primers outlined in Table 5(a) on a thermal cycler (iCycler iQ thermal cycler; Bio-Rad Laboratories Inc., California, USA). All reactions were carried out in a final volume of 50 μl, containing 5 μl 10× buffer (15 mM $MgCl_2$), 1 μl forward and reverse primers (0.2 μM final conc.), 2 μl DNA polymerase (Taq; 1 U/μl, Roche Diagnostics, Basel, Switzerland), 1 μl dNTP mix (10 mM deoxynucleoside triphosphate set; Roche Diagnostics), 5 μl of template DNA and 35 μl nuclease free water (Applied Biosystems/Ambion, Texas, USA). The cycling parameters consisted of initial denaturation at 95° C. for 5 minutes, followed by 35 cycles of denaturation at 95° C. (1 minutes), annealing at 50° C. (1 minutes), and extension at 72° C. (1 minutes), with a final elongation step at 72° C. for 10 minutes.

TABLE 5(a)

Oligonucleotides used in this study

| Name | Target gene | Function | 5'-3' Sequence | SEQ ID NO. |
|---|---|---|---|---|
| LegGen-F1 | ssrA | Genus real-time PCR assay forward primer | GGCGACCTGGCTTC | 10 |
| LegGen-R1 | ssrA | Genus real-time PCR assay reverse primer | TATGACCGTTGATTCGATACC | 11 |

TABLE 5(a)-continued

Oligonucleotides used in this study

| Name | Target gene | Function | 5'-3' Sequence | SEQ ID NO. |
|---|---|---|---|---|
| LegGen-P1 | ssrA | Genus real-time PCR assay probe | /56-FAM/ACGTGGGTT/ZEN/ GCRAAACC/3IABkFQ/ | 12 |
| LgensmpB_F | smpB | *L. pneumophila* forward Seqeuncing primer | GATCAATACGAAGCAGGC | 14 |
| LgensmpB_R | smpB | *L. pneumophila* reverse Seqeuncing primer | GCCATTCTCTGTCTTTGATC | 15 |
| Legionella sg1-16 F2 | smpB | *L. pneumophila* real-time PCR assay forward primer | GATCAATACGAAGCAGGC | 49 |
| Legionella sg1-16 R2 | smpB | *L. pneumophila* real-time PCR assay reverse primer | CCTTGYCTTTCAACACTTCC | 50 |
| Legionella sg1-16 P2 | smpB | *L. pneumophila* real-time PCR assay probe | /56-ROXN/ CATCCACTCATTTTATTCCTGATCC /3IAbRQSp/ | 51 |
| Legionella sg1-16 P3 | smpB | *L. pneumophila* real-time PCR assay probe | /56-ROXN/ CATCTACTCATTTTATTCCTGATCC /3IAbRQSp/ | 52 |
| L. pneu(sg1)_Fseq | region 5' lpg0768 | *L. pneumophila* sg1 forward Seqeuncing primer | CCAAGTAGGGTTTCTAACAATC | 16 |
| L. pneu(sg1)_Rseq | region 3' lpg0768 | *L. pneumophila* sg1 reverse Seqeuncing primer | GAGTCAGCCTTTTACAATTGG | 17 |
| L.pneu(sg1)_F | lpg0768 | *L. pneumophila* sg1 real-time PCR assay forward primer | AGCTCCCAATGCAATAGAC | 2 |
| L. pneu(sg1)_R | lpg0768 | *L. pneumophila* sg1 real-time PCR assay reverse primer | GCAAAGCAGTTGAAACAGC | 3 |
| L. pneu(sg1)_P | lpg0768 | *L. pneumophila* sg1 real- | /5HEX/CCAACTGGT/ZEN/ AATGAAAAACATTGGT/3IABkFQ/ | 4 |

TABLE 5(a)-continued

Oligonucleotides used in this study

| Name | Target gene | Function | 5'-3' Sequence | SEQ ID NO. |
|---|---|---|---|---|
| | | time PCR assay probe | | |
| SIACF1 | synthetic construct | IAC real-time PCR assay forward primer | ATGCCAGTCAGCATAAGGA | 18 |
| SIACF2 | synthetic construct | IAC real-time PCR assay reverse primer | CAGACCTCTGGTAGGATGTAC | 19 |
| SIACP1 | synthetic construct | IAC real-time PCR probe | 5Cy5/TCGGCACTA/TAO/ CCGACACGAAC/3IAbRQSp/ | 20 |

/56-FAM/ = 5' 6-FAM (fluorescein) fluorophore;
/ZEN/ = ZEN ™ internal quencher, made by Integrated DNA Technologies;
/3IABkFQ/ = 3' Iowa Black ® FQ terminal quencher, made by Integrated DNA Technologies;
/56-ROXN/ = 5' ROX (carboxy-X-rhodamine) n-hydroxysuccinimide ester fluorophore;
/5HEX/ = 5' HEX (hexachlorofluorescein) fluorophore;
/5Cy5/ = 5' Cy5 (cyanine) fluorophore;
/TAO/ = TAO ™ internal quencher, made by Integrated DNA Technologies;
/3IAbRQSp/ = 3' Iowa Black ® RQ terminal quencher, made by Integrated DNA Technologies.

To generate the lpg0768 gene nucleotide sequence for *L. pneumophila* serogroup 1 strains, conventional PCR was performed using the sequencing primers outlined in Table 5(a) on the thermal cycler (iCycler iQ thermal cycler; Bio-Rad Laboratories Inc., California, USA). All reactions were carried out in a final volume of 50 μl, containing 5 μl 10×buffer (15 mM $MgCl_2$), 1 μl forward and reverse primers (0.2 μM final conc.), 2 μl DNA polymerase (Taq; 1 U/μl, Roche Diagnostics, Basel, Switzerland), 1 μl dNTP mix (10 mM deoxynucleoside triphosphate set; Roche Diagnostics), 5 μl of template DNA and 35 μl nuclease free water (Applied Biosystems/Ambion, Texas, USA). The cycling parameters consisted of initial denaturation at 95° C. for 5 minutes, followed by 35 cycles of denaturation at 95° C. (1 minutes), annealing at 50° C. (1 minutes), and extension at 72° C. (1 minutes), with a final elongation step at 72° C. for 10 minutes.

PCR products were visualised on a 1.5% agarose gel and subsequently purified using a PCR product purification kit (High Pure Product Purification Kit; Roche Diagnostics). Purified PCR products were sent for sequencing externally (Sequiserve, Vaterstetten, Germany).

Assay Design

All oligonucleotide primers and probes used in this example were designed in accordance with published guidelines. All oligonucleotide primers and probes were purchased from Integrated DNA Technologies (Leuven, Belgium).

Development of an Internal Amplification Control (IAC) for Real-Time PCR

An internal amplification control (IAC) was designed and incorporated in the multiplex assay designed to monitor for PCR inhibition, thermocycler malfunction, degradation of assay components etc. As this multiplex assay is designed for use on environmental samples, a synthetic construct of random sequence was identified to be the most suitable IAC. The synthetic construct sequence is not found in nature and as such the specific oligonucleotide primers and probes will not be mopped up by competing microorganisms commonly found in the environment.

In this example, the following exemplary real-time PCR assay primers and probe for the IAC were used: IAC synthetic construct forward primer (SEQ ID NO. 18), IAC synthetic construct reverse primer (SEQ ID NO. 19), IAC synthetic construct probe (SEQ ID NO. 20). The IAC synthetic construct probe (SEQ ID NO. 20) comprised at least one marker, optionally at least one dye, optionally at least one fluorophore, optionally cyanine (5' Cy5™, Integrated DNA Technologies). Optionally, the synthetic construct probe (SEQ ID NO. 20) comprised at least one fluorescence quenching dye, optionally an internal quencher (TAO™ quencher, Integrated DNA Technologies), optionally a terminal quencher (3' Iowa Black® RQ, Integrated DNA Technologies).

Titrations of synthetic DNA were performed to determine the optimum concentration of IAC target per reaction such that the IAC is always detected without impacting on detection of the primary *Legionella* targets in the multiplex. An internal control concentration of 1000 genome equivalents per reaction allowed for the detection of the IAC all real-time PCR experiments performed.

A multiplex PCR assay was produced using a combination of oligonucleotide primers and probes selected from: the oligonucleotide primers and probes listed in Table 5(a), and the oligonucleotide primers and probes described in example 1, the oligonucleotide primers and probes described in example 2, and the oligonucleotide primers and probes for the IAC synthetic construct described in this example.

Real-Time PCR

To determine the specificity of each of the diagnostics target used in this study, Monoplex real-time PCR was performed on a thermal cycler (LightCycler 480; Roche Diagnostics, Basel, Switzerland) using a probes kit (LightCycler® Probes Master kit; Roche Diagnostics). A final volume of 20 µl was used in each reaction, containing 2× PCR reaction master mixture (master mix) [LightCycler 480 Probes Master (6.4 mM $MgCl_2$)], forward and reverse primer (0.25 mM final conc. for *Legionella* genus and *L. pneumophila* sg1-16 assays; 0.50 mM final conc. for *L. pneumophila* sg1 assay; 0.3 mM final conc. for IAC assay), FAM (0.6 mM final conc.), HEX (0.2 mM final conc.), ROX (0.2 mM final conc.) or CY5 labelled probe (0.6 mM final conc.), template DNA (2 µl) and the volume adjusted to 20 µl with the addition of nuclease free $dH_2O$. The cycling parameters consisted of incubation for 10 minutes at 95° C. to activate enzymes and DNA denaturation followed by 50 cycles of 95° C. for 10 seconds and 60° C. for 30 s, followed by a cooling step at 40° C. for 10 s. The temperature transition rate for all cycling steps was 4.4° C./s while heating and 2.2° C./s while cooling.

Multiplex real-time PCR reactions were carried out on a thermal cycler (LightCycler 480; Roche Diagnostics, Basel, Switzerland) using a probes kit (LightCycler® Probes Master kit; Roche Diagnostics). A final volume of 20 µl was used for each multiplex experiment. The optimised master mix contained 2× PCR reaction master mixture [LightCycler 480 Probes Master (6.4 mM $MgCl_2$)], forward and reverse primer (0.25-0.5 mM final conc.), FAM, HEX, ROX and CY5 labelled dyes (0.2-0.6 µM final conc.), template DNA (5 µl), IAC DNA 1 µl, and the volume adjusted to 20 µl with the addition of nuclease free $dH_2O$. The internal control DNA was diluted to contain 1000 genome equivalents per µl and all other DNAs were tested at a range of 10*3-10*4 genome equivalents per 5 µl. The cycling parameters used were the same as those used in a monoplex format outlined above. A colour compensation file was generated using the technical note outlined in the Advanced Software Functionalities of the operator manual.

Sensitivity and Specificity of the Real-Time PCR Assays

The specificity of each real-time PCR assay was confirmed both in monoplex and multiplex formats using the specificity panel listed in Table 5(b) and Table 5(c). Using the multiplex assay, all of the *Legionella* strains were detected in the *Legionella* genus assay targeting a region of the ssrA gene. A representation of this can be seen in FIG. 4(*a*), in which the negative control is represented by a line marked with stars. The *L. pneumophila* serogroup 1 specific assay targeting a region of the lpg0768 gene was specific for the detection of *L. pneumophila* serogroup 1 isolates. A representation of this can be seen in FIG. 4(*b*), in which the 12 *L. pneumophila* serogroup 1 strains tested are represented by lines marked with circles. All 12 *L. pneumophila* serogroup 1 strains were detected by the assay. The *L. pneumophila* species assay targeting a region of the smpB gene was specific for the detection of the 26 *L. pneumophila* strains tested for and the 41 other *Legionella* species were not detected by this assay. A representation of this can be seen in FIG. 4(*c*), in which the negative control is represented by a line marked with stars. The specificity of the IAC assay was tested using the full specificity panel (Table 5(b) and Table 5(c)) and was specific for the synthetic construct. As the IAC assay is designed using a non-competitive approach, when spiked into the master mix a positive signal should always be observed in the Cy5 channel. A representation of this can be seen in FIG. 4(*d*), in which the no template control is represented by a line marked with stars. The analytical specificity of this multiplex real-time PCR assay is 100%.

To determine the sensitivity of the multiplex real-time PCR assay developed, serial dilutions ranging from 10*4-1 cell equivalent of *L. pneumophila* were tested in triplicate. The limit of detection of the multiplex assay is between 1-10 genome equivalents.

TABLE 5(b)

*Legionella pneumophila* strains used in this study

| Strain | Culture collection | Number | Serogroup |
|---|---|---|---|
| *Legionella pneumophila* | DSM | 7513 | 1 |
| *Legionella pneumophila* | NCTC | 11191 | 1 |
| *Legionella pneumophila* | NCTC | 11231 | 1 |
| *Legionella pneumophila* | NCTC | 11286 | 1 |
| *Legionella pneumophila* | NCTC | 11378 | 1 |
| *Legionella pneumophila* | NCTC | 11404 | 1 |
| *Legionella pneumophila* | DSM | 25019 | 1 |
| *Legionella pneumophila* | DSM | 25021 | 1 |
| *Legionella pneumophila* | DSM | 25199 | 1 |
| *Legionella pneumophila* | DSM | 25200 | 1 |
| *Legionella pneumophila* | DSM | 25213 | 1 |
| *Legionella pneumophila* | DSM | 27564 | 1 |
| *Legionella pneumophila* | NCTC | 11230 | 2 |
| *Legionella pneumophila* | NCTC | 11232 | 3 |
| *Legionella pneumophila* | DSM | 7414 | 4 |
| *Legionella pneumophila* | DSM | 7415 | 5 |
| *Legionella pneumophila* | NCTC | 11417 | 5 |
| *Legionella pneumophila* | NCTC | 11287 | 6 |
| *Legionella pneumophila* | NCTC | 11984 | 7 |
| *Legionella pneumophila* | NCTC | 11985 | 8 |
| *Legionella pneumophila* | NCTC | 11986 | 9 |
| *Legionella pneumophila* | NCTC | 12000 | 10 |
| *Legionella pneumophila* | NCTC | 12179 | 11 |
| *Legionella pneumophila* | NCTC | 12180 | 12 |
| *Legionella pneumophila* | NCTC | 12181 | 13 |
| *Legionella pneumophila* | NCTC | 12174 | 14 |

DSM = The German Collection of Microorganisms;
NCTC = National Collection of Type Cultures

TABLE 5(C)

Other *Legionella* species tested in this study

| Strain | Source |
|---|---|
| *Legionella anisa* | DSM 17627 |
| *Legionella birminghamensis* | DSM 19232 |
| *Legionella birminghamensis* | ATCC 700709 |
| *Fluoribacter bozemanae* (*Legionella bozemanii*) | DSM 16523 |
| *Fluoribacter bozemanae*-2 | NCTC 11975 |
| *Legionella cincinnatiensis* | DSM 19233 |
| *Fluoribacter dumoffii* (*Legionella dumoffii*) | DSM 17625 |
| *Fluoribacter dumoffii* | ATCC 33343 |
| *Legionella erythra* | DSM 17644 |
| *Legionella feeleii*-1 | DSM 17645 |
| *Legionella feeleii*-2 | NCTC 11978 |
| *Flouribacter gormanii* (*Legionella gormanii*) | DSM 16641 |
| *Fluoribacter gormanii* | ATCC 43769 |
| *Legionella hackeliae*-1 | DSM 19214 |
| *Legionella hackeliae*-2 | NCTC 11980 |
| *Legionella jordanis* | DSM 19212 |
| *Legionella jordanis* | ATCC 700762 |
| *Legionella lansingensis* | DSM 19556 |
| *Legionella longbeachae*-1 | DSM 10572 |
| *Legionella maceachwerii* | DSM 10572 |
| *Tatlockia micdadei* (*Legionella micdadei*) | NCTC 11403 |
| *Legionella oakridgensis* | NCTC 11531 |
| *Legionella oakridgensis* | ATCC 700515 |
| *Legionella parisiensis* | DSM 19216 |
| *Legionella wadsworthii* | NCTC 11532 |
| *Legionella adelaidensis* | DSM 19888 |
| *Legionella brunensis* | DSM 19236 |
| *Legionella busanesis* | ATCC-BAA518 |
| *Legionella cherrii* | DSM 19213 |
| *Legionella donaldsonii* | ATCC BAA-693 |
| *Legionella fairfieldensis* | NCTC 12488 |

TABLE 5(C)-continued

| Other *Legionella* species tested in this study | |
|---|---|
| Strain | Source |
| *Legionella fallonii* | CCUG 43887 |
| *Legionella gratiana* | DSM 21233 |
| *Legionella gresilensis* | DSM 21218 |
| *Legionella israelensi* | DSM 19235 |
| *Legionella jamestowniensis* | DSM 19215 |
| *Legionella londoniensis* | DSM 21234 |
| *Legionella moravica* | DSM 19234 |
| *Legionella quinlivanii*-1 | NCTC 12433 |
| *Legionella rubrilicens* | DSM 11884 |
| *Legionella taurinsis* | CCUG 44901 |

DSM = The German Collection of Microorganisms;
ATCC = American Type Culture Collection;
NCTC = National Collection of Type Cultures;
CCUG = Culture Collection, University of Göteborg Multiplex 1

Result Scenario for the Identification of *L. pneumophila* Serogroup 1

Using multiplex 1; if the ssrA genus assay, the lpg0768 assay, the smpB assay, and the IAC diagnostics assays each generate a positive signal, an organism selected from: *L. pneumophila* serogroup 1, is present in the sample.

Result Scenario for the Identification of *L. pneumophila* Serogroup 2-16

Using multiplex 1; if the ssrA genus assay, the smpB assay, and the IAC diagnostics assay each generate a positive signal, but the lpg0768 assay generates a negative signal, an organism selected from: *L. pneumophila* serogroup 2-16, is present in the sample.

Result Scenario for the Identification of *Legionella* Other than *L. pneumophila*

Using multiplex 1; if the ssrA genus assay and the IAC diagnostics assay generate a positive signal, but the smpB assay and the lpg0768 assay generate a negative signal, an organism selected from: *Legionella* species other than *L. pneumophila*, is present in the sample.

Result Scenario for When No *Legionella* are Present in a Sample

Using multiplex 1, if the ssrA genus assay, the lpg0768 assay, and the smpB assay are not detected, but the IAC diagnostics assays generates a positive signal, no organism of the *Legionella* genus is present in the sample Result Scenario for Invalid Result Using multiplex 1, if no positive signal is observed for any diagnostics assay tested for, including the IAC diagnostics assay, the result is considered invalid and must be repeated.

CONCLUSION

The multiplex real-time PCR assay described in this example is the first description of a real-time PCR diagnostics assay for the identification of the *Legionella* genus, *L. pneumophila* (2-16) and *L. pneumophila* serogroup 1 using the novel lpg0768 gene diagnostics targets. This multiplex real-time PCR diagnostics assay takes approximately one hour to perform after genomic DNA extraction and purification and has an analytical specificity of 100% and a sensitivity of less than 10 genome equivalents.

REFERENCES

Halse, T. A., Edwards, J., Cunningham, P. L., Wolfgang, W. J., Dumas, N. B., Escuyer, V. E. & Musser, K. A. (2010) Combined Real-Time PCR and rpoB Gene Pyrosequencing for Rapid Identification of *Mycobacterium tuberculosis* and Determination of Rifampin Resistance Directly in Clinical Specimens. Journal of Clinical Microbiology, 48 (4), 1182-8.

Scheler, O., Glynn, B., Parkel, S., Palta, P., Toome, K., Kaplinski, L., Remm, M., Maher, M. & Kurg, A. (2009) Fluorescent labeling of NASBA amplified tmRNA molecules for microarray applications. BMC Biotechnology, 9 (45), Available from: https://bmcbiotechnol.biomedcentral.com/articles/10.1186/1472-6750-9-45 [Accessed: 23 Sep. 2016].

The invention claimed is:

1. A method for identifying the presence, absence, or quantity of *Legionella pneumophila* serogroup 1 bacteria in a sample, which bacteria comprise a lpg0768 gene, a smpB gene, and a ssrA gene, each of which genes has a respective nucleic acid sequence and an expression product, wherein the method consists of steps:

(a): contacting the sample with at least one primer and/or probe having a nucleic acid sequence defined by at least one of SEQ ID NO. 2, SEQ ID NO. 3, SEQ ID NO. 4, and the reverse complement each thereof, under conditions suitable for a polymerase chain reaction and detecting the presence, absence, or quantity of at least part of the nucleic acid sequence defined by SEQ ID NO. 1 or an expression product thereof, wherein:

(1) the presence of the at least part of the nucleic acid sequence defined by SEQ ID NO. 1 or expression product thereof correlates to the presence of *Legionella pneumophila* serogroup 1 in the sample, (2) the amount of the at least part of the nucleic acid sequence defined by SEQ ID NO. 1 or expression product thereof, if present, correlates to the quantity of *Legionella pneumophila* serogroup 1 in the sample, and (3) the absence of said at least part of the nucleic acid sequence defined by SEQ ID NO. 1 or expression product thereof correlates to the absence of *Legionella pneumophila* serogroup 1 in the sample, thereby identifying the presence, absence, or quantity of *Legionella pneumophila* serogroup 1 bacteria in said sample; and (b): contacting the sample with at least one primer and/or probe having a nucleic acid sequence defined by at least one of SEQ ID NO. 7, SEQ ID NO. 8, SEQ ID NO. 13, SEQ ID NO. 49, SEQ ID NO. 50, SEQ ID NO. 9, SEQ ID NO. 51, SEQ ID NO. 52, and the reverse complement each thereof; and detecting the presence, absence, or quantity of at least part of the nucleic acid sequence defined by SEQ ID NO. 6 or an expression product thereof in said sample; wherein:

(1) the presence of the at least part of the nucleic acid sequence defined by SEQ ID NO. 6 or expression product thereof correlates to the presence of *Legionella pneumophila* in the sample, (2) the amount of the at least part of the nucleic acid sequence defined by SEQ ID NO. 6 or expression product thereof, if present, correlates to the quantity of *Legionella pneumophila* in the sample, and (3) the absence of said at least part of the nucleic acid sequence defined by SEQ ID NO. 6 or expression product thereof correlates to the absence of *Legionella pneumophila* in the sample.

2. The method of claim 1, wherein the method is a multiplex polymerase chain reaction method.

3. The method of claim 1, wherein the sample substantially comprises a water or environmental water sample.

4. The method of claim 1, wherein the *Legionella pneumophila* serogroup 1 bacteria is selected from the group consisting of: *Legionella pneumophila* serogroup 1 strains: gi|395129037 *L. pneumophila*_extended, *L. pneumophila*_str.Philadelphia1(sg1), *L. pneumophila*_str.Paris(sg1), *L. pneumophila*_LPE509(SG1), gi|6688579 *L. pneumophila* (sg1), *L. pneumophila*_str.Lens(sg1), gi|410173912 *L. pneumophila*(sg1), *L. pneumophila*_str.Camperdown1(sg1), *L. pneumophila*_str.Heysham1(sg1), *L. pneumophila*_str.Uppsala3(sg1), *L. pneumophila*2300/99Alcoy(sg1), *L. pneumophila*_str.Corby(sg1), *L. pneumophila*_str.uppsala3.b(sg1), *L. pneumophila*_str.Lorraine(sg1), *L. pneumophila*_str.Goerlitz6543(sg1), *L. pneumophila*_str.HL06041035(sg1), *L. pneumophila*_str.Hextuple_3a(sg1), *L. pneumophila*_str.Hextuple_2q(sg1), *L. pneumophila*(sg1)_DSM7513, *L. pneumophila*(sg1)_NCTC11191, *L. pneumophila*(sg1)_NCTC11231, *L. pneumophila*(sg1)_NCTC11378, *L. pneumophila*(sg1)_NCTC11404, *L. pneumophila*(sg1)_DSM25019, *L. pneumophila*(sg1)_DSM25021, *L. pneumophila*(sg1)_DSM25199, *L. pneumophila*(sg1)_DSM25200, *L. pneumophila*(sg1)_DSM25213, and *L. pneumophila*(sg1)_DSM37564.

* * * * *